US012163119B2

(12) United States Patent
Gill

(10) Patent No.: US 12,163,119 B2
(45) Date of Patent: Dec. 10, 2024

(54) METHODS AND COMPOSITION FOR GENE DELIVERY USING AN ENGINEERED VIRAL PARTICLE

(71) Applicant: THE TRUSTEES OF THE UNIVERSITY OF PENNSYLVANIA, Philadelphia, PA (US)

(72) Inventor: Saar Gill, Philadelphia, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 0 days.

(21) Appl. No.: 18/338,016

(22) Filed: Jun. 20, 2023

(65) Prior Publication Data

US 2024/0165156 A1 May 23, 2024

Related U.S. Application Data

(63) Continuation of application No. 17/517,343, filed on Nov. 2, 2021, now Pat. No. 11,723,927, which is a continuation of application No. 17/198,970, filed on Mar. 11, 2021, now Pat. No. 11,191,784.

(60) Provisional application No. 63/080,501, filed on Sep. 18, 2020, provisional application No. 62/988,074, filed on Mar. 11, 2020, provisional application No. 62/988,195, filed on Mar. 11, 2020.

(51) Int. Cl.

| | |
|---|---|
| ***A61K 39/00*** | (2006.01) |
| ***A61K 39/21*** | (2006.01) |
| ***A61K 48/00*** | (2006.01) |
| ***C07K 14/08*** | (2006.01) |
| ***C07K 14/16*** | (2006.01) |
| ***C07K 14/705*** | (2006.01) |
| ***C07K 16/28*** | (2006.01) |
| ***C12N 5/0783*** | (2010.01) |
| ***C12N 7/00*** | (2006.01) |

(52) U.S. Cl.

CPC ............ *C12N 7/00* (2013.01); *A61K 39/4611* (2023.05); *A61K 39/4631* (2023.05); *A61K 39/464412* (2023.05); *A61K 39/464424* (2023.05); *A61K 39/464838* (2023.05); *C07K 14/08* (2013.01); *C07K 14/705* (2013.01); *C12N 5/0636* (2013.01); *A61K 2239/21* (2023.05); *C12N 2740/15042* (2013.01)

(58) Field of Classification Search

CPC .... C07K 14/005; C07K 14/08; C07K 14/705; C12N 15/86; C12N 15/8676

See application file for complete search history.

(56) References Cited

U.S. PATENT DOCUMENTS

| | | | |
|---|---|---|---|
| 4,797,368 | A | 1/1989 | Carter |
| 5,139,941 | A | 8/1992 | Muzyczka |
| 5,994,136 | A | 11/1999 | Naldini |
| 6,013,516 | A | 1/2000 | Verma |
| 7,906,111 | B2 | 3/2011 | Wilson |
| 8,076,100 | B2 | 12/2011 | Pavlakis |
| 10,415,057 | B2 | 9/2019 | Buchholz |
| 2006/0084093 | A1 | 4/2006 | Lee |
| 2009/0170067 | A1 | 7/2009 | Hatziioannou |
| 2013/0183334 | A1 | 7/2013 | Landau |
| 2016/0185862 | A1 | 6/2016 | Wu |
| 2017/0342132 | A1 | 11/2017 | Fraser |
| 2019/0144885 | A1 | 5/2019 | Costa Fejoz |

FOREIGN PATENT DOCUMENTS

| | | |
|---|---|---|
| WO | 2004041862 | 5/2004 |
| WO | 2009026183 | 2/2009 |
| WO | 2010096561 | 8/2010 |
| WO | 2011043830 | 4/2011 |
| WO | 2016065323 | 4/2016 |
| WO | 2018191750 | 10/2018 |
| WO | 2020006494 | 1/2020 |

OTHER PUBLICATIONS

Extended European Search Report issued May 10, 2024 in European in Patent Application No. 21768077.6.

International Search Report and Written Opinion dated Jun. 30, 2021, of counterpart International Application No. PCT/US2021/021904.

Uchida et al., "Development of a Human Immunodeficiency Virus Type 1-Based Lentiviral Vector That Allows Efficient Transduction of both Human and Rhesus Blood Cells," J. Virol, 83(19): 9854-9862 (Oct. 2009).

Uchida, N. et al., "High-efficiency transduction of rhesus hematopoietic repopulating cells by a modified HIV1-based lentiviral vector," Mol Ther, 20(10):1882-92 (2012).

*Primary Examiner* — Barry A Chestnut

(74) *Attorney, Agent, or Firm* — Saul Ewing LLP; Kathryn Doyle

(57) ABSTRACT

The present invention provides compositions and methods for transducing cells (e.g. T cells or immune cells). Also provided herein are methods of treating a disease in a subject in need thereof.

19 Claims, 27 Drawing Sheets

Specification includes a Sequence Listing.

FIG. 2C gag-pol NGFR MV

| | NGFR POS% | DILUTION | TITER (TU/ml) |
|---|---|---|---|
| | 66.16% | 3 | 3.97E+06 |
| | 54.00% | 9 | 9.72E+06 |
| | **31.57%** | **27** | **1.70E+07** |
| | 12.55% | 81 | 2.03E+07 |
| | 5.60% | 243 | 2.72E+07 |
| | 1.90% | 729 | 2.77E+07 |
| | 0.60% | 2187 | 2.62E+07 |
| | | | |
| MOI | **5** | 3 | 8 |
| T-cell in 500 ul: | 500000 | | |
| virus volume (ul): | **146.65** | 87.99 | 235 |

FIG. 2D xHIV NGFR MV

| | NGFR POS% | DILUTION | TITER (TU/ml) |
|---|---|---|---|
| | 94.60% | 3 | 5.68E+06 |
| | 85.80% | 9 | 1.54E+07 |
| | 71.60% | 27 | 3.87E+07 |
| | 46.17% | 81 | 7.48E+07 |
| | **22.70%** | **243** | **1.10E+08** |
| | 8.90% | 729 | 1.30E+08 |
| | 3.50% | 2187 | 1.53E+08 |
| | | | |
| MOI | **5** | 3 | 8 |
| T-cell in 500 ul: | 500000 | | |
| virus volume (ul): | **22.66** | 13.60 | 36 |

FIG. 3C gag-pol GFP MV

| | GFP POS% | DILUTION | TITER (TU/ml) |
|---|---|---|---|
| | 84.30% | 3 | 5.06E+06 |
| | 85.20% | 9 | 1.53E+07 |
| | 71.30% | 27 | 3.85E+07 |
| | **41.00%** | **81** | **6.64E+07** |
| | 19.60% | 243 | 9.53E+07 |
| | 8.70% | 729 | 1.27E+08 |
| | 2.00% | 2187 | 8.75E+07 |
| | | | |
| MOI | **5** | 3 | 8 |
| T-cell in 500 ul: | 500000 | | |
| virus volume (ul): | **37.64** | 22.58 | 60 |

FIG. 3D xHIV GFP MV

| | GFP POS% | DILUTION | TITER (TU/ml) |
|---|---|---|---|
| | 85.20% | 3 | 5.11E+06 |
| | 79.20% | 9 | 1.43E+07 |
| | 75.70% | 27 | 4.09E+07 |
| | 64.00% | 81 | 1.04E+08 |
| | **38.80%** | **243** | **1.89E+08** |
| | 16.00% | 729 | 2.33E+08 |
| | 6.18% | 2187 | 2.70E+08 |
| | | | |
| MOI | **5** | 3 | 8 |
| T-cell in 500 ul: | 500000 | | |
| virus volume (ul): | **13.26** | 7.95 | 21 |

FIG. 4C gag-pol CAR19 MV

| | CAR19 POS% | DILUTION | TITER (TU/ml) |
|---|---|---|---|
| | 37.00% | 3 | 2.22E+06 |
| | **22.20%** | **9** | **4.00E+06** |
| | 7.90% | 27 | 4.27E+06 |
| | 3.30% | 81 | 5.35E+06 |
| | 1.80% | 243 | 8.75E+06 |
| | 0.10% | 729 | 1.46E+06 |
| | 0.10% | 2187 | 4.37E+06 |
| | | | |
| MOI | **5** | 3 | 8 |
| T-cell in 500 ul: | 500000 | | |
| virus volume (ul): | **625.63** | 375.38 | 1001 |

FIG. 4D xHIV CAR19 MV

| | CAR19 POS% | DILUTION | TITER (TU/ml) |
|---|---|---|---|
| | 77.00% | 3 | 4.62E+06 |
| | 56.50% | 9 | 1.02E+07 |
| | **32.20%** | **27** | **1.74E+07** |
| | 16.40% | 81 | 2.66E+07 |
| | 5.35% | 243 | 2.60E+07 |
| | 1.72% | 729 | 2.51E+07 |
| | 1.90% | 2187 | 8.31E+07 |
| | | | |
| MOI | **5** | 3 | 8 |
| T-cell in 500 ul: | 500000 | | |
| virus volume (ul): | **143.78** | 86.27 | 230 |

FIG. 5C gag-pol NGFR MV

| | NGFR POS% | DILUTION | TITER (TU/ml) |
|---|---|---|---|
| | 73.00% | 3 | 4.38E+06 |
| | 59.00% | 9 | 1.06E+07 |
| | **36.20%** | **27** | **1.95E+07** |
| | 14.50% | 81 | 2.35E+07 |
| | 5.60% | 243 | 2.72E+07 |
| | 2.20% | 729 | 3.21E+07 |
| | 0.70% | 2187 | 3.06E+07 |
| | | | |
| MOI | **5** | 3 | 8 |
| T-cell in 500 ul: | 500000 | | |
| virus volume (ul): | **127.89** | 76.73 | 205 |

FIG. 5D xHIV NGFR MV

| | NGFR POS% | DILUTION | TITER (TU/ml) |
|---|---|---|---|
| | 92.50% | 3 | 5.55E+06 |
| | 83.60% | 9 | 1.50E+07 |
| | 75.30% | 27 | 4.07E+07 |
| | 52.50% | 81 | 8.51E+07 |
| | **26.40%** | **243** | **1.28E+08** |
| | 10.10% | 729 | 1.47E+08 |
| | 4.20% | 2187 | 1.84E+08 |
| | | | |
| MOI | **5** | 3 | 8 |
| T-cell in 500 ul: | 500000 | | |
| virus volume (ul): | **19.48** | 11.69 | 31 |

FIG. 6C gag-pol GFP MV

| | GFP POS% | DILUTION | TITER (TU/ml) |
|---|---|---|---|
| | 74.30% | 3 | 4.46E+06 |
| | 76.80% | 9 | 1.38E+07 |
| | 50.50% | 27 | 2.73E+07 |
| | **32.00%** | **81** | **5.18E+07** |
| | 14.80% | 243 | 7.19E+07 |
| | 6.25% | 729 | 9.11E+07 |
| | 1.90% | 2187 | 8.31E+07 |
| | | | |
| MOI | **5** | 3 | 8 |
| T-cell in 500 ul: | 500000 | | |
| virus volume (ul): | 48.23 | 28.94 | 77 |

FIG. 6D xHIV GFP MV

| | GFP POS% | DILUTION | TITER (TU/ml) |
|---|---|---|---|
| | 64.60% | 3 | 3.88E+06 |
| | 71.30% | 9 | 1.28E+07 |
| | 69.00% | 27 | 3.73E+07 |
| | 56.60% | 81 | 9.17E+07 |
| | **32.70%** | **243** | **1.59E+08** |
| | 13.90% | 729 | 2.03E+08 |
| | 5.70% | 2187 | 2.49E+08 |
| | | | |
| MOI | **5** | 3 | 8 |
| T-cell in 500 ul: | 500000 | | |
| virus volume (ul): | **15.73** | 9.44 | 25 |

FIG. 7C gag-pol CAR19 MV

| | CAR19 POS% | DILUTION | TITER (TU/ml) |
|---|---|---|---|
| | **11.90%** | **3** | **7.14E+05** |
| | 7.70% | 9 | 1.39E+06 |
| | 3.60% | 27 | 1.94E+06 |
| | 1.70% | 81 | 2.75E+06 |
| | 1.20% | 243 | 5.83E+06 |
| | 0.90% | 729 | 1.31E+07 |
| | 0.10% | 2187 | 4.37E+06 |
| | | | |
| MOI | **5** | 3 | 8 |
| T-cell in 500 ul: | 500000 | | |
| virus volume (ul): | **3501.40** | 2100.84 | 5602 |

FIG. 7D xHIV CAR19 MV

| | CAR19 POS% | DILUTION | TITER (TU/ml) |
|---|---|---|---|
| | 30.40% | 3 | 1.82E+06 |
| | 18.60% | 9 | 3.35E+06 |
| | **11.80%** | **27** | **6.37E+06** |
| | 5.50% | 81 | 8.91E+06 |
| | 2.40% | 243 | 1.17E+07 |
| | 1.60% | 729 | 2.33E+07 |
| | 1.60% | 2187 | 7.00E+07 |
| | | | |
| MOI | **5** | 3 | 8 |
| T-cell in 500 ul: | 500000 | | |
| virus volume (ul): | **392.34** | 235.40 | 628 |

KIRCAR20 expression results in significant in vitro cytotoxicity. KIRCAR20-transduced T cells (transduction efficiency 17%) were incubated with luciferase-expressing Z138 lymphoma cells at different E:T ratios. Cytotoxicity was evaluated after 48 hours as a measure of living cells using bioluminescence.

METHODS AND COMPOSITION FOR GENE DELIVERY USING AN ENGINEERED VIRAL PARTICLE

CROSS-REFERENCE TO RELATED APPLICATIONS

This application is a continuation of U.S. patent application Ser. No. 17/517,343, filed Nov. 2, 2021, which is a continuation of U.S. patent application Ser. No. 17/198,970, filed Mar. 11, 2021, which issued as U.S. Pat. No. 11,191,784 on Dec. 7, 2021, which claims priority to U.S. Provisional Application No. 62/988,195 filed Mar. 11, 2020, to U.S. Provisional Application No. 62/988,074 filed Mar. 11, 2020, and to U.S. Provisional Application No. 63/080,501 filed Sep. 18, 2020, each of which is herein incorporated by reference in its entirety.

REFERENCE TO SEQUENCE LISTING

The Sequence Listing concurrently submitted herewith as a XML file named "046483-7300US2," created on Jun. 15, 2023 and having a size of 37,068 bytes is herein incorporated by reference pursuant to 37 C.F.R. § 1.52(e)(5).

BACKGROUND OF THE INVENTION

CAR T cell therapy has generated exciting results, culminating in four recent FDA approvals and the recent availability of commercial products in the U.S. However, the current personalized cellular product platform is expensive, cumbersome and time-consuming. Specifically, the state of the art of gene transfer into T cells for cancer therapy includes a variety of ex vivo approaches that range from viral (e.g. lentiviral transduction) to non-viral approaches (e.g. electroporation of transposon plasmids). Patients receive ex vivo manufactured CAR T cells. Among the major clinical issues facing patients and physicians is the duration of the ex vivo manufacturing process, which is at least 17 days and often much longer. Additional logistical issues that limit access, increase time-to-treatment, and generate costs include apheresis availability, GMP suites availability in time for manufacturing, and release testing of each product, which is thus treated as a new lot. With over 200 CAR T cell trials in progress world-wide and a burgeoning development pipeline, manufacturing is a critical bottleneck.

SUMMARY OF THE INVENTION

The present invention provides, in part, CAR technology that transforms the paradigm of CAR T therapy and circumvents ex vivo manufacturing issues. Among other things, the present invention provides methods and compositions for in vivo CAR gene delivery using an engineered viral particle or viral vector system. In particular, the present invention contemplates an engineered viral particle or viral vector system that generates cell-based immune responses to specific target cells. Thus, the present invention promises an off-the-shelf CAR drug product more closely resembles a traditional pharmaceutical in its ease of use, deliverability and manufacturing. Furthermore, the engineered viral particle or viral vector system of the present invention may be used to deliver transgenes for treatment of genetic diseases beyond cancer. Accordingly, in certain aspects, the present disclosure provides an engineered viral particle comprising an engineered envelope harboring a mutated fusion protein, a chimeric gag protein, an engineered targeting moiety for binding to a target cell, wherein the mutated fusion protein does not bind to its natural receptor; and a nucleic acid encoding a polypeptide of interest.

In certain exemplary embodiments, the chimeric gag protein is xHIV gag protein.

In certain exemplary embodiments, the targeting moiety is fused to the mutated fusion protein.

In certain exemplary embodiments, the viral particle is a lentivirus pseudotyped with a measles virus (MV) hemagglutinin (HA) protein or an MV fusion (F) protein and the MV-HA protein or the MV-F protein comprises a mutated binding domain compared to its naturally occurring receptor.

In certain exemplary embodiments, the targeting moiety is fused to the MV-HA protein or the MV-F protein.

In certain exemplary embodiments, the targeting moiety is a scFv, an antigen binding domain, a DARPIN, a FN3 domain, or any combination thereof. In certain exemplary embodiments, the targeting moiety is selected from the group consisting of Stem Cell Factor protein (SCF, KIT-ligand, KL, or steel factor) or a moiety that binds to cKit (CD117), CD4, CD8, CD3, CD5, CD6, CD7, CD2, TCR alpha, TCR beta, TCR gamma, TCR delta, CD10, CD34, CD110, CD33, CD14, CD68, CCR7, CD62L, CD25, CCR2, CCR3, CCR4, CCR5, CCR6, CCR7, and CXCR3.

In certain exemplary embodiments, the polypeptide of interest is a chimeric antigen receptor (CAR) or a portion thereof. In certain exemplary embodiments, the chimeric antigen receptor comprises an extracellular domain, transmembrane domain, and an intracellular signaling domain.

In some embodiments, the extracellular domain binds specifically to an antigen expressed at the surface of a cell. In other embodiments, the antigen is a marker expressed by both normal cells and cancer cells, e.g., a lineage marker, e.g., CD19 or CD123 on B cells. In one embodiment, the antigen is a cell surface molecule that is overexpressed in a cancer cell in comparison to a normal cell. In another embodiment, the antigen is a cell surface molecule that is aberrantly expressed on a cancer cell, for example, a molecule that comprises deletions, additions or mutations in comparison to the molecule expressed on a normal cell. In some embodiments, the antigen will be expressed exclusively on the cell surface of a cancer cell, entirely or as a fragment, and not expressed on the surface of a normal cell.

In certain exemplary embodiments, the extracellular domain binds to CD8, CCR7, CD20, CD22, CD123, CD38, CD19, BCMA, CD33, or CD79b.

In certain exemplary embodiments, the polypeptide of interest is a hemoglobin beta chain.

In certain exemplary embodiments, the viral particle is a pseudotyped lentiviral vector, an adenovirus, or an adeno-associated virus. In certain exemplary embodiments, the pseudotyped lentiviral vector is pseudotyped with a paramyxovirus, such as a morbillivirus, such as a measles virus glycoprotein or a henipavirus such as Nipah virus (NiV) glycoprotein. In certain exemplary embodiments, the pseudotyped vector is pseudotyped with a F protein or H protein of a morbillivirus. In some embodiments, the pseudotyped vector is pseudotyped with a G protein of a Nipah Virus.

In another aspect, the instant disclosure provides a method of in vivo gene delivery comprising administering an engineered viral particle to a subject in need of delivery of a protein of interest or a nucleic acid molecule of interest. In some embodiments, the engineered viral particle comprises an engineered envelope harboring a mutated fusion protein, a chimeric gag protein and an engineered targeting moiety for binding to a target cell, wherein the mutated fusion protein does not bind to its natural receptor; and a nucleic acid encoding a polypeptide of interest. The administration of the engineered viral particle induces an in vivo activity in the target cell associated with the polypeptide of interest.

In certain exemplary embodiments, the chimeric gag protein is xHIV gag protein.

In certain exemplary embodiments, the target cell is a T cell, a CD4+ T cell, a CD8+ T cell, a NK cell, an alpha-beta T cell, a gamma-delta T cell, a lymphoid progenitor cell, a hematopoietic stem cell, a myeloid cell, a monocyte, a macrophage, a central memory T cell, a naïve T cell, an activated T cell, a regulatory T Cell (Treg), or a T-Cell$^{CD8-CCR7+}$.

In another aspect, the instant disclosure provides a cell comprising a polypeptide of interest encoded for by any of the engineered viral particles disclosed herein. In certain exemplary embodiments, the cell is a T cell, a CD4+ T cell, a CD8+ T cell, a NK cell, an alpha-beta T cell, a gamma-delta T cell, a lymphoid progenitor cell, a hematopoietic stem cell, a myeloid cell, a monocyte, a macrophage, a central memory T cell, a naïve T cells, an activated T cell, or a regulatory T Cell (Treg), or a T-Cell$^{CD8+CCR7+}$.

In another aspect, the instant disclosure provides a method of treating a disease in a subject. The method comprises administering to the subject any of the engineered viral particles disclosed herein, wherein the engineered viral particle expresses the polypeptide of interest in a cell. In certain exemplary embodiments, the disease is cancer or sickle cell disease, or genetic disease of the bone marrow or a hemoglobinopathy. In certain exemplary embodiments, the cell is a T cell, a CD4+ T cell, a CD8+ T cell, a NK cell, an alpha-beta T cell, a gamma-delta T cell, a lymphoid progenitor cell, a hematopoietic stem cell, a myeloid cell, a monocyte, a macrophage, a central memory T cell, a naïve T cells, an activated T cell, a regulatory T Cell (Treg), or a T-Cell$^{CD8-CCR7+}$.

In another aspect, the instant disclosure provides a viral vector system comprising a first viral particle and a second viral particle. The first viral particle comprises a chimeric gag protein, a first targeting moiety that binds to a first target on a cell and a first nucleic acid molecule that encodes a first portion of a protein or a polypeptide of interest. The second viral particle comprises a chimeric gag protein, a second targeting moiety that binds to a second target on the cell and a second nucleic acid molecule that encodes a second portion of the protein or the polypeptide of interest. The first and second portions of the protein or the polypeptide are capable of forming a complete protein or polypeptide of interest inside the cell. In certain exemplary embodiments, the chimeric gag protein is xHIV gag protein.

In certain exemplary embodiments, the first target and the second target are different.

In certain exemplary embodiments, the protein or polypeptide of interest is a chimeric antigen receptor. In certain exemplary embodiments, the chimeric antigen receptor comprises an extracellular domain, transmembrane domain, and an intracellular signaling domain. In certain exemplary embodiments, the extracellular domain binds to CD8, CCR7, CD20, CD22, CD123, CD38, CD19, BCMA, CD33, or CD79b.

In certain exemplary embodiments, the protein or polypeptide is a hemoglobin beta chain.

In certain exemplary embodiments, the first targeting moiety and the second targeting moiety are each independently selected from the group consisting of a protein that binds to the first target, an antigen binding domain, a DARPIN, and a FN3 domain, or any combination thereof. In certain exemplary embodiments, the first targeting moiety and the second targeting moiety are each independently selected from the group consisting of Stem Cell Factor protein (SCF, KIT-ligand, KL, or steel factor) or a moiety that binds to cKit (CD117), CD4, CD8, CD3, CD5, CD6, CD7, CD2, TCR alpha, TCR beta, TCR gamma, TCR delta, CD10, CD34, CD110, CD33, CD14, CD68, CCR7, CD62L, CD25, CCR2, CCR3, CCR4, CCR5, CCR6, CCR7, and CXCR3. In certain exemplary embodiments, the first targeting moiety is selected from the group consisting of Stem Cell Factor protein (SCF, KIT-ligand, KL, or steel factor) or a moiety that binds to cKit (CD117), CD4, CD8, CD3, CD5, CD6, CD7, CD2, TCR alpha, TCR beta, TCR gamma, TCR delta, CD10, CD34, CD110, CD33, CD14, or CD68. In certain exemplary embodiments, the second targeting moiety binds to CCR7, CD62L, CD25, CCR2, CCR3, CCR4, CCR5, CCR6, CCR7, or CXCR3.

In certain exemplary embodiments, the first target and the second target are each independently selected from the group consisting of cKit (CD117), CD4, CD8, CD3, CD5, CD6, CD7, CD2, TCR alpha, TCR beta, TCR gamma, TCR delta, CD10, CD34, CD110, CD33, CD14, CD68, CCR7, CD62L, CD25, CCR2, CCR3, CCR4, CCR5, CCR6, CCR7, and CXCR3. In certain exemplary embodiments, the first target is cKit (CD117), CD4, CD8, CD3, CD5, CD6, CD7, CD2, TCR alpha, TCR beta, TCR gamma, TCR delta, CD10, CD34, CD110, CD33, CD14, or CD68. In certain exemplary embodiments, the second target is CCR7, CD62L, CD25, CCR2, CCR3, CCR4, CCR5, CCR6, CCR7, or CXCR3.

In certain exemplary embodiments, the first viral vector is a pseudotyped viral vector. In certain exemplary embodiments, the second viral vector is a pseudotyped viral vector.

In certain exemplary embodiments, the first and second viral vector are each, independently, a pseudotyped lentiviral vector, an adenovirus, or an adeno-associated virus. In certain exemplary embodiments, the pseudotyped lentiviral vector is pseudotyped with a morbillivirus, such as a measles virus, glycoprotein and/or a Nipah virus glycoprotein. In certain exemplary embodiments, the first and/or second viral vector is pseudotyped with a F protein or H protein of a morbillivirus.

In certain exemplary embodiments, the cell is a T cell, a CD4+ T cell, a CD8+ T cell, a NK cell, an alpha-beta T cell, a gamma-delta T cell, a lymphoid progenitor cell, a hematopoietic stem cell, a myeloid cell, a monocyte, a macrophage, a central memory T cell, a naïve T cell, an activated T cell, a regulatory T Cell (Treg), or a T-Cell$^{CD8-CCR7+}$.

In certain exemplary embodiments, the protein or polypeptide is a chimeric antigen receptor or a hemoglobin beta chain.

In certain exemplary embodiments, the first and second portions of the protein or polypeptide form a complete protein in the presence of a dimerizing agent. In certain exemplary embodiments, the dimerizing agent is rimiducid ((1R)-3-(3,4-dimethoxyphenyl)-1-[3-({[2-(2-{3-[(1R)-3-(3,4-dimethoxyphenyl)-1-[(2S)-1-[(2S)-2-(3,4,5-trimethoxyphenyl)butanoyl]piperidine-2-carbonyloxy]propyl]phenoxy}acetamido)ethyl]carbamoyl}methoxy)phenyl]propyl (2S)-1-[(2S)-2-(3,4,5-trimethoxyphenyl)butanoyl]piperidine-2-carboxylate (AP1903)), erythropoietin or the dimerizing agent can be a soluble drug or hormone that naturally binds homodimers or heterodimers such as erythropoietin or thrombopoietin, or rapamycin.

In certain exemplary embodiments, the first and second portions of the protein or polypeptide can bind together through the excision of an intein domain.

In certain exemplary embodiments, the first portion of the protein comprises an extracellular domain of a chimeric antigen receptor and the second portion of the protein comprises the transmembrane domain, and an intracellular signaling domain.

In another aspect, the instant disclosure provides a cell comprising any of the viral vector systems disclosed herein. In certain exemplary embodiments, the cell is a T cell, a CD4+ T cell, a CD8+ T cell, a NK cell, an alpha-beta T cell, a gamma-delta T cell, a lymphoid progenitor cell, a hematopoietic stem cell, a myeloid cell, a monocyte, a macrophage, a central memory T cell, a naïve T cells, an activated T cell, or a regulatory T Cell (Treg), or a T-Cell$^{CD8-CCR7+}$.

In another aspect, the instant disclosure provides a method of in vivo gene delivery comprising administering to a subject in need thereof a first viral particle and a second viral particle. The first viral particle comprises a chimeric gag protein, a first targeting moiety that binds to a first target on a cell and a first nucleic acid molecule that encodes a first portion of a protein or a polypeptide of interest. The second viral particle comprises a chimeric gag protein, a second targeting moiety that binds to a second target on the cell and a second nucleic acid molecule that encodes a second portion of the protein or the polypeptide of interest. The first and second portions of the protein or the polypeptide are capable of forming a complete protein or polypeptide of interest inside the cell. In certain exemplary embodiments, the chimeric gag protein is xHIV gag protein.

In certain exemplary embodiments, the method further comprises administering a dimerizing agent to form the protein or polypeptide in the subject.

In certain exemplary embodiments, the first portion and the second portion comprise an intein domain and the intein domain is excised to conjugate the first and second portion to form the protein or polypeptide.

In certain exemplary embodiments, the cell is a T cell, a CD4+ T cell, a CD8+ T cell, a NK cell, an alpha-beta T cell, a gamma-delta T cell, a lymphoid progenitor cell, a hematopoietic stem cell, a myeloid cell, a monocyte, a macrophage, a central memory T cell, a naïve T cells, an activated T cell, a regulatory T Cell (Treg), or a CD8+naïve/central memory cell (CD8+CCR7+) and CD4+naïve/central memory cell (CD4+CCR7+).

In certain exemplary embodiments, the protein or polypeptide is a chimeric antigen receptor. In certain exemplary embodiments, the protein or polypeptide is a hemoglobin beta chain.

In certain exemplary embodiments, the first viral vector is a pseudotyped viral vector. In certain exemplary embodiments, the second viral vector is a pseudotyped viral vector. In certain exemplary embodiments, the first and second viral vector are each, independently, a pseudotyped lentiviral vector, an adenovirus, or an adeno-associated virus. In certain exemplary embodiments, the pseudotyped lentiviral vector is pseudotyped with a morbillivirus, such as a measles virus glycoprotein and/or a Nipah virus glycoprotein. In certain exemplary embodiments, the first and/or second viral vector is pseudotyped with a F protein or H protein of a morbillivirus.

In certain exemplary embodiments, an engineered viral particle is provided comprising an engineered envelope comprising a polypeptide having the amino acid sequence of SEQ ID NO: 9; a heterologous polypeptide targeting moiety for binding to a target cell; and a nucleic acid molecule encoding a heterologous polypeptide of interest.

In another aspect, the instant disclosure provides a method of treating a disease in a subject. The method comprises administering to the subject a first viral particle and a second viral particle. The first viral particle comprises a chimeric gag protein, a first targeting moiety that binds to a first target on a cell and a first nucleic acid molecule that encodes a first portion of a protein or a polypeptide of interest. The second viral particle comprises a chimeric gag protein, a second targeting moiety that binds to a second target on the cell and a second nucleic acid molecule that encodes a second portion of the protein or the polypeptide of interest. The first and second portions of the protein or the polypeptide are capable of forming a complete protein or polypeptide of interest inside the cell.

In some embodiments, the disease is a cancer or a genetic disease including, but not limited to, e.g., bone marrow disease, hemoglobinopathy, and sickle cell disease.

In certain exemplary embodiments, the disease is cancer or sickle cell disease.

In certain exemplary embodiments, the method further comprises administering a dimerizing agent to form the protein or polypeptide in the cell.

In certain exemplary embodiments, the first portion and the second portion comprise an intein domain and the intein domain is excised to conjugate the first and second portion to form the protein or polypeptide.

In certain exemplary embodiments, the cell is a T cell, a CD4+ T cell, a CD8+ T cell, a NK cell, an alpha-beta T cell, a gamma-delta T cell, a lymphoid progenitor cell, a hematopoietic stem cell, a myeloid cell, a monocyte, a macrophage, a central memory T cell, a naïve T cells, an activated T cell, a regulatory T Cell (Treg), or a T-Cell$^{CD8-CCR7+}$.

In certain exemplary embodiments, the protein or polypeptide is a chimeric antigen receptor. In certain exemplary embodiments, the protein or polypeptide is a hemoglobin beta chain.

In certain exemplary embodiments, the first viral vector is a pseudotyped viral vector. In certain exemplary embodiments, the second viral vector is a pseudotyped viral vector. In certain exemplary embodiments, the first and second viral vector are each, independently, a pseudotyped lentiviral vector, an adenovirus, or an adeno-associated virus. In certain exemplary embodiments, the pseudotyped lentiviral vector is pseudotyped with a morbillivirus, such as a measles virus, glycoprotein and/or a Nipah virus glycoprotein. In certain exemplary embodiments, the first and/or second viral vector is pseudotyped with a F protein or H protein of a morbillivirus.

BRIEF DESCRIPTION OF THE DRAWINGS

The foregoing and other features and advantages of the embodiments provided herein will be more fully understood from the following detailed description of illustrative embodiments taken in conjunction with the accompanying drawings.

FIG. 1A illustrates a MV-pseudotyped lentiviral vector system comprising an HIV gag-pol sequence. FIG. 1B is a schematic illustrating a non-limiting embodiment of a MV-pseudotyped lentiviral vector system, wherein the HIV gag sequence is replaced with a sequence encoding xHIV (SEQ ID NO: 5), a chimeric gag protein from SIV and HIV.

FIGS. 2A-2D depict results from experiments wherein activated PBMCs were transduced with gag-pol NGFR MV (FIG. 2A and FIG. 2C) or xHIV NGFR MV (FIG. 2B and FIG. 2D). Results from day 4 are shown.

FIGS. 3A-3D depict results from experiments wherein activated PBMCs were transduced with gag-pol GFP MV (FIG. 3A and FIG. 3C) or xHIV GFP MV (FIG. 3B and FIG. 3D). Results from day 4 are shown.

FIGS. 4A-4D depict results from experiments wherein activated PBMCs were transduced with gag-pol CAR-19 MV (FIG. 4A and FIG. 4C) or xHIV CAR-19 MV (FIG. 4B and FIG. 4D). Results from day 4 are shown.

FIGS. 5A-5D depict results from experiments wherein activated PBMCs were transduced with gag-pol NGFR MV (FIG. 5A and FIG. 5C) or xHIV NGFR MV (FIG. 5B and FIG. 5D). Results from day 12 are shown.

FIGS. 6A-6D depict results from experiments wherein activated PBMCs were transduced with gag-pol GFP MV (FIG. 6A and FIG. 6C) or xHIV GFP MV (FIG. 6B and FIG. 6D). Results from day 12 are shown.

FIGS. 7A-7D depict results from experiments wherein activated PBMCs were transduced with gag-pol CAR-19 MV (FIG. 7A and FIG. 7C) or xHIV CAR-19 MV (FIG. 7B and FIG. 7D). Results from day 12 are shown.

DEFINITIONS

Figure 1A:
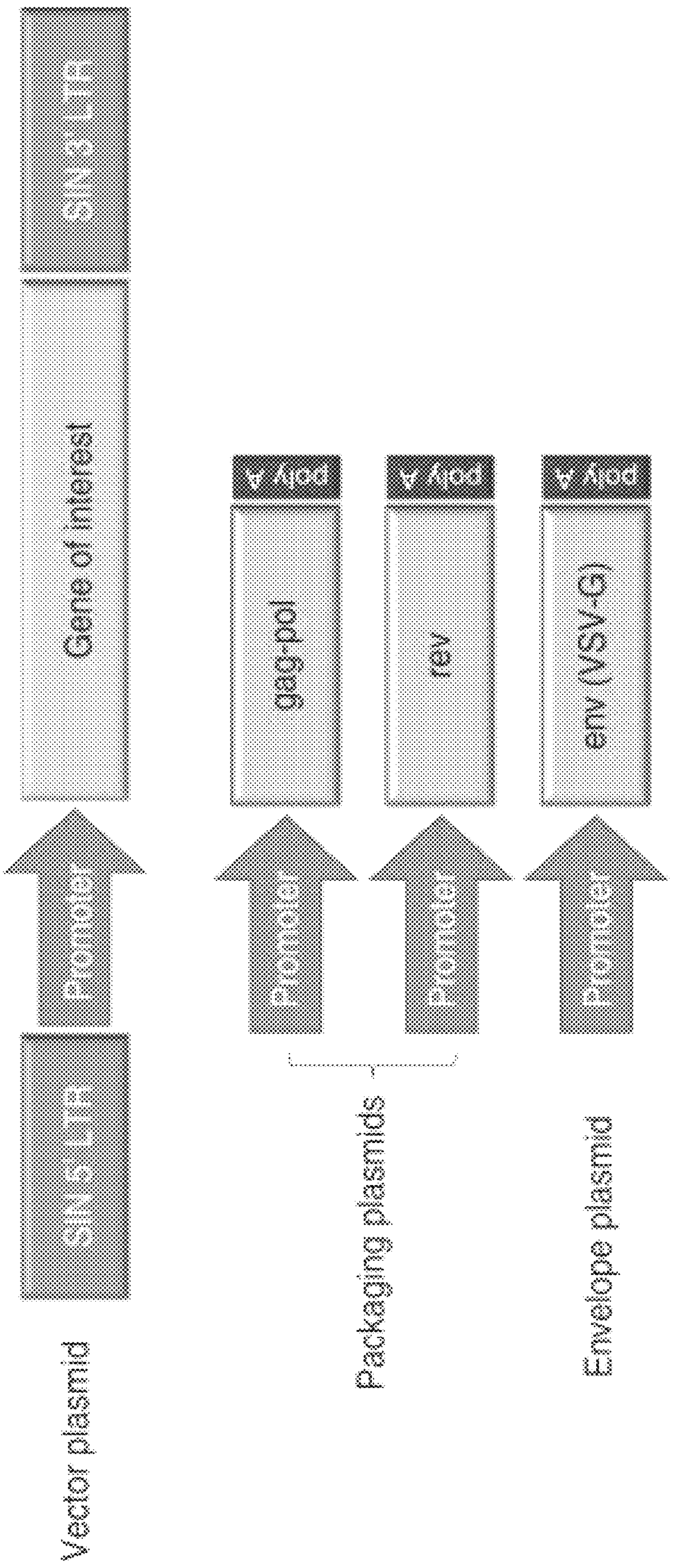
FIGS. 1A-1B are schematics illustrating measles virus (MV)-pseudotyped lentiviral vectors and viral vector systems.

Unless otherwise defined, scientific and technical terms used herein have the meanings that are commonly understood by those of ordinary skill in the art. In the event of any latent ambiguity, definitions provided herein take precedent over any dictionary or extrinsic definition. Unless otherwise required by context, singular terms shall include pluralities and plural terms shall include the singular. The use of "or" means "and/or" unless stated otherwise. The use of the term "including," as well as other forms, such as "includes" and "included," is not limiting.

Generally, nomenclature used in connection with cell and tissue culture, molecular biology, immunology, microbiology, genetics and protein and nucleic acid chemistry and hybridization described herein is well-known and commonly used in the art. The methods and techniques provided herein are generally performed according to conventional methods well known in the art and as described in various general and more specific references that are cited and discussed throughout the present specification unless otherwise indicated. Enzymatic reactions and purification techniques are performed according to manufacturer's specifications, as commonly accomplished in the art or as described herein. The nomenclatures used in connection with, and the laboratory procedures and techniques of, analytical chemistry, synthetic organic chemistry, and medicinal and pharmaceutical chemistry described herein are those well-known and commonly used in the art. Standard techniques are used for chemical syntheses, chemical analyses, pharmaceutical preparation, formulation, and delivery, and treatment of patients.

That the disclosure may be more readily understood, select terms are defined below.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20% or ±10%, ±5%, ±1%, or ±0.1% from the specified value, as such variations are appropriate to perform the disclosed methods.

"Activation," as used herein in reference to a T cell, refers to the state of a T cell that has been sufficiently stimulated to induce detectable cellular proliferation. Activation can also be associated with induced cytokine production, and detectable effector functions. The term "activated T cells" refers to, among other things, T cells that are undergoing cell division.

As used herein, to "alleviate" a disease means reducing the severity of one or more symptoms of the disease.

The term "antigen" as used herein is defined as a molecule that provokes an immune response. This immune response may involve either antibody production, or the activation of specific immunologically-competent cells, or both. The skilled artisan will understand that any macromolecule, including virtually all proteins or peptides, can serve as an antigen. The term "antigen" can also refer to a molecule that an antibody or antibody-like molecule can bind to or is recognized by the antibody or antibody-like molecule.

The term "antibody molecule," "antibody" or antigen binding domain, as that term is used herein, refers to a polypeptide, e.g., an immunoglobulin chain or fragment thereof, comprising at least one functional immunoglobulin variable domain sequence. An antibody molecule encompasses antibodies (e.g., full-length antibodies) and antibody fragments. In some embodiments, an antibody molecule comprises an antigen binding or functional fragment of a full-length antibody, or a full-length immunoglobulin chain. For example, a full-length antibody is an immunoglobulin (Ig) molecule (e.g., an IgG antibody) that is naturally occurring or formed by normal immunoglobulin gene fragment recombinatorial processes. In embodiments, an antibody molecule refers to an immunologically active, antigen binding portion of an immunoglobulin molecule, such as an antibody fragment. An antibody fragment, e.g., functional fragment, comprises a portion of an antibody, e.g., Fab, Fab', F(ab')2, F(ab)2, variable fragment (Fv), domain antibody (dAb), or single chain variable fragment (scFv). A functional antibody fragment binds to the same antigen as that recognized by the intact (e.g., full-length) antibody. The terms "antibody fragment" or "functional fragment" also include isolated fragments consisting of the variable regions, such as the "Fv" fragments consisting of the variable regions of the heavy and light chains or recombinant single chain polypeptide molecules in which light and heavy variable regions are connected by a peptide linker ("scFv proteins"). In some embodiments, an antibody fragment does not include portions of antibodies without antigen binding activity, such as Fc fragments or single amino acid residues. Exemplary antibody molecules include full-length antibodies and antibody fragments, e.g., dAb (domain antibody), single chain, Fab, Fab', and F(ab')2 fragments, and single chain variable fragments (scFvs).

The term "antibody molecule" also encompasses whole or antigen binding fragments of domain, or single domain, antibodies, which can also be referred to as "sdAb" or "VHH." Domain antibodies comprise either VH or VL that can act as stand-alone, antibody fragments. Additionally, domain antibodies include heavy-chain-only antibodies (HCAbs). Domain antibodies also include a CH2 domain of an IgG as the base scaffold into which CDR loops are grafted. It can also be generally defined as a polypeptide or protein comprising an amino acid sequence that is comprised of four framework regions interrupted by three complementarity determining regions. This is represented as FR1-CDR1-FR2-CDR2-FR3-CDR3-FR4. sdAbs can be produced in camelids such as llamas, but can also be synthetically generated using techniques that are well known in the art. The numbering of the amino acid residues of a sdAb or polypeptide is according to the general numbering for VH domains given by Kabat et al. ("Sequence of proteins of immunological interest," US Public Health Services, NIH Bethesda, MD, Publication No. 91, which is hereby incorporated by reference). According to this numbering, FR1 of a sdAb comprises the amino acid residues at positions 1-30, CDR1 of a sdAb comprises the amino acid residues at positions 31-36, FR2 of a sdAb comprises the amino acids at positions 36-49, CDR2 of a sdAb comprises the amino acid residues at positions 50-65, FR3 of a sdAb comprises the amino acid residues at positions 66-94, CDR3 of a sdAb comprises the amino acid residues at positions 95-102, and FR4 of a sdAb comprises the amino acid residues at positions 103-113. Domain antibodies are also described in WO2004041862 and WO2016065323, each of which is hereby incorporated by reference. The domain antibodies can be a targeting moiety as described herein.

Antibody molecules can be monospecific (e.g., monovalent or bivalent), bispecific (e.g., bivalent, trivalent, tetravalent, pentavalent, or hexavalent), trispecific (e.g., trivalent, tetravalent, pentavalent, or hexavalent), or with higher orders of specificity (e.g., tetraspecific) and/or higher orders of valency beyond hexavalency. An antibody molecule can comprise a functional fragment of a light chain variable region and a functional fragment of a heavy chain variable region, or heavy and light chains may be fused together into a single polypeptide.

Furthermore, antigens can be derived from recombinant or genomic DNA. A skilled artisan will understand that any DNA, which comprises a nucleotide sequences or a partial nucleotide sequence encoding a protein that elicits an immune response therefore encodes an "antigen" as that term is used herein. Furthermore, one skilled in the art will understand that an antigen need not be encoded solely by a full length nucleotide sequence of a gene. Moreover, a skilled artisan will understand that an antigen need not be encoded by a "gene" at all. It is readily apparent that an antigen can be generated synthesized or can be derived from a biological sample. Such a biological sample can include, but is not limited to a tissue sample, a tumor sample, a cell or a biological fluid.

As used herein, the term "autologous" is meant to refer to any material, such as a cell, derived from a subject to which it is later to be re-introduced into the same subject.

As used herein, the term "allogeneic" is meant to refer to material, such as a cell, derived from one subject that is later introduced into a different subject.

A "co-stimulatory molecule" or "co-stimulatory receptor" refers to the cognate binding partner on a T cell that specifically binds with a co-stimulatory ligand, thereby mediating a co-stimulatory response by the T cell, such as, but not limited to, proliferation, activation, differentiation, and the like. Co-stimulatory molecules include, but are not limited to CD27, CD28, CD40, or 4-1BB.

"(Co-stimulatory ligand," as the term is used herein, includes a molecule on an antigen presenting cell (e.g., an artificial antigen presenting cell or "aAPC", dendritic cell, B cell, and the like) that specifically binds a cognate co-stimulatory receptor on a T cell, thereby providing a signal which, in addition to the primary signal provided by, for instance, binding of a TCR/CD3 complex to an MHC molecule loaded with peptide, mediates a T cell response, including, but not limited to, proliferation, activation, differentiation, and the like.

A "co-stimulatory signal", as used herein, refers to a signal, which in combination with a primary signal, such as TCR/CD3 ligation, leads to T cell proliferation and/or upregulation or downregulation of key molecules.

A "disease" is a state of health of an animal wherein the animal cannot maintain homeostasis, and wherein if the disease is not ameliorated then the animal's health continues to deteriorate. In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

"Effective amount" or "therapeutically effective amount" are used interchangeably herein, and refer to an amount of a compound, formulation, material, or composition, as described herein effective to achieve a particular biological result or provides a therapeutic or prophylactic benefit. Such results may include, but are not limited to an amount that when administered to a mammal, causes a detectable level of immune cell activation compared to the immune cell activation detected in the absence of the composition. The immune response can be readily assessed by a plethora of art-recognized methods. The skilled artisan would understand that the amount of the composition administered herein varies and can be readily determined based on a number of factors such as the disease or condition being treated, the age and health and physical condition of the mammal being treated, the severity of the disease, the particular compound being administered, and the like.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

The term "epitope" as used herein is defined as a small chemical molecule on an antigen that can elicit an immune response, inducing B and/or T cell responses. An antigen can have one or more epitopes. Most antigens have many epitopes; i.e., they are multivalent. In general, an epitope is roughly about 10 amino acids and/or sugars in size. In some embodiments, the epitope is about 4-18 amino acids, about 5-16 amino acids, about 6-14 amino acids, about 7-12, or about 8-10 amino acids. One skilled in the art understands that generally the overall three-dimensional structure, rather than the specific linear sequence of the molecule, is the main criterion of antigenic specificity and, therefore, distinguishes one epitope from another. Based on the present disclosure, a peptide can be an epitope.

"Expression vector" refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, such as cosmids, plasmids (e.g., naked or contained in liposomes) and viruses (e.g., Sendai viruses, lentiviruses, retroviruses, adenoviruses, and adeno-associated viruses) that incorporate the recombinant polynucleotide.

As used herein, the phrase "ex vivo" in reference to a cell being transduced, transfected or transformed ex vivo, refers to a cell being transduced, transfected or transformed outside of the subject, that is with the cells being removed from the subject before such cells are transduced, transfected or transformed.

"Identity" as used herein refers to the subunit sequence identity between two polymeric molecules particularly between two nucleic acid or amino acid molecules, such as, between two polynucleotide or polypeptide molecules. When two amino acid sequences have the same residues at the same positions; e.g., if a position in each of two polypeptide molecules is occupied by an Arginine, then they are identical at that position. The identity or extent to which two amino acid or two nucleic acid sequences have the same residues at the same positions in an alignment is often expressed as a percentage. The identity between two amino acid or two nucleic acid sequences is a direct function of the number of matching or identical positions; e.g., if half of the positions in two sequences are identical, the two sequences are 50% identical; if 90% of the positions (e.g., 9 of 10), are matched or identical, the two amino acids sequences are 90% identical.

By "substantially identical" is meant a polypeptide or nucleic acid molecule exhibiting at least 50% identity to a reference amino acid sequence (for example, any one of the amino acid sequences described herein) or nucleic acid sequence (for example, any one of the nucleic acid sequences described herein). Preferably, such a sequence is at least 60%, more preferably 80% or 85%, and more preferably 90%, 95% or even 99% identical at the amino acid level or nucleic acid to the sequence used for comparison.

Sequence identity is typically measured using sequence analysis software (for example, Sequence Analysis Software Package of the Genetics Computer Group, University of Wisconsin Biotechnology Center, 1710 University Avenue, Madison, Wis. 53705, BLAST, BESTFIT, GAP, or PILEUP/PRETTYBOX programs). Such software matches identical or similar sequences by assigning degrees of homology to various substitutions, deletions, and/or other modifications. Conservative substitutions typically include substitutions within the following groups: glycine, alanine; valine, isoleucine, leucine; aspartic acid, glutamic acid, asparagine, glutamine; serine, threonine; lysine, arginine; and phenylalanine, tyrosine. In an exemplary approach to determining the degree of identity, a BLAST program may be used, with a probability score between $e^3$ and $e^{100}$ indicating a closely related sequence.

To the extent the invention includes composition comprising various proteins, these proteins may, in some instances, comprise amino acid sequences that have sequence identity to the amino acid sequences disclosed herein. Therefore, in certain embodiments, depending on the particular sequence, the degree of sequence identity is preferably greater than 50% (e.g. 60%, 70%, 75%, 80%, 85%, 90%, 91%, 92%, 93%, 94%, 95%, 96%, 97%, 98%, 99% or more) to the SEQ ID NOs disclosed herein. These proteins may include homologs, orthologues, allelic variants and functional mutants. Typically, 50% identity or more between two polypeptide sequences is considered to be an indication of functional equivalence. Identity between polypeptides is preferably determined by the Smith-Waterman homology search algorithm as implemented in the MPSRCH program (Oxford Molecular), using an affine gap search with parameters gap open penalty—12 and gap extension penalty=1.

These proteins may, compared to the disclosed proteins, include one or more (e.g. 1, 2, 3, 4, 5, 6, 7, 8, 9, 10, etc.) conservative amino acid replacements i.e. replacements of one amino acid with another which has a related side chain. Genetically-encoded amino acids are generally divided into four families: (1) acidic i.e. aspartate, glutamate; (2) basic i.e. lysine, arginine, histidine; (3) non polar i.e. alanine, valine, leucine, isoleucine, proline, phenylalanine, methionine, tryptophan; and (4) uncharged polar i.e. glycine, asparagine, glutamine, cysteine, serine, threonine, tyrosine. Phenylalanine, tryptophan, and tyrosine are sometimes classified jointly as aromatic amino acids. In general, Substitution of single amino acids within these families does not have a major effect on the biological activity. The proteins may have one or more (e.g. 1, 2, 3, 4, 5, 6, 7, 8, 9, 10, etc.) single amino acid deletions relative to the disclosed protein sequences. The proteins may also include one or more (e.g. 1, 2, 3, 4, 5, 6, 7, 8, 9, 10, etc.) insertions (e.g. each of 1, 2, 3, 4 or 5 amino acids) relative to the disclosed protein sequences.

The term "immune response" as used herein is defined as a cellular response to an antigen that occurs when lymphocytes identify antigenic molecules as foreign and induce the formation of antibodies and/or activate lymphocytes to remove the antigen. In some embodiments, the immune response can be against a tumor cell expressing the antigen. In some embodiments, the immune response is facilitated by a T cell expressing a chimeric antigen receptor, such as those, but not limited to, those provided herein.

The term "immunosuppressive" is used herein to refer to reducing overall immune response.

As used herein, the phrase "in vivo" in reference to a cell being transduced, transfected or transformed in vivo, refers to a cell being transduced, transfected or transformed in the subject without the cells being removed from the subject before such cells are transduced, transfected or transformed.

"Isolated" means altered or removed from the natural state. For example, a nucleic acid or a peptide naturally present in a living animal is not "isolated," but the same nucleic acid or peptide partially or completely separated from the coexisting materials of its natural state is "isolated." An isolated nucleic acid or protein can exist in substantially purified form, or can exist in a non-native environment such as, for example, a host cell.

A "lentivirus" as used herein refers to a genus of the Retroviridae family that is able to infect non-dividing cells. Lentiviruses can deliver a significant amount of genetic information into the DNA of the host cell, so they are one of the most efficient methods of a gene delivery vector. HIV, SIV, and FIV are all examples of lentiviruses. Vectors derived from lentiviruses offer the ability to achieve gene transfer in vivo.

By the term "modified" as used herein, is meant a changed state or structure of a molecule or cell as provided herein. Molecules may be modified in many ways, including chemically, structurally, and functionally. Cells may be modified through the introduction of nucleic acids or the expression of heterologous proteins.

By the term "modulating," as used herein, is meant mediating an increase or decrease in the level of a response in a subject compared with the level of a response in the subject in the absence of a treatment or compound, and/or compared with the level of a response in an otherwise identical but untreated subject. The term encompasses perturbing and/or affecting a native signal or response thereby mediating a beneficial therapeutic response in a subject, such as, a human.

As used herein, the following abbreviations for the commonly occurring nucleic acid bases are used: "A" refers to adenosine, "C" refers to cytosine, "G" refers to guanosine, "T" refers to thymidine, and "U" refers to uridine.

The "Nipah virus" (NiV) is member of the family Paramyxoviridae, genus Henipavirus. Nipah virus is an enveloped virus with negative-stranded polarity and a non-segmented RNA genome consisting of helical nucleocapsids. Two strains of Nipah virus include, but are not limited to, the Malaysian (MY) and the Bangladesh (BD) strains.

Unless otherwise specified, a "nucleotide sequence encoding an amino acid sequence" includes all nucleotide sequences that are degenerate versions of each other and that encode the same amino acid sequence. The phrase nucleotide sequence that encodes a protein or an RNA may also include introns to the extent that the nucleotide sequence encoding the protein may in some version contain an intron(s).

The term "oligonucleotide" typically refers to short polynucleotides. It will be understood that when a nucleotide sequence is represented by a DNA sequence (i.e., A, T, C, G), this also provides the corresponding RNA sequence (i.e., A, U, C, G) in which "U" replaces "T."

"Parenteral" administration of a composition includes, e.g., subcutaneous (s.c.), intravenous (i.v.), intramuscular (i.m.), or intrasternal injection, or infusion techniques.

The term "polynucleotide" as used herein is defined as a chain of nucleotides. Furthermore, nucleic acids are polymers of nucleotides. Thus, the terms "nucleic acids" and "polynucleotides" as used herein are interchangeable. As used herein polynucleotides include, but are not limited to, all nucleic acid sequences which are obtained by any methods available in the art, including, without limitation, recombinant methods, i.e., the cloning of nucleic acid sequences from a recombinant library or a cell genome, using cloning technology and PCR, and the like, and by synthetic means.

As used herein, the terms "peptide," "polypeptide," and "protein" are used interchangeably, and refer to a compound comprised of a plurality of amino acid residues covalently linked by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others. The polypeptides include natural peptides, recombinant peptides, synthetic peptides, or a combination thereof.

The term "pseudotyped" or "pseudotyped viral particle", as used herein, refers to a viral particle bearing envelope glycoproteins derived from other viruses having envelopes or a viral vector encoding envelope glycoproteins from a virus that is different from the parental virus. The host range of the vector particles can thus be expanded or altered depending on the type of cell surface receptor used by the glycoprotein. For example, a HIV lentiviral vector can have the HIV envelope glycoprotein be replaced with the VSV envelope glycoprotein. This is just one non-limiting example and other envelop glycoproteins can be used, such as the envelope glycoprotein of the Nipah virus. Therefore, in some embodiments, the viral particle is encoded by a lentivirus that encodes the Nipah viral envelope glycoprotein. In some embodiments, the Nipah viral envelope glycoprotein is glycoprotein F. In some embodiments, the Nipah viral envelope glycoprotein is glycoprotein G. In some embodiments, the pseudotyped viral vector encodes both the Nipah viral glycoprotein F and glycoprotein G. In some embodiments, the pseudotyped viral particle expresses one or both of the Nipah viral glycoprotein F and glycoprotein G.

By the term "specifically binds," as used herein with respect to an antibody, is meant an antibody which recognizes a specific antigen, but does not substantially recognize or bind other molecules in a sample. For example, an antibody that specifically binds to an antigen from one species may also bind to that antigen from one or more species. But, such cross-species reactivity does not itself alter the classification of an antibody as specific. In another example, an antibody that specifically binds to an antigen may also bind to different allelic forms of the antigen. However, such cross reactivity does not itself alter the classification of an antibody as specific. In some instances, the terms "specific binding" or "specifically binding," can be used in reference to the interaction of an antibody, a protein, or a peptide with a second chemical species, to mean that the interaction is dependent upon the presence of a particular structure (e.g., an antigenic determinant or epitope) on the chemical species; for example, an antibody recognizes and binds to a specific protein structure rather than to proteins generally. If an antibody is specific for epitope "A", the presence of a molecule containing epitope A (or free, unlabeled A), in a reaction containing labeled "A" and the antibody, will reduce the amount of labeled A bound to the antibody.

By the term "stimulation," is meant a primary response induced by binding of a stimulatory molecule (e.g., a TCR/CD3 complex) with its cognate ligand thereby mediating a signal transduction event, such as, but not limited to, signal transduction via the TCR/CD3 complex. Stimulation can mediate altered expression of certain molecules, such as downregulation of TGF-beta, and/or reorganization of cytoskeletal structures, and the like.

A "stimulatory molecule," as the term is used herein, means a molecule on a T cell that specifically binds with a cognate stimulatory ligand present on an antigen presenting cell.

A "stimulatory ligand," as used herein, means a ligand that when present on an antigen presenting cell (e.g., an aAPC, a dendritic cell, a B-cell, and the like) can specifically bind with a cognate binding partner (referred to herein as a "stimulatory molecule") on a T cell, thereby mediating a primary response by the T cell, including, but not limited to, activation, initiation of an immune response, proliferation, and the like. Stimulatory ligands are well-known in the art and encompass, inter alia, an MHC Class I molecule loaded with a peptide, an anti-CD3 antibody, a superagonist anti-CD28 antibody, and a superagonist anti-CD2 antibody.

The term "subject" includes living organisms, including those in which an immune response can be elicited (e.g., mammals). A "subject" or "patient," as used therein, may be a human or non-human mammal. Non-human mammals include, for example, livestock and pets, such as ovine, bovine, porcine, canine, non-human primates, feline and murine mammals. In some embodiments, the subject is human.

As used herein, the term "T cell receptor" or "TOR" refers to a complex of membrane proteins that participate in the activation of T cells in response to the presentation of antigen. The TCR is responsible for recognizing antigens bound to major histocompatibility complex molecules. TCR is composed of a heterodimer of an alpha (α) and beta (β) chain, although in some cells the TCR consists of gamma and delta (γ/δ) chains. TCRs may exist in alpha/beta and gamma/delta forms, which are structurally similar but have distinct anatomical locations and functions. Each chain is composed of two extracellular domains, a variable and constant domain. In some embodiments, the TCR may be modified on any cell comprising a TCR, including, for example, a helper T cell, a cytotoxic T cell, a memory T cell, regulatory T cell, natural killer T cell, and gamma delta T cell.

The term "therapeutic" as used herein means a treatment and/or prophylaxis. A therapeutic effect is obtained by suppression, remission, or eradication of a disease state.

The term "transfected" or "transformed" or "transduced" as used herein refers to a process by which exogenous nucleic acid is transferred or introduced into a cell. A "transfected" or "transformed" or "transduced" cell is one which has been transfected, transformed or transduced with exogenous nucleic acid. The cell includes the primary subject cell and its progeny. In some embodiments, the transfection, transformation, or transduction is performed or occurs in vivo.

To "treat" a disease as the term is used herein, means to reduce the frequency or severity of at least one sign or symptom of a disease or disorder experienced by a subject.

As used herein, the term "variant" when used in conjunction to an amino acid sequence refers to a sequence that is at least, or about, 85%, 90%, 91%, 92%, 93%, 94%, 95%, 96%, 97%, 98%, or 99% identical to the reference sequence. In some embodiments, the variant comprises 1, 2, 3, 4, 5, 6, 7, 8, 9, or 10 substitutions. In some embodiments, the substitution is a conservative substitution.

A "vector" is a composition of matter which comprises an isolated nucleic acid encoding a protein or a peptide. Numerous vectors are known in the art including, but not limited to, linear polynucleotides, plasmids, DNA, and RNA. Examples of viral vectors include, but are not limited to, Sendai viral vectors, adenoviral vectors, adeno-associated virus vectors, retroviral vectors, lentiviral vectors, and the like.

A "carrier" or "delivery vehicle" includes viral particles, viruses, polylysine compounds, and liposomes, which facilitate transfer of nucleic acid into cells. A carrier or delivery vehicle can also be used to deliver a protein or peptide to a cell.

As used herein, xHIV and xHIV (i.e., Greek symbol χ(chi)HIV) are used synonymously so as to avoid any confusion derived from electronic or other imaging of this specification.

Ranges: throughout this disclosure, various aspects of the embodiments can be presented in a range format. It should be understood that the description in range format is merely for convenience and brevity and should not be construed as an inflexible limitation. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range. Unless otherwise explicitly stated to the contrary, a range that is disclosed also includes the endpoints of the range.

DETAILED DESCRIPTION

The present invention provides, among other things, compositions and methods for transducing cells (e.g. T cells) in vivo. In some embodiments, these compositions and methods are performed or used without culturing or transducing the cells ex-vivo. In some embodiments, a patient with a malignancy requiring CAR T cell therapy can be treated with an off-the-shelf composition that transduces their T cells in vivo, which generates CAR T cells in situ. These methods and compositions, such as a gene transfer vector (e.g. lentiviral vector) in viral particles, as opposed to ex-vivo transduced cells, can be used, for example, to turn the patient's own lymphoid organs into a bioreactor to produce the CAR T cells. In some embodiments, vectors that can be utilized are those that transduce CD4+ CD8+ T cells with lentiviruses, such as a CD4-specific lentivirus and/or a CD8-specific lentivirus such that only the targeted cells that express both CD4 and CD8 express the transgene of interest based on the combination of the expression products being expressed from the plurality of lentiviruses being used to transduce the cells in vivo.

It is to be understood that the methods described in this disclosure are not limited to particular methods and experimental conditions disclosed herein as such methods and conditions may vary. It is also to be understood that the terminology used herein is for the purpose of describing particular embodiments only, and is not intended to be limiting.

Furthermore, the experiments described herein, unless otherwise indicated, use conventional molecular and cellular biological and immunological techniques within the skill of the art. Such techniques are well known to the skilled worker, and are explained fully in the literature. See, e.g., Ausubel, et al., ed., Current Protocols in Molecular Biology, John Wiley & Sons, Inc., NY, N.Y. (1987-2008), including all supplements, Molecular Cloning: A Laboratory Manual (Fourth Edition) by M R Green and J. Sambrook and Harlow et al., Antibodies: A Laboratory Manual, Chapter 14, Cold Spring Harbor Laboratory, Cold Spring Harbor (2013, 2nd edition).

Engineered Viral Particles

The present invention provides, among other things, compositions that can be used, for example, to selectively transduce a cell expressing specific cell surface markers using viral particles. In some embodiments, the viral particles are used to transduce the cells in vivo. In some embodiments, the viral particles are used to transduce the cells ex vivo. By utilizing viral particles to transduce the same cell type, the viral particles can increase specificity, improve safety by limiting expression of the entire molecule of interest to the specific cell type, and in certain embodiments, provide an additional layer of control by utilizing dimerization domains that require administration of an exogenous agent so that the molecule of interest will form from the first and second portions expressed by the viral particle.

Viral Vector System

The present invention also provides, among other things, compositions that can be used, for example, to selectively transduce a cell expressing specific cell surface markers in vivo or ex vivo using a plurality of viral particles. By utilizing a plurality of viral particles to transduce the same cell type, the viral particles can increase specificity, improve safety by limiting expression of the entire molecule of interest to the specific cell type, and in certain embodiments, provide an additional layer of control by utilizing dimerization domains that require administration of an exogenous agent so that the molecule of interest will form from the first and second portions expressed by the plurality of vectors.

Protein or Polypeptide of Interest

In some embodiments, the viral particle encodes a polypeptide of interest, which can also be referred to as a molecule of interest. In some embodiments, one viral particle provides a viral vector encoding a first portion of a molecule of interest, and another viral particle provides a second viral vector encoding a second portion of a molecule of interest. As provided herein, in some embodiments, the molecule of interest is a chimeric antigen receptor.

In some embodiments, the viral particle delivers a nucleic acid molecule of interest. In some embodiments, the nucleic acid molecule of interest encodes the polypeptide of interest.

In some embodiments, a composition comprising an engineered viral particle comprising an engineered envelope harboring a mutated fusion protein and an engineered targeting moiety for binding to a target cell, wherein the mutated fusion protein does not bind to its natural receptor; and a nucleic acid encoding a polypeptide of interest is provided.

In some embodiments, the gag protein is not chimeric gag and is wild-type gag.

In some embodiments, a composition comprising an engineered viral particle comprising an engineered envelope harboring a mutated fusion protein, a chimeric gag protein, and an engineered targeting moiety for binding to a target cell, wherein the mutated fusion protein does not bind to its natural receptor; and a nucleic acid encoding a polypeptide of interest is provided.

In some embodiments, a composition comprising a first viral particle and a second viral particle are provided. In some embodiments, the first viral particle comprises a chimeric gag protein, a first targeting moiety that binds to a first target on a cell, and a nucleic acid molecule that encodes a first portion of a protein or polypeptide. In some embodiments, the second viral particle comprises a chimeric gag protein, a second targeting moiety that binds to a second target on the cell, and a nucleic acid molecule that encodes a second portion of the protein or the polypeptide. Once expressed in the cell, the first and second portions of the protein or the polypeptide can bind together or interact with one another to form a complete or functional protein or polypeptide.

In certain embodiments, the chimeric gag protein is xHIV gag protein. The chimeric gag protein xHIV is described in Uchida et al. J. Virol, October 2009, p. 9854-9862, contents of which are incorporated by reference herein.

In certain embodiments, the chimeric gag protein, as described herein, comprises SIV and HIV sequences. In certain embodiments, the chimeric gag protein is referred to as xHIV gag protein. In certain embodiments, the xHIV comprises a HIV long-terminal repeat (LTR), a HIV gag protein (gag), a SIV element, a HIV Pol protein (Pol), and a HIV Envelope (Env) protein. In some embodiments, gag, Pol, and/or Env protein is a polyprotein. In certain embodiments, the gag protein, the SIV element, and the Pol protein of the xHIV are encoded by the nucleic acid sequence as set forth in SEQ ID NO: 5.

(5'-3' xHIV gag-pol nt, SEQ ID NO: 5)

atgggtgcgagagcgtcggtattaagcgggggagaattagataaatgggaaaaaattcggttaaggccagggg gaaagaaacaatataaactaaaacatatagtatgggcaagcagggagctagaacgattcgcagttaatcctggc cttttagagacatcagaaggctgtagacaaatactgggacagctacaaccatcccttcagacaggatcagaaga acttagatcattatataatacaatagcagtcctctattgtgtgcatcaaaggatagatgtaaaagacactaaggaag ccttagataagatagaggaagaacaaaacaaaagtaagaaaaaggcacagcaagcagcagctgacacagga aacaacagccaggtcagccaaaattacccagtacaacaaataggtggtaactatgtccacctgccattaagcccg agaacattaaatgcctgggtaaaattgatagaggaaaagaaatttggagcagaagtagtgccaggatttcaggca ctgtcagaaggttgcacccccctatgacattaatcagatgttaaattgtgtgggagaccatcaagcggctatgcaga ttatcagagatattataaacgaggaggttgcagattgggacttgcagcacccacaaccagctccacaacaagga caacttagggagccgtcaggatcagatattgcaggaacaactagttcagtagatgaacaaatccagtggatgtac agacaacagaaccccataccagtaggcaacatttacaggagatggatccaactggggttgcaaaaatgtgtcag aatgtataacccaacaaacattctagatgtaaaacaagggccaaaagagccatttcagagctatgtagacaggttc tacaaaagtttaagagcagaacagacagatgcagcagtaaagaattggatgactcaaacactgctgattcaaaat gctaacccagattgcaagctagtgctgaaggggttgggaccaggagcgacactagaagaaatgatgacagcat gtcagggagtgggggggacccggccataaagcaagagttttggctgaagcaatgagccaagtaacaaatccag ctaccataatgatacagaaaggcaattttaggaaccaaagaaagactgttaagtgtttcaattgtggcaaagaagg gcacatagccaaaaattgcagggcccctaggaaaaagggctgttggaaatgtggaaaggaaggacaccaaat gaaagattgtactgagagacaggctaatttttttagggaagatctggccttcccacaagggaaggccagggaatttt cttcagagcagaccagagccaacagccccaccagaagagagcttcaggtttggggaagagacaacaactccc tctcagaagcaggagccgatagacaaggaactgtatcctttagcttccctcagatcactctttggcagcgacccct cgtcacaataaagataggggggcaattaaaggaagctctattagatacaggagcagatgatacagtattagaag aaatgaatttgccaggaagatggaaaccaaaaatgatagggggaattggaggttttatcaaagtaagacagtatg atcagatactcatagaaatctgcggacataaagctataggtacagtattagtaggacctacacctgtcaacataatt ggaagaaatctgttgactcagattggctgcactttaaattttcccattagtcctattgagactgtaccagtaaaattaa agccaggaatggatggcccaaaagttaaacaatggccattgacagaagaaaaaataaaagcattagtagaaatt tgtacagaaatggaaaaggaaggaaaaatttcaaaaattgggcctgaaaatccatacaatactccagtatttgcca taaagaaaaaagacagtactaaatggagaaaattagtagatttcagagaacttaataagagaactcaagatttctg ggaagttcaattaggaataccacatcctgcagggttaaaacagaaaaaatcagtaacagtactggatgtgggcg atgcatatttttcagttcccttagataaagacttcaggaagtatactgcatttaccatacctagtataaacaatgagac accagggattagatatcagtacaatgtgcttccacagggatggaaaggatcaccagcaatattccagtgtagcat gacaaaaatcttagagccttttagaaaacaaaatccagacatagtcatctatcaatacatggatgatttgtatgtagg atctgacttagaaatagggcagcatagaacaaaaatagaggaactgagacaacatctgttgaggtggggatttac cacaccagacaaaaaacatcagaaagaacctccattcctttggatgggttatgaactccatcctgataaatggaca gtacagcctatagtgctgccagaaaaggacagctggactgtcaatgacatacagaaattagtgggaaaattgaat tgggcaagtcagatttatgcagggattaaagtaaggcaattatgtaaacttcttaggggaaccaaagcactaacag aagtagtaccactaacagaagaagcagagctagaactggcagaaaacagggagattctaaaagaaccggtac atggagtgtattatgacccatcaaaagacttaatagcagaaatacagaagcaggggcaaggccaatggacatat caaatttatcaagagccatttaaaaatctgaaaacaggaaagtatgcaagaatgaagggtgcccacactaatgat gtgaaacaattaacagaggcagtacaaaaaatagccacagaaagcatagtaatatggggaaagactcctaaattt aaattacccatacaaaaggaaacatgggaagcatggtggacagagtattggcaagccacctggattcctgagtg -continued ggagtttgtcaatacccctcccttagtgaagttatggtaccagttagagaaagaacccataataggagcagaaact ttctatgtagatggggcagccaatagggaaactaaattaggaaaagcaggatatgtaactgacagaggaagaca aaaagttgtcccccctaacggacacaacaaatcagaagactgagttacaagcaattcatctagctttgcaggattcg ggattagaagtaaacatagtgacagactcacaatatgcattgggaatcattcaagcacaaccagataagagtgaa tcagagttagtcagtcaaataatagagcagttaataaaaaaggaaaaagtctacctggcatgggtaccagcacac aaaggaattggaggaaatgaacaagtagataaattggtcagtgctggaatcaggaaagtactattttagatggaa tagataaggcccaagaagaacatgagaaatatcacagtaattggagagcaatggctagtgattttaacctaccac ctgtagtagcaaaagaaatagtagccagctgtgataaatgtcagctaaaaggggaagccatgcatggacaagta gactgtagcccaggaatatggcagctagattgtacacatttagaaggaaaagttatcttggtagcagttcatgtagc cagtggatatatagaagcagaagtaattccagcagagacagggcaagaaacagcatacttcctcttaaaattagc aggaagatggccagtaaaaacagtacatacagacaatggcagcaatttcaccagtactacagttaaggccgcct gttggtgggcggggatcaagcaggaatttggcattccctacaatccccaaagtcaaggagtaatagaatctatga ataaagaattaaagaaaattataggacaggtaagagatcaggctgaacatcttaagacagcagtacaaatggca gtattcatccacaattttaaaagaaaaggggggattggggggtacagtgcaggggaaagaatagtagacataat agcaacagacatacaaactaaagaattacaaaaacaaattacaaaaattcaaaattttcgggtttattacagggaca gcagagatccagtttggaaaggaccagcaaagctcctctggaaaggtgaaggggcagtagtaatacaagataa tagtgacataaaagtagtgccaagaagaaaagcaaagatcatcagggattatggaaaacagatggcaggtgat gattgtgtggcaagtagacaggatgaggattaa.

In certain embodiments, the gag protein is encoded by the nucleic acid sequence as set forth in SEQ ID NO: 6.

(5'-3' xHIV gag protein nt, SEQ ID NO: 6)

atgggtgcgagagcgtcggtattaagcgggggagaattagataaatggga aaaaattcggttaaggccagggggaaagaaacaatataaactaaaacata tagtatgggcaagcagggagctagaacgattcgcagttaatcctggcctt ttagagacatcagaaggctgtagacaaatactgggacagctacaaccatc ccttcagacaggatcagaagaacttagatcattatataatacaatagcag tcctctattgtgtgcatcaaaggatagatgtaaaagacactaaggaagcc ttagataagatagaggaagaacaaaacaaaagtaagaaaaaggcacagca agcagcagctgacacaggaaacaacagccaggtcagccaaaattacccag tacaacaaataggtggtaactatgtccacctgccattaagcccgagaaca ttaaatgcctgggtaaaattgatagaggaaaagaaatttggagcagaagt agtgccaggatttcaggcactgtcagaaggttgcaccccctatgacatta atcagatgttaaattgtgtgggagaccatcaagcggctatgcagattatc agagatattataaacgaggaggttgcagattgggacttgcagcacccaca accagctccacaacaaggacaacttagggagccgtcaggatcagatattg caggaacaactagttcagtagatgaacaaatccagtggatgtacagacaa cagaaccccataccagtaggcaacatttacaggagatggatccaactggg gttgcaaaaatgtgtcagaatgtataacccaacaaacattctagatgtaa aacaagggccaaaagagccatttcagagctatgtagacaggttctacaaa agtttaagagcagaacagacagatgcagcagtaaagaattggatgactca -continued aacactgctgattcaaaatgctaacccagattgcaagctagtgctgaagg ggttgggaccaggagcgacactagaagaaatgatgacagcatgtcaggga gtggggggacccggccataaagcaagagttttggctgaagcaatgagcca agtaacaaatccagctaccataatgatacagaaaggcaattttaggaacc aaagaaagactgttaagtgtttcaattgtggcaaagaagggcacatagcc aaaaattgcagggcccctaggaaaaagggctgttggaaatgtggaaagga aggacaccaaatgaaagattgtactgagagacaggctaattttttaggga agatctggccttcccacaagggaaggccagggaattttcttcagagcaga ccagagccaacagccccaccagaagagagatcaggtttggggaagagaca acaactccctctcagaagcaggagccgatagacaaggaactgtatccttt agcttccctcagatcactctttggcagcgacccctcgtcacaataa.

In certain embodiment, the SIV element is encoded by the nucleic acid sequence as set forth in SEQ ID NO: 7. In certain embodiments, the nucleic acid sequence encoding the SIV element is located within the nucleic acid sequence encoding the gag protein as set forth in SEQ ID NO: 6.

(5'-3' xHIV SIV element nt, SEQ ID NO: 7)

aaaattacccagtacaacaaataggtggtaactatgtccacctgccatta agcccgagaacattaaatgcctgggtaaaattgatagaggaaaagaaatt tggagcagaagtagtgccaggatttcaggcactgtcagaaggttgcaccc cctatgacattaatcagatgttaaattgtgtgggagaccatcaagcggct atgcagattatcagagatattataaacgaggaggttgcagattgggactt gcagcacccacaaccagctccacaacaaggacaacttagggagccgtcag -continued gatcagatattgcaggaacaactagttcagtagatgaacaaatccagtgg atgtacagacaacagaaccccataccagtaggcaacatttacaggagatg gatccaactggggttgcaaaaatgtgtcagaatgtataacccaacaaaca ttctagatgtaaaacaagggccaaaagagccatttcagagctatgtagac -continued aggttctacaaaagtttaagagcagaacagacagatgcagcagtaaagaa ttggatgactcaaacactgctgattcaaaatgctaacccagattgcaagc tagtgctgaaggggttggg.

In certain embodiments, the Pol protein is encoded by the nucleic acid sequence as set forth in SEQ ID NO: 8.

(5'-3' xHIV Pol protein nt, SEQ ID NO: 8)

tttttagggaagatctggccttcccacaagggaaggccagggaattttcttcagagcagaccagagccaacagc cccaccagaagagagcttcaggtttggggaagagacaacaactccctctcagaagcaggagccgatagacaa ggaactgtatcctttagcttccctcagatcactctttggcagcgacccctcgtcacaataaagatagggggcaatt aaaggaagctctattagatacaggagcagatgatacagtattagaagaaatgaatttgccaggaagatggaaac caaaaatgatagggggaattggaggttttatcaaagtaagacagtatgatcagatactcatagaaatctgcggaca taaagctataggtacagtattagtaggacctacacctgtcaacataattggaagaaatctgttgactcagattggct gcactttaaattttcccattagtcctattgagactgtaccagtaaaattaaagccaggaatggatggcccaaaagtta aacaatggccattgacagaagaaaaaataaaagcattagtagaaatttgtacagaaatggaaaaggaaggaaaa atttcaaaaattgggcctgaaaatccatacaatactccagtatttgccataaagaaaaaagacagtactaaatggag aaaattagtagatttcagagaacttaataagagaactcaagatttctgggaagttcaattaggaataccacatcctg cagggttaaaacagaaaaaatcagtaacagtactggatgtgggcgatgcatatttttcagttcccttagataaagac ttcaggaagtatactgcatttaccatacctagtataaacaatgagacaccagggattagatatcagtacaatgtgctt ccacagggatggaaaggatcaccagcaatattccagtgtagcatgacaaaaatcttagagccttttagaaaacaa aatccagacatagtcatctatcaatacatggatgatttgtatgtaggatctgacttagaaatagggcagcatagaac aaaaatagaggaactgagacaacatctgttgaggtggggatttaccacaccagacaaaaaacatcagaaagaa cctccattcctttggatgggttatgaactccatcctgataaatggacagtacagcctatagtgctgccagaaaagga cagctggactgtcaatgacatacagaaattagtgggaaaattgaattgggcaagtcagatttatgcagggattaaa gtaaggcaattatgtaaacttcttaggggaaccaaagcactaacagaagtagtaccactaacagaagaagcaga gctagaactggcagaaaacagggagattctaaaagaaccggtacatggagtgtattatgacccatcaaaagactt aatagcagaaatacagaagcaggggcaaggccaatggacatatcaaatttatcaagagccatttaaaaatctgaa aacaggaaagtatgcaagaatgaagggtgcccacactaatgatgtgaaacaattaacagaggcagtacaaaaa atagccacagaaagcatagtaatatggggaaagactcctaaatttaaattacccatacaaaaggaaacatgggaa gcatggtggacagagtattggcaagccacctggattcctgagtgggagtttgtcaataccccctcccttagtgaagt tatggtaccagttagagaaagaacccataataggagcagaaactttctatgtagatggggcagccaatagggaa actaaattaggaaaagcaggatatgtaactgacagaggaagacaaaaagttgtcccccctaacggacacaacaaa tcagaagactgagttacaagcaattcatctagctttgcaggattcgggattagaagtaaacatagtgacagactca caatatgcattgggaatcattcaagcacaaccagataagagtgaatcagagttagtcagtcaaataatagagcagt taataaaaaaggaaaaagtctacctggcatgggtaccagcacacaaaggaattggaggaaatgaacaagtaga taaattggtcagtgctggaatcaggaaagtactatttttagatggaatagataaggcccaagaagaacatgagaaa tatcacagtaattggagagcaatggctagtgattttaacctaccacctgtagtagcaaaagaaatagtagccagct gtgataaatgtcagctaaaaggggaagccatgcatggacaagtagactgtagcccaggaatatggcagctagat tgtacacatttagaaggaaaagttatcttggtagcagttcatgtagccagtggatatatagaagcagaagtaattcc agcagagacagggcaagaaacagcatacttcctcttaaaattagcaggaagatggccagtaaaaacagtacata cagacaatggcagcaatttcaccagtactacagttaaggccgcctgttggtgggcggggatcaagcaggaattt -continued

```
ggcattccctacaatccccaaagtcaaggagtaatagaatctatgaataaagaattaaagaaaattataggacagg

taagagatcaggctgaacatcttaagacagcagtacaaatggcagtattcatccacaattttaaaagaaaagggg

ggattggggggtacagtgcaggggaaagaatagtagacataatagcaacagacatacaaactaaagaattaca

aaaacaaattacaaaaattcaaaattttcgggtttattacagggacagcagagatccagtttggaaaggaccagca

aagctcctctggaaaggtgaaggggcagtagtaatacaagataatagtgacataaaagtagtgccaagaagaaa

agcaaagatcatcagggattatggaaaacagatggcaggtgatgattgtgtggcaagtagacaggatgaggatt

aa.
```

In certain embodiments, the nucleotide sequence encoding gag protein encodes a protein comprising a sequence as set forth in SEQ ID NO: 9.

```
                                             (SEQ ID NO: 9)
MGARASVLSGGELDKWEKIRLRPGGKKQYKLKHIVWASRELERFAVNPGL

LETSEGCRQILGQLQPSLQTGSEELRSLYNTIAVLYCVHQRIDVKDTKEA

LDKIEEEQNKSKKKAQQAAADTGNNSQVSQNYPVQQIGGNYVHLPLSPRT

LNAWVKLIEEKKFGAEVVPGFQALSEGCTPYDINQMLNCVGDHQAAMQII

RDIINEEVADWDLQHPQPAPQQGQLREPSGSDIAGTTSSVDEQIQWMYRQ

QNPIPVGNIYRRWIQLGLQKCVRMYNPTNILDVKQGPKEPFQSYVDRFYK

SLRAEQTDAAVKNWMTQTLLIQNANPDCKLVLKGLGPGATLEEMNITACQ

GVGGPGHKARVLAEAMSQVTNPATIMIQKGNFRNQRKTVKCFNCGKEGHI

AKNCRAPRKKGCWKCGKEGHQMKDCTERQANFLGKIWPSHKGRPGNFLQS

RPEPTAPPEESFRFGEETTTPSQKQEPIDKELYPLASLRSLFGSDPSSQ.
```

In certain embodiments, the nucleotide sequence encoding Pol protein encodes a protein comprising a sequence as set forth as set forth in SEQ ID NO: 10.

```
                                            (SEQ ID NO: 10)
MNLPGRWKPKMIGGIGGFIKVRQYDQILIEICGHKAIGTVLVGPTPVNII

GRNLLTQIGCTLNFPISPIETVPVKLKPGMDGPKVKQWPLTEEKIKALVE

ICTEMEKEGKISKIGPENPYNTPVFAIKKKDSTKWRKLVDFRELNKRTQD

FWEVQLGIPHPAGLKQKKSVTVLDVGDAYFSVPLDKDFRKYTAFTIPSIN

NETPGIRYQYNVLPQGWKGSPAIFQCSMTKILEPFRKQNPDIVIYQYMDD

LYVGSDLEIGQHRTKIEELRQHLLRWGFTTPDKKHQKEPPFLWMGYELHP

DKWTVQPIVLPEKDSWTVNDIQKLVGKLNWASQIYAGIKVRQLCKLLRGT

KALTEVVPLTEEAELELAENREILKEPVHGVYYDPSKDLIAEIQKQGQGQ

WTYQIYQEPFKNLKTGKYARMKGAHTNDVKQLTEAVQKIATESIVIWGKT

PKFKLPIQKETWEAWWTEYWQATWIPEWEFVNTPPLVKLWYQLEKEPIIG

AETFYVDGAANRETKLGKAGYVTDRGRQKVVPLTDTTNQKTELQAIHLAL

QDSGLEVNIVTDSQYALGIIQAQPDKSESELVSQIIEQLIKKEKVYLAWV

PAHKGIGGNEQVDKLVSAGIRKVLFLDGIDKAQEEHEKYHSNWRAMASDF

NLPPVVAKEIVASCDKCQLKGEAMHGQVDCSPGIWQLDCTHLEGKVILVA

VHVASGYIEAEVIPAETGQETAYFLLKLAGRWPVKTVHTDNGSNFTSTTV

KAACWWAGIKQEFGIPYNPQSQGVIESMNKELKKIIGQVRDQAEHLKTAV
```

-continued

```
QMAVFIHNFKRKGGIGGYSAGERIVDIIATDIQTKELQKQITKIQNFRVY

YRDSRDPVWKGPAKLLWKGEGAVVIQDNSDIKVVPRRKAKIIRDYGKQMA

GDDCVASRQDED.
```

By "complete protein or polypeptide" is meant to refer a whole or functional protein or polypeptide. For example, two separate portions of a protein, which would not be functional on their own, can bind together or interact with one another to form a complete protein that is functional. The term should be construed broadly to include any type of protein or polypeptide known in the art. A "complete" protein does not have to have a complete sequence of a particular domain. For example, as provided herein the protein that can be formed by the first and second portion can be a chimeric antigen receptor. In some embodiments, the extracellular domain of the CAR can be an antigen binding domain that binds to an antigen on a target cell. The antigen binding domain can be, for example, a heavy and light chain antibody molecule or can be a scFv domain, but these can differ from a native sequence that would function independently of a CAR.

In certain embodiments, the polypeptide of interest is a chimeric antigen receptor (CAR). The polypeptide of interest can comprise any of the CARs disclosed herein. In certain embodiments, the CAR comprises an extracellular (antigen binding) domain, a transmembrane domain, and an intracellular signaling domain.

In certain embodiments, the extracellular/antigen binding domain is a domain that binds a tumor antigen (e.g. anti-CD19 scFv, anti-CD19 antibody, anti-CD33 scFv, and the like). In some embodiments, polypeptide of interest comprises the transmembrane domain and the CD3 zeta domain. In some embodiments, the CAR comprises an intracellular 4-1BB domain.

In some embodiments, extracellular/antigen binding domain is a domain that binds to CD20, CD22, CD123, CD38, CD19, BCMA, CD33, or CD79b.

In certain embodiments, the first portion of the protein comprises an extracellular/antigen binding domain that binds a tumor antigen (e.g. anti-CD19 scFv, anti-CD19 antibody, anti-CD33 scFv, and the like), and the second portion of the protein comprises a transmembrane domain and a CD3 zeta domain. In certain embodiments, the first portion of the protein comprises an extracellular domain that binds a tumor antigen, and the second portion of the protein comprises a transmembrane domain, a CD3 zeta domain, and a 4-1BB domain. In certain embodiments, the first portion of the protein comprises an extracellular domain that binds a tumor antigen and a transmembrane domain, and the second portion of the protein comprises a CD3 zeta domain. In certain embodiments, the first portion of the protein comprises an extracellular domain that binds a tumor antigen and a transmembrane domain, and the second portion of the protein comprises a CD3 zeta domain and a 4-1BB domain. In certain embodiments, the first portion of the protein comprises an extracellular domain that binds a tumor antigen, a transmembrane domain, and a CD3 zeta domain, and the second portion of the protein comprises and a 4-1BB domain. In certain embodiments, the first portion of the protein comprises an extracellular domain that binds a tumor antigen, a transmembrane domain, and a 4-1BB domain, and the second portion of the protein comprises and a CD3 zeta domain.

In certain embodiments, the polypeptide of interest is a hemoglobin beta chain. These examples of proteins or polypeptides of interest are non-limiting and any polypeptide of interest can be encoded for by the compositions provided for herein.

Viruses

In certain embodiments, the virus particle is an adenovirus. Adenovirus particles are based on adenoviruses, which have a low capacity for integration into genomic DNA but a high efficiency for transfecting host cells. Adenovirus particles contain adenovirus sequences sufficient to: (a) support packaging of the expression vector and (b) to ultimately express the protein in the host cell. In some embodiments, the adenovirus genome is a 36 kb, linear, double stranded DNA, where a foreign DNA sequence (e.g., a nucleic acid encoding a CAR) may be inserted to substitute large pieces of adenoviral DNA in order to make the expression vector (see, e.g., Danthinne and Imperiale, Gene Therapy (2000) 7(20): 1707-1714).

In certain embodiments, the virus particle is a dependovirus, such as a parvovirus. A non-limiting example of a dependovirus is the adeno associated virus (AAV), which takes advantage of the adenovirus coupled systems. This AAV expression vector has a high frequency of integration into the host genome. It can infect nondividing cells, thus making it useful for delivery of genes into mammalian cells, for example, in tissue cultures or in vivo. The AAV has a broad host range for infectivity. Details concerning the generation and use of AAV are described in U.S. Pat. Nos. 5,139,941 and 4,797,368, each of which is incorporated by reference in its entirety. In some embodiments, the AAV particle is an AAV9 particle. An example of a AAV9 particle is provided in U.S. Pat. No. 7,906,111, which is hereby incorporated by reference in its entirety.

Retrovirus expression vectors are capable of integrating into the host genome, delivering a large amount of foreign genetic material, infecting a broad spectrum of species and cell types and being packaged in special cell lines. The retroviral particle is constructed by inserting a nucleic acid (e.g., a nucleic acid encoding a CAR) into the viral genome at certain locations to produce a virus that is replication defective. Though the retroviral particles are able to infect a broad variety of cell types, integration and stable expression of the CAR requires the division of host cells.

In certain embodiments, the virus particle is a lentiviral particle. Lentiviral particles are derived from lentiviruses, which are retroviruses that, in addition to the common retroviral genes gag, pol, and env, contain other genes with regulatory or structural function (see, e.g., U.S. Pat. Nos. 6,013,516 and 5,994,136). Some examples of lentiviruses include the Human Immunodeficiency Viruses (HIV-1, HIV-2) and the Simian Immunodeficiency Virus (SIV). Lentiviral particles have been generated by multiply attenuating the HIV virulence genes, for example, the genes env, vif, vpr, vpu and nef are deleted making the vector biologically safe. Lentiviral particles are capable of infecting non-dividing cells and can be used for both in vivo and ex vivo gene transfer and expression, e.g., of a nucleic acid encoding a CAR (see, e.g., U.S. Pat. No. 5,994,136).

Pseudotyped Viral Particles Targeting Moiety

To confer specificity of the viral particles to target cells, viral particles can be pseudotyped. Capsid proteins and envelope glycoproteins are implicated in virus attachment and interactions with cellular receptors, determining cell tropism. Manipulation of these viral surface proteins therefore may improve the transduction capacity of these vectors, expanding or restricting their tropism. Furthermore, experiments with vector pseudotyping demonstrated that pseudotyped vectors could achieve higher transduction titers and increase transduction efficacy.

In some embodiments, a virus particle comprising a targeting moiety that binds to a target on a cell and a nucleic acid molecule that encodes a polypeptide of interest is provided.

In some embodiments, a virus particle comprising a first targeting moiety that binds to a first target on a cell and a nucleic acid molecule that encodes a first portion of a protein or polypeptide are provided. In some embodiments, a virus particle comprising a second targeting moiety that binds to a second target on the cell and a nucleic acid molecule that encodes for a second portion of the protein or the polypeptide are provided.

In some embodiments, a composition comprising a first viral particle having a first targeting moiety that binds to a first target on a cell, and a second viral particle having a second targeting moiety that binds to a second target on the cell are provided. In certain embodiments, the first target and the second target are different.

The targeting moiety can be any type of targeting moeity, including but not limited to, an antigen binding domain, a DARPIN, a FN3 domain, an antibody, a Centryn, Stem Cell Factor protein (SCF, KIT-ligand, KL, or steel factor). In certain embodiments, the target is cKit (CD117), CD4, CD8, CD3, CD5, CD6, CD7, CD2, TCR alpha, TCR beta, TCR gamma, TCR delta, CD10, CD34, CD110, CD33, CD14, CD68, CCR7, CD62L, CD25, CCR2, CCR3, CCR4, CCR5, CCR6, CCR7, and CXCR3. In certain embodiments, the target is cKit (CD117), CD4, CD8, CD3, CD5, CD6, CD7, CD2, TCR alpha, TCR beta, TCR gamma, TCR delta, CD10, CD34, CD110, CD33, CD14, or CD68.

In certain embodiments, the first target and the second target are each independently selected from the group consisting of cKit (CD117), CD4, CD8, CD3, CD5, CD6, CD7, CD2, TCR alpha, TCR beta, TCR gamma, TCR delta, CD10, CD34, CD110, CD33, CD14, CD68, CCR7, CD62L, CD25, CCR2, CCR3, CCR4, CCR5, CCR6, CCR7, and CXCR3. In certain embodiments, the first target is cKit (CD117), CD4, CD8, CD3, CD5, CD6, CD7, CD2, TCR alpha, TCR beta, TCR gamma, TCR delta, CD10, CD34, CD110, CD33, CD14, or CD68. In certain embodiments, the second target is CCR7, CD62L, CD25, CCR2, CCR3, CCR4, CCR5, CCR6, CCR7, or CXCR3.

In certain embodiments, the targeting moiety (first and/or second) is a protein that binds to a target, an antigen binding domain, an antibody, a scFv, a DARPIN, and a FN3 domain, or any combination thereof.

In certain embodiments, the targeting moiety (first and/or second) is Stem Cell Factor protein (SCF, KIT-ligand, KL, or steel factor) or a moiety that binds to cKit (CD117), CD4, CD8, CD3, CD5, CD6, CD7, CD2, TCR alpha, TCR beta, TCR gamma, TCR delta, CD10, CD34, CD110, CD33, CD14, CD68, CCR7, CD62L, CD25, CCR2, CCR3, CCR4, CCR5, CCR6, CCR7, or CXCR3. In some embodiments, the targeting moiety binds to CD4 and/or CD8. In some embodiments, the targeting moiety binds to CD20, CD22, CD123, CD38, CD19, BCMA, CD33, or CD79b.

In certain embodiments, the engineered virus particle is a pseudotyped virus particle. In certain embodiments, the engineered virus particle is a pseudotyped lentiviral virus particle, an adenovirus, or an adeno-associated virus. In certain embodiments, the pseudotyped lentiviral virus particle is pseudotyped with a morbillivirus, such as a measles virus, glycoprotein and/or a Nipah virus glycoprotein. In certain embodiments, the engineered virus particle is pseudotyped with a F protein or H protein of a morbillivirus. In some embodiments, the measles F protein or H protein is mutated. The mutations can be used in subjects that have been exposed to the measles virus or measles vaccine, which can avoid neutralization by anti-MV antibodies that may be present in those that have been exposed to the measles virus or the measles vaccine. In some embodiments, the engineered virus particle is pseudotyped with a F protein or G protein of a Nipah virus.

Examples of the F, G, or H proteins can be found in U.S. Pat. No. 10,415,057, which is hereby incorporated by reference in its entirety. In some embodiments, the pseudotyped viral particle comprises a fusion (F) and a hemagglutinin (H) protein of a morbillivirus, wherein the cytoplasmic portions of said F and H proteins are truncated and wherein the truncated cytoplasmic portion of the F protein comprises at least 1 positively charged amino acid residue and the truncated cytoplasmic portion of the H protein is truncated to allow efficient pseudotyping and has fusion support function. In some embodiments, the morbillivirus is a measles virus, or the Edmonston strain of measles virus. In some embodiments, the truncated cytoplasmic portion of the H protein comprises at least 9 consecutive amino acid residues of the C-terminal cytoplasmic portion of the H protein plus an additional methinonine at the N-terminus. In some embodiments, the truncated cytoplasmic portion of the F protein comprises at least 3 consecutive amino acid residues of the N-terminal cytoplasmic portion of the F protein and the truncated cytoplasmic portion of the H protein comprises at least 13 consecutive amino acid residues of the C-terminal cytoplasmic portion of the H protein plus an additional methinonine at the N-terminus, wherein one to four of the N-terminal amino acid residues of said at least 13 consecutive amino acid residues of the C-terminal cytoplasmic portion of the H protein can be replaced by alanine residues. In some embodiments, the truncated F protein is FcΔ24 or FcΔ30 and/or the truncated H protein is selected from the group consisting of HcΔ14, HcΔ15, HcΔ16, HcΔ17, HcΔ18, Hc.DELTA. 19, HcΔ20, HcΔ21+A and HcΔ24+4A. These proteins are also described in U.S. Pat. No. 10,415,057, which is hereby incorporated by reference in its entirety.

In some embodiments, the viral particle comprises a measles virus F protein, which can be referred to as Δ30, having an amino acid sequence of:

(SEQ ID NO: 11)

```
MGLKVNVSAIFMAVLLTLQTPTGQIHWGNLSKIGVVGIGSASYKVMTRSS
HQSLVIKLMPNITLLNNCTRVEIAEYRRLLRTVLEPIRDALNAMTQNIRP
VQSVASSRRHKRFAGVVLAGAALGVATAAQITAGIALHQSMLNSQAIDNL
RASLETTNQAIEAIRQAGQEMILAVQGVQDYINNELIPSMNQLSCDLIGQ
KLGLKLLRYYTEILSLFGPSLRDPISAEISIQALSYALGGDINKVLEKLG
```

-continued

```
YSGGDLLGILESRGIKARITHVDTESYLIVLSIAYPTLSEIKGVIVHRLE
GVSYNIGSQEWYTTVPKYVATQGYLISNFDESSCTFMPEGTVCSQNALYP
MSPLLQECLRGSTKSCARTLVSGSFGNRFILSQGNLIANCASILCKCYTT
GTIINQDPDKILTYIAADHCPVVEVNGVTIQVGSRRYPDAVYLHRIDLGP
PILLERLDVGTNLGNAIAKLEDAKELLESSDQILRSMKGLSSTCIVYILI
AVCLGGLIGIPALICCCRGR.
```

In some embodiments, the viral particle comprises a measles virus H protein, which can be referred to as Δ18+4A, having an amino acid sequence of:

(SEQ ID NO: 12)

```
MGSRIVINREHLMIDRPYVLLAVLFVMFLSLIGLLAIAGIRLHRAAIYTA
EIHKSLSTNLDVTNSIEHQVKDVLTPLFKIIGDEVGLRTPQRFTDLVKFI
SDKIKFLNPDREYDFRDLTWCINPPERIKLDYDQYCADVAAEELMNALVN
STLLETRTTNQFLAVSKGNCSGPTTIRGQFSNMSLSLLDLYLGRGYNVSS
IVTMTSQGMYGGTYLVEKPNLSSKRSELSQLSMYRVFEVGVIRNPGLGAP
VFHMTNYLEQPVSNDLSNCMVALGELKLAALCHGEDSITIPYQGSGKGVS
FQLVKLGVWKSPTDMQSWVPLSTDDPVIDRLYLSSHRGVIADNQAKWAVP
TTRTDDKLRMETCFQQACKGKIQALCENPEWAPLKDNRIPSYGVLSVDLS
LTVELKIKIASGFGPLITHGSGMDLYKSNHNNVYWLTIPPMKNLALGVIN
TLEWIPRFKVSPALFNVPIKEAGEDCHAPTYLPAEVDGDVKLSSNLVILP
GQDLQYVLATYDTSAVEHAVVYYVYSPSRLSSYFYPFRLPIKGVPIELQV
ECFTWDQKLWCRHFCVLADSESGGHITHSGMVGMGVSCTVTREDGTNRRG
G.
```

Without being bound to any theory, the 4 amino acid changes are used to inactivate the natural tropism for CD46.

In some embodiments, the viral particle comprises the measles Δ30 (SEQ ID NO: 11) and the measles Δ18+4A (SEQ ID NO: 12) amino acid sequences.

In some embodiments, the viral particle comprises a Nipah virus F protein, which can be referred to as Δ30, having the amino acid sequence of:

(SEQ ID NO: 13)

```
MVVILDKRCYCNLLILILMISECSVGILHYEKLSKIGLVKGVTRKYKIKS
NPLTKDIVIKMIPNVSNMSQCTGSVMENYKTRLNGILTPIKGALEIYKNN
THDLVGDVRLAGVIMAGVAIGIATAAQITAGVALYEAMKNADNINKLKSS
IESTNEAVVKLQETAEKTVYVLTALQDYINTNLVPTIDKISCKQTELSLD
LALSKYLSDLLFVFGPNLQDPVSNSMTIQAISQAFGGNYETLLRTLGYAT
EDFDDLLESDSITGQIIYVDLSSYYIIVRVYFPILTEIQQAYIQELLPVS
FNNDNSEWISIVPNFILVRNTLISNIEIGFCLITKRSVICNQDYATPMTN
NMRECLTGSTEKCPRELVVSSHVPRFALSNGVLFANCISVTCQCQTTGRA
ISQSGEQTLLMIDNTTCPTAVLGNVIISLGKYLGSVNYNSEGIAIGPPVF
TDKVDISSQISSMNQSLQQSKDYIKEAQRLLDTVNPSLISMLSMIILYVL
SIASLCIGLITFISFIIVEKKRNT.
```

In some embodiments, the viral particle comprises a Nipah virus G protein, which can be referred to as Δ34+4A, having the amino acid sequence of:

(SEQ ID NO: 14)

MKKINEGLLDSKILSAFNTVIALLGSIVIIVMNIMIIQNYTRSTDNQAVI

KDALQGIQQQIKGLADKIGTEIGPKVSLIDTSSTITIPANIGLLGSKISQ

STASINENVNEKCKFTLPPLKIHECNISCPNPLPFREYRPQTEGVSNLVG

LPNNICLQKTSNQILKPKLISYTLPVVGQSGTCITDPLLAMDEGYFAYSH

LERIGSCSRGVSKQRIIGVGEVLDRGDEVPSLFMTNVWTPPNPNTVYHCS

AVYNNEFYYVLCAVSTVGDPILNSTYWSGSLMMTRLAVKPKSNGGGYNQH

QLALRSIEKGRYDKVMPYGPSGIKQGDTLYFPAVGFLVRTEFKYNDSNCP

ITKCQYSKPENCRLSMGIRPNSHYILRSGLLKYNLSDGENPKVVFIEISD

QRLSIGSPSKIYDSLGQPVFYQASFSWDTMIKFGDVLTVNPLVVNWRNNT

VISRPGQSQCPRFNTCPAICAEGVYNDAFLIDRINWISAGVFLDSNATAA

NPVFTVFKDNEILYRAQLASEDTNAQKTITNCFLLKNKIWCISLVEIYDT

GDNVIRPKLFAVKIPEQCT.

Without being bound to any theory, the 4 amino acid changes are used to inactivate the natural tropism for Ephrin.

In some embodiments, the viral particle comprises the Nipah 430 (SEQ ID NO: 13) and the Nipah Δ18+4A (SEQ ID NO: 14) amino acid sequences.

In some embodiments, the H protein is a fusion of HmutΔ18, HmutΔ19 or HmutΔ24+4A and a single chain antibody or a ligand to a cell surface marker at its ectodomain. In some embodiments, the single chain antibody is directed against the cell surface proteins as provided herein, including but not limited to, CD20 (scFvCD20), CD34 (scFvCD34), VEGFR-2 (scFvA7), CD133 (scFvCD133), or the ligand is EGF (the ligand of the EGF-receptor). In some embodiments, the H protein is a fusion of HmutΔ18, HmutΔ19 or HmutΔ24+4A fused to scFvCD20, scFvCD34, scFvA7, EGF or scFvCD133 and the F protein is FcΔ30 or FcΔ24. In some embodiments the truncated H protein is a fusion defined by the amino acid sequence set forth in SEQ ID NO: 2 or SEQ ID NO: 4 of U.S. Pat. No. 10,415,057, which is hereby incorporated by reference in its entirety i.e., SEQ ID NOs: 15 and 16 of the present disclosure, respectively:

(SEQ ID NO: 15)

MGSRIVINREHLMIDRPYVLLAVLFVMFLSLIGLLAIAGIRLHRAAIYTA

EIHKSLSTNLDVTNSIEHQVKDVLTPLFKIIGDEVGLRTPQRFTDLVKFI

SDKIKFLNPDREYDFRDLTWCINPPERIKLDYDQYCADVAAEELMNALVN

STLLETRTTNQFLAVSKGNCSGPTTIRGQFSNMSLSLLDLYLGRGYNVSS

IVTMTSQGMYGGTYLVEKPNLSSKRSELSQLSMYRVFEVGVIRNPGLGAP

VFHMTNYLEQPVSNDLSNCMVALGELKLAALCHGEDSITIPYQGSGKGVS

FQLVKLGVWKSPTDMQSWVPLSTDDPVIDRLYLSSHRGVIADNQAKWAVP

TTRTDDKLRMETCFQQACKGKIQALCENPEWAPLKDNRIPSYGVLSVDLS

LTVELKIKIASGFGPLITHGSGMDLYKSNHNNVYWLTIPPMKNLALGVIN

TLEWIPRFKVSPALFTVPIKEAGGDCHAPTYLPAEVDGDVKLSSNLVILP

-continued

GQDLQYVLATYDTSAVEHAVVYYVYSPSRLSSYFYPFRLPIKGVPIELQV

ECFTWDQKLWCRHFCVLADSESGGHITHSGMVGMGVSCTVTREDGTNAAQ

PAIEGRMAQVQLVQSGAELVKPGASVKMSCKASGYTFTSYNMHWVKQTPG

QGLEWIGAIYPGNGDTSYNQKFKGKATLTADKSSSTAYMQLSSLTSEDSA

VYYCARAQLRPNYWYFDVWGAGTTVTVSKISGGGGSGGGGSGGGGSGGSS

DIVLSQSPAILSASPGEKVTMTCRASSSVSYMHWYQQKPGSSPKPWIYAT

SNLASGVPARFSGSGSGTSYSLTISRVEAEDAATYYCQQWISNPPTFGAG

TKLELKAAARGSHHHHHH.

(SEQ ID NO: 16)

MGSRIVINREHLMIDRPYVLLAVLFVMFLSLIGLLAIAGIRLHRAAIYTA

EIHKSLSTNLDVTNSIEHQVKDVLTPLFKIIGDEVGLRTPQRFTDLVKFI

SDKIKFLNPDREYDFRDLTWCINPPERIKLDYDQYCADVAAEELMNALVN

STLLETRTTNQFLAVSKGNCSGPTTIRGQFSNMSLSLLDLYLGRGYNVSS

IVTMTSQGMYGGTYLVEKPNLSSKRSELSQLSMYRVFEVGVIRNPGLGAP

VFHMTNYLEQPVSNDLSNCMVALGELKLAALCHGEDSITIPYQGSGKGVS

FQLVKLGVWKSPTDMQSWVPLSTDDPVIDRLYLSSHRGVIADNQAKWAVP

TTRTDDKLRMETCFQQACKGKIQALCENPEWAPLKDNRIPSYGVLSVDLS

LTVELKIKIASGFGPLITHGSGMDLYKSNHNNVYWLTIPPMKNLALGVIN

TLEWIPRFKVSPALFTVPIKEAGGDCHAPTYLPAEVDGDVKLSSNLVILP

GQDLQYVLATYDTSAVEHAVVYYVYSPSRLSSYFYPFRLPIKGVPIELQV

ECFTWDQKLWCRHFCVLADSESGGHITHSGMVGMGVSCTVTREDGTNAAQ

PAMANSDSECPLSHDGYCLHDGVCMYIEALDKYACNCVVGYIGERCQYRD

LKWWELRAAARGSHHHHHH.

In some embodiments, the first virus particle and the second virus particle are pseudotyped with the same envelope protein. In some embodiments, the first viral vector and the second virus particle are pseudotyped with different envelope proteins. In some embodiments, the compositions provided herein comprise an engineered virus particle comprising targeting moieties that bind a cell. In some embodiments, the compositions provided herein comprise a first and second virus particle comprising targeting moieties that bind a first and second target on a cell. The cell can be any type of cell including, but not limited to, a T cell, a CD4+ T cell, a CD8+ T cell, a NK cell, an alpha-beta T cell, a gamma-delta T cell, a lymphoid progenitor cell, a hematopoietic stem cell, a myeloid cell, a monocyte, a macrophage, a central memory T cell, a naïve T cell, an activated T cell, a regulatory T Cell (Treg), or a T-Cell$^{CD8\text{-}CCR7-}$. In some embodiments, the cell is a CD4+ CD8+ T cell.

Accordingly, in some embodiments an engineered viral particle is provided comprising an engineered envelope comprising a polypeptide having the amino acid sequence of SEQ ID NO: 9. In some embodiments, the engineered viral particle comprises a heterologous polypeptide targeting moiety for binding to a target cell. In some embodiments, the viral particle comprises a nucleic acid molecule encoding a heterologous polypeptide of interest. In some embodiments, the targeting moiety is fused to a mutated fusion protein present on the surface of the engineered viral particle. In some embodiments, the viral particle is a lentivirus pseudotyped with a) a measles virus (MV) hemagglutinin (HA) protein and/or an MV fusion (F) protein (MV-F protein) and wherein the MV-HA protein or the MV-F protein comprises a mutation or a mutated binding domain compared to its naturally occurring protein; or b) a Nipah virus F protein and/or a Nipah virus G protein and wherein the Nipah virus F protein and/or a Nipah virus G protein comprises a mutation or a mutated binding domain compared to its naturally occurring protein. In some embodiments, the targeting moiety is fused to the MV-HA protein and/or the MV-F protein. In some embodiments, the targeting moiety is fused to the Nipah virus F protein and/or a Nipah virus G protein. In some embodiments, the targeting moiety is a scFv, an antigen binding domain, a DARPIN, a VHH, or a FN3 domain. In some embodiments, the targeting moiety binds to protein selected from the group consisting of Stem Cell Factor protein (SCF, KIT-ligand, KL, or steel factor) or a moiety that binds to cKit (CD1 17), CD4, CD8, CD3, CD3D, CD3E, CD3G, CD3Z, CD5, CD6, CD7, CD2, TCR alpha, TCR beta, TCR gamma, TCR delta, CD10, CD34, CD110, CD33, CD14, CD68, CCR7, CD62L, CD25, CCR2, CCR3, CCR4, CCR5, CCR6, CCR7, and CXCR3. In some embodiments, the heterologous polypeptide of interest is a chimeric antigen receptor (CAR). In some embodiments, the chimeric antigen receptor comprises an extracellular domain, transmembrane domain, and an intracellular signaling domain. In some embodiments, the extracellular domain binds to CD20, CD22, CD123, CD38, CD19, BCMA, CD33, or CD79b. In some embodiments, the heterologous polypeptide of interest is a hemoglobin beta chain.

Cells

In some embodiments, the embodiments provided include a cell comprising the engineered virus particle or particles as provided herein. In some embodiments, the cell comprises the polypeptide of interest encoded by the engineered virus particle.

In certain embodiments, the polypeptide of interest is a hemoglobin beta chain. In certain embodiments, the polypeptide of interest is a heterologous chimeric antigen receptor (CAR).

In certain embodiments, the cell is a T cell, e.g., a CD8+ T cell (e.g., a CD8+ naive T cell, central memory T cell, or effector memory T cell), a CD4+ T cell, a natural killer T cell (NKT cells), a regulatory T cell (Treg), an alpha-beta T cell, a gamma-delta T cell, a stem cell memory T cell, a central memory T cell, a naïve T cell, an activated T cell, a T-Cell$^{CD8-CCR7+}$, a lymphoid progenitor cell, a hematopoietic stem cell, a natural killer cell (NK cell), or a dendritic cell. In some embodiments, the cells are monocytes or granulocytes, e.g., myeloid cells, macrophages, neutrophils, dendritic cells, mast cells, eosinophils, and/or basophils. In an embodiment, the target cell is an induced pluripotent stem (iPS) cell or a cell derived from an iPS cell, e.g., an iPS cell generated from a subject, manipulated to alter (e.g., induce a mutation in) or manipulate the expression of one or more target genes, and differentiated into, e.g., a T cell, e.g., a CD8+ T cell (e.g., a CD8+ naive T cell, central memory T cell, or effector memory T cell), a CD4+ T cell, a stem cell memory T cell, a lymphoid progenitor cell or a hematopoietic stem cell. In some embodiments, the cell is a CD4+ CD8+ T cell.

In some embodiments, the cells include one or more subsets of T cells or other cell types, such as whole T cell populations, CD4+ cells, CD8+ cells, and subpopulations thereof, such as those defined by function, activation state, maturity, potential for differentiation, expansion, recirculation, localization, and/or persistence capacities, antigen-specificity, type of antigen receptor, presence in a particular organ or compartment, marker or cytokine secretion profile, and/or degree of differentiation. Among the sub-types and subpopulations of T cells and/or of CD4+ and/or of CD8+ T cells are naive T (TN) cells, effector T cells (TEFF), memory T cells and sub-types thereof, such as stem cell memory T (TSCM), central memory T (TCM), effector memory T (TEM), or terminally differentiated effector memory T cells, tumor-infiltrating lymphocytes (TIL), immature T cells, mature T cells, helper T cells, cytotoxic T cells, mucosa-associated invariant T (MAIT) cells, naturally occurring and adaptive regulatory T (Treg) cells, helper T cells, such as TH1 cells, TH2 cells, TH3 cells, TH17 cells, TH9 cells, TH22 cells, follicular helper T cells, alpha/beta T cells, and delta/gamma T cells. In certain embodiments, any number of T cell lines available in the art, may be used.

Viral Vector

Provided herein are compositions that can be used, for example, to selectively transduce a cell expressing specific cell surface markers in vivo using a viral vector. In some embodiments, the vector encodes the polypeptide of interest. In some embodiments, the viral vector is a pseudotyped vector.

In some embodiments, the pseudotyped viral vector comprises a chimeric gag protein, as described herein. In some embodiments, the chimeric gag protein is referred to as xHIV gag protein. In some embodiments, the gag protein comprises the sequence as set forth in SEQ ID NO: 9. In some embodiments, the viral vector comprises a polynucleotide molecule encoding the chimeric gag protein. In some embodiments, the polynucleotide molecule encoding the chimeric gag protein comprises a sequence of SEQ ID NO: 5 or SEQ ID NO: 6. In some embodiments, the nucleotide sequence further comprises a long-terminal repeat (LTR), a SIV element, a sequence encoding a Pol protein, and/or a sequence encoding an Envelope (Env) polyprotein. In some embodiments, the gag protein, the SIV element, and the Pol protein of the xHIV are encoded by the nucleic acid sequence as set forth in SEQ ID NO: 5. In some embodiments, the gag protein is encoded by the nucleic acid sequence as set forth in SEQ ID NO: 6. In some embodiments, the SIV element is encoded by the nucleic acid sequence as set forth in SEQ ID NO: 7. In some embodiments, the nucleic acid sequence encoding the SIV element is located within the nucleic acid sequence encoding the gag protein as set forth in SEQ ID NO: 6. In some embodiments, the Pol protein is encoded by the nucleic acid sequence as set forth in SEQ ID NO: 8. In some embodiments, the polynucleic acid molecule encoding the Pol protein encodes for a protein comprising the sequence as set forth in SEQ ID NO: 10.

In some embodiments, a viral particle is provided comprising a chimeric gag protein, as described herein. In some embodiments, the chimeric gag protein comprises an amino acid sequence as set forth in SEQ ID NO: 9. In some embodiments, a viral particle comprising the chimeric gag protein comprises a heterologous transgene of interest, such as a chimeric antigen receptor. Non-limiting examples of chimeric antigen receptors are provided herein.

Also provided herein are compositions that can be used, for example, to selectively transduce a cell expressing specific cell surface markers in vivo using a plurality of viral vectors, which can be referred to as a split viral vector system. In some embodiments, one vector encodes a first portion of the molecule of interest, and another vector encodes a second portion of the molecule of interest. In certain embodiments, a first portion and a second portion of a protein (or nucleic acids encoding said proteins) are expressed by, or encoded by a plurality of vectors. In some embodiments, the first portion and the second portion are expressed by, or encoded by, 2, 3, or 4 different vectors. For the avoidance of doubt, the vectors are considered different if they encode for different portions that have different sequences or the molecule of interest, even if the molecule's sequence or structure are similar or overlap.

In some embodiments, one viral particle provides a viral vector encoding a first portion of a molecule of interest, and another viral particle provides a second viral vector encoding a second portion of a molecule of interest. As provided herein, in some embodiments, a molecule of interest is a chimeric antigen receptor.

In some embodiments, a composition comprising a first viral particle and a second viral particle are provided. In some embodiments, the first viral particle comprises a first targeting moiety that binds to a first target on a cell and a nucleic acid molecule that encodes a first portion of a protein or polypeptide. In some embodiments, the second viral particle comprises a second targeting moiety that binds to a second target on the cell and a nucleic acid molecule that encodes a second portion of the protein or the polypeptide. Once expressed in the cell, the first and second portions of the protein or the polypeptide can bind together or interact with one another to form a complete or functional protein or polypeptide.

Expression vectors comprising a nucleic acid of the present disclosure can be introduced into a host cell by any method or composition known to persons skilled in the art. The expression vectors may include viral sequences for transfection, if desired. Alternatively, the expression vectors may be introduced by fusion, electroporation, biolistics, transfection, lipofection, or the like. Although the cell can be transduced or transfected in vivo, in some embodiments, the transduced cells can then be isolated from the subject and then, in some embodiments, may be grown and expanded in culture ex vivo. The expanded cells can then be screened by virtue of a marker present in the vectors. The expanded cells can then be reintroduced into the same subject or a different subject for treatment. Various markers that may be used are known in the art, and may include hprt, neomycin resistance, thymidine kinase, hygromycin resistance, etc. In some embodiments, the host cell is an immune cell or precursor thereof, e.g., a T cell, an NK cell, or an NKT cell.

Embodiments provided herein also include nucleic acids encoding any of the virus particles, in any of the embodiments, disclosed herein.

In some embodiments, a nucleic acid of the present disclosure is provided for the production of a protein (e.g. CAR) as described herein, e.g., in a cell or in a subject in vivo.

In some embodiments, a nucleic acid of the present disclosure may be operably linked to a transcriptional control element, e.g., a promoter, and enhancer, etc. Suitable promoter and enhancer elements are known to those of skill in the art. In certain embodiments, the nucleic acid encoding a CAR is in operable linkage with a promoter. In certain embodiments, the promoter is a phosphoglycerate kinase-1 (PGK) promoter.

For expression in a eukaryotic cell, suitable promoters include, but are not limited to, light and/or heavy chain immunoglobulin gene promoter and enhancer elements; cytomegalovirus immediate early promoter; herpes simplex virus thymidine kinase promoter; early and late SV40 promoters; promoter present in long terminal repeats from a retrovirus; mouse metallothionein-I promoter; and various art-known tissue specific promoters. Suitable reversible promoters, including reversible inducible promoters are known in the art. Such reversible promoters may be isolated and derived from many organisms, e.g., eukaryotes and prokaryotes. Modification of reversible promoters derived from a first organism for use in a second organism, e.g., a first prokaryote and a second a eukaryote, a first eukaryote and a second a prokaryote, etc., is well known in the art. Such reversible promoters, and systems based on such reversible promoters but also comprising additional control proteins, include, but are not limited to, alcohol regulated promoters (e.g., alcohol dehydrogenase I (alcA) gene promoter, promoters responsive to alcohol transactivator proteins (AlcR), etc.), tetracycline regulated promoters, (e.g., promoter systems including TetActivators, TetON, TetOFF, etc.), steroid regulated promoters (e.g., rat glucocorticoid receptor promoter systems, human estrogen receptor promoter systems, retinoid promoter systems, thyroid promoter systems, ecdysone promoter systems, mifepristone promoter systems, etc.), metal regulated promoters (e.g., metallothionein promoter systems, etc.), pathogenesis-related regulated promoters (e.g., salicylic acid regulated promoters, ethylene regulated promoters, benzothiadiazole regulated promoters, etc.), temperature regulated promoters (e.g., heat shock inducible promoters (e.g., HSP-70, HSP-90, soybean heat shock promoter, etc.), light regulated promoters, synthetic inducible promoters, and the like.

In some embodiments, the promoter is a CD8 cell-specific promoter, a CD4 cell-specific promoter, a neutrophil-specific promoter, or an NK-specific promoter. For example, a CD4 gene promoter can be used; see, e.g., Salmon et al. Proc. Natl. Acad. Sci. USA (1993) 90:7739; and Marodon et al. (2003) Blood 101:3416. As another example, a CD8 gene promoter can be used. NK cell-specific expression can be achieved by use of an NcrI (p46) promoter; see, e.g., Eckelhart et al. Blood (2011) 117:1565.

Other examples of suitable promoters include the immediate early cytomegalovirus (CMV) promoter sequence. This promoter sequence is a strong constitutive promoter sequence capable of driving high levels of expression of any polynucleotide sequence operatively linked thereto. Other constitutive promoter sequences may also be used, including, but not limited to a simian virus 40 (SV40) early promoter, a mouse mammary tumor virus (MMTV) or human immunodeficiency virus (HIV) long terminal repeat (LTR) promoter, a MoMuL V promoter, an avian leukemia virus promoter, an Epstein-Barr virus immediate early promoter, a Rous sarcoma virus promoter, the EF-1 alpha promoter, as well as human gene promoters such as, but not limited to, an actin promoter, a myosin promoter, a hemoglobin promoter, and a creatine kinase promoter. Further, the vectors should not be limited to the use of constitutive promoters. Inducible promoters can also be used. The use of an inducible promoter provides a molecular switch capable of turning on expression of the polynucleotide sequence which it is operatively linked when such expression is desired, or turning off the expression when expression is not desired. Examples of inducible promoters include, but are not limited to a metallothionine promoter, a glucocorticoid promoter, a progesterone promoter, and a tetracycline promoter.

In some embodiments, the locus or construct or transgene containing the suitable promoter is irreversibly switched through the induction of an inducible system. Suitable systems for induction of an irreversible switch are well known in the art, e.g., induction of an irreversible switch may make use of a Cre-lox-mediated recombination (see, e.g., Fuhrmann-Benzakein, et al., Proc. Natl. Acad. Sci. USA (2000) 28:e99, the disclosure of which is incorporated herein by reference). Any suitable combination of recombinase, endonuclease, ligase, recombination sites, etc. known to the art may be used in generating an irreversibly switchable promoter. Methods, mechanisms, and requirements for performing site-specific recombination, described elsewhere herein, find use in generating irreversibly switched promoters and are well known in the art, see, e.g., Grindley et al. Annual Review of Biochemistry (2006) 567-605; and Tropp, Molecular Biology (2012) (Jones & Bartlett Publishers, Sudbury, Mass.), the disclosures of which are incorporated herein by reference.

A nucleic acid of the present disclosure may be present within an expression vector and/or a cloning vector. An expression vector can include a selectable marker, an origin of replication, and other features that provide for replication and/or maintenance of the vector. Suitable expression vectors include, e.g., plasmids, viral vectors, and the like. Large numbers of suitable vectors and promoters are known to those of skill in the art; many are commercially available for generating a subject recombinant construct. The following vectors are provided by way of example, and should not be construed in anyway as limiting: Bacterial: pBs, phagescript, PsiX174, pBluescript SK, pBs KS, pNH8a, pNH16a, pNH18a, pNH46a (Stratagene, La Jolla, Calif., USA); pTrc99A, pKK223-3, pKK233-3, pDR540, and pRIT5 (Pharmacia, Uppsala, Sweden). Eukaryotic: pWLneo, pSV2cat, pOG44, PXR1, pSG (Stratagene) pSVK3, pBPV, pMSG and pSVL (Pharmacia).

Expression vectors generally have convenient restriction sites located near the promoter sequence to provide for the insertion of nucleic acid sequences encoding heterologous proteins. A selectable marker operative in the expression host may be present. Suitable expression vectors include, but are not limited to, viral vectors (e.g. viral vectors based on vaccinia virus; poliovirus; adenovirus (see, e.g., Li et al., Invest. Opthalmol. Vis. Sci. (1994) 35: 2543-2549; Borras et al., Gene Ther. (1999) 6: 515-524; Li and Davidson, Proc. Natl. Acad. Sci. USA (1995) 92: 7700-7704; Sakamoto et al., H. Gene Ther. (1999) 5: 1088-1097; WO 94/12649, WO 93/03769; WO 93/19191; WO 94/28938; WO 95/11984 and WO 95/00655); adeno-associated virus (see, e.g., Ali et al., Hum. Gene Ther. (1998) 9: 81-86, Flannery et al., Proc. Natl. Acad. Sci. USA (1997) 94: 6916-6921; Bennett et al., Invest. Opthalmol. Vis. Sci. (1997) 38: 2857-2863; Jomary et al., Gene Ther. (1997) 4:683 690, Rolling et al., Hum. Gene Ther. (1999) 10: 641-648; Ali et al., Hum. Mol. Genet. (1996) 5: 591-594; Srivastava in WO 93/09239, Samulski et al., J. Vir. (1989) 63: 3822-3828; Mendelson et al., Virol. (1988) 166: 154-165; and Flotte et al., Proc. Natl. Acad. Sci. USA (1993) 90: 10613-10617); SV40; herpes simplex virus; human immunodeficiency virus (see, e.g., Miyoshi et al., Proc. Natl. Acad. Sci. USA (1997) 94: 10319-23; Takahashi et al., J. Virol. (1999) 73: 7812-7816); a retroviral vector (e.g., Murine Leukemia Virus, spleen necrosis virus, and vectors derived from retroviruses such as Rous Sarcoma Virus, Harvey Sarcoma Virus, avian leukosis virus, human immunodeficiency virus, myeloproliferative sarcoma virus, and mammary tumor virus); and the like.

Additional expression vectors suitable for use are, e.g., without limitation, a lentivirus vector, a gamma retrovirus vector, a foamy virus vector, an adeno-associated virus vector, an adenovirus vector, a pox virus vector, a herpes virus vector, an engineered hybrid virus vector, a transposon mediated vector, and the like. Viruses, which are useful as vectors include, but are not limited to, retroviruses, adenoviruses, adeno-associated viruses, herpes viruses, and lentiviruses.

In some embodiments, an expression vector (e.g., a lentiviral vector) may be used to introduce the polypeptide of interest (e.g., CAR, or a portion thereof) into a cell (e.g., a T cell). Accordingly, an expression vector (e.g., a lentiviral vector) may comprise a nucleic acid encoding for a polypeptide of interest (e.g., CAR, or a portion thereof). As provided herein, the polypeptide of interest can be introduced into the cell through the use of expression vectors. In some embodiments, the expression vector (e.g., lentiviral vector) will comprise additional elements that will aid in the functional expression of the protein or polypeptide (e.g., CAR, or a portion thereof) encoded therein. In some embodiments, an expression vector comprising a nucleic acid encoding a polypeptide of interest (e.g., CAR, or a portion thereof) further comprises a mammalian promoter. In some embodiments, the vector further comprises an elongation-factor-1-alpha promoter (EF-1$\alpha$ promoter). Use of an EF-1$\alpha$ promoter may increase the efficiency in expression of downstream transgenes (e.g., a protein or polypeptide (e.g., CAR, or a portion thereof) encoding nucleic acid sequence). Physiologic promoters (e.g., an EF-1$\alpha$ promoter) may be less likely to induce integration mediated genotoxicity, and may abrogate the ability of the retroviral vector to transform stem cells. Other physiological promoters suitable for use in a vector (e.g., lentiviral vector) are known to those of skill in the art and may be incorporated into a vector of the present invention. In some embodiments, the vector (e.g., lentiviral vector) further comprises a non-requisite cis acting sequence that may improve titers and gene expression. One non-limiting example of a non-requisite cis acting sequence is the central polypurine tract and central termination sequence (cPPT/CTS) which is important for efficient reverse transcription and nuclear import. Other non-requisite cis acting sequences are known to those of skill in the art and may be incorporated into a vector (e.g., lentiviral vector) of the present invention. In some embodiments, the vector further comprises a posttranscriptional regulatory element. Posttranscriptional regulatory elements may improve RNA translation, improve transgene expression and stabilize RNA transcripts. One example of a posttranscriptional regulatory element is the woodchuck hepatitis virus posttranscriptional regulatory element (WPRE). Accordingly, in some embodiments a vector for the present invention further comprises a WPRE sequence. Various posttranscriptional regulator elements are known to those of skill in the art and may be incorporated into a vector (e.g., lentiviral vector) of the present invention. A vector of the present invention may further comprise additional elements such as a rev response element (RRE) for RNA transport, packaging sequences, and 5' and 3' long terminal repeats (LTRs). The term "long terminal repeat" or "LTR" refers to domains of base pairs located at the ends of retroviral DNAs which comprise U3, R and U5 regions. LTRs generally provide functions required for the expression of retroviral genes (e.g., promotion, initiation and polyadenylation of gene transcripts) and to viral replication. In some embodiments, a vector (e.g., lentiviral vector) of the present invention includes a 3' U3 deleted LTR. Accordingly, a vector (e.g., lentiviral vector) of the present invention may comprise any combination of the elements described herein to enhance the efficiency of functional expression of transgenes. For example, a vector (e.g., lentiviral vector) of the present invention may comprise a WPRE sequence, cPPT sequence, RRE sequence, in addition to a nucleic acid encoding for a protein or polypeptide (e.g., CAR).

In some embodiments, the vector is a self-inactivating vector. As used herein, the term "self-inactivating vector"

refers to vectors in which the 3' LTR enhancer promoter region (U3 region) has been modified (e.g., by deletion or substitution). A self-inactivating vector may prevent viral transcription beyond the first round of viral replication. Consequently, a self-inactivating vector may be capable of infecting and then integrating into a host genome (e.g., a mammalian genome) only once, and cannot be passed further. Accordingly, self-inactivating vectors may greatly reduce the risk of creating a replication-competent virus.

In order to assess the expression of a polypeptide or portions thereof, the expression vector to be introduced into a cell may also contain either a selectable marker gene or a reporter gene, or both, to facilitate identification and selection of expressing cells from the population of cells sought to be transfected or infected through viral vectors. In some embodiments, the selectable marker may be carried on a separate piece of DNA and used in a co-transfection or co-transduction procedure. Both selectable markers and reporter genes may be flanked with appropriate regulatory sequences to enable expression in the host cells. Useful selectable markers include, without limitation, antibiotic-resistance genes. Reporter genes are used for identifying potentially transfected cells and for evaluating the functionality of regulatory sequences. In general, a reporter gene is a gene that is not present in or expressed by the recipient organism or tissue and that encodes a polypeptide whose expression is manifested by some easily detectable property, e.g., enzymatic activity. Expression of the reporter gene is assessed at a suitable time after the DNA has been introduced into the recipient cells. Suitable reporter genes may include, without limitation, genes encoding luciferase, beta-galactosidase, chloramphenicol acetyl transferase, secreted alkaline phosphatase, or the green fluorescent protein gene (e.g., Ui-Tei et al., 2000 FEBS Letters 479: 79-82).

Dimerizing Agent

In certain embodiments, the first and second portion of the protein or polypeptide form a complete protein in the presence of a dimerizing agent. Any dimerizing agent known to one of ordinary skill in the art can be used, including but not limited to, rimiducid ((1R)-3-(3,4-dimethoxyphenyl)-1-[3-({[2-(2-{3-[(1R)-3-(3,4-dimethoxyphenyl)-1-[(2S)-1-[(2S)-2-(3,4,5-trimethoxyphenyl)butanoyl] piperidine-2-carbonyloxy]propyl]phenoxy}acetamido) ethyl] carbamoyl}methoxy)phenyl]propyl (2S)-1-[(2S)-2-(3,4,5-trimethoxyphenyl)butanoyl]piperidine-2-carboxylate (AP1903)), erythropoietin (EPO), thrombopoietin, or rapamycin, or analogues thereof. For example, the protein of interest that is split into separate portions that that can then be dimerized will contain a erythropoietin binding domain, thrombopoietin binding domain, or rapamycin, or analogoues thereof, binding domain, such that when the compounds are given the compound will facilitate the joining of the separate portions of the protein to form the complete protein. In some embodiments, a compound used to induce erythropoietin or thrombopoietin is administered, as opposed to erythropoietin or thrombopoietin themselves, to induce the production of erythropoietin or thrombopoietin in vivo, which will join the portions of the protein to form the complete protein.

In certain embodiments, the first and second portions of the protein or polypeptide can bind together through the excision of an intein domain. An intein is a protein domain that can spontaneously splice its flanking N- and C-terminal domains to become a mature protein and excise itself from a sequence. Similar to introns at the mRNA level, the protein is an intron-like protein and is therefore named intein. Embodiments of inteins can be found in the literature, see, for example, U.S. Pat. Nos. 10,407,742, and 10,087,213, which are incorporated by reference in their entirety herein.

Chimeric Antigen Receptors (CARs)

The present invention provides, among other things, compositions and methods for transducing cells (e.g. T cells) in vivo. In some embodiments, these compositions and methods are performed or used without culturing or transducing the cells ex-vivo. In some embodiments, a patient with a malignancy requiring CAR T cell therapy can be treated with an off-the-shelf composition that transduces their T cells in vivo, which generates CAR T cells in situ. The compositions and methods of the present invention, among other things, (i) are able to specifically transduce the target cells of interest, (ii) have high transduction efficiency to lead to a sufficient number of T cells carrying the transgene after in vivo administration, and (iii) result in transduced cells that are functional.

Certain embodiments of the invention include compositions comprising a polypeptide of interest that is a chimeric antigen receptor (CAR). CARs of the present invention comprise an extracellular (antigen binding) domain, a transmembrane domain, and an intracellular signaling domain. The intracellular signaling domain comprises a stimulatory domain, and optionally, a co-stimulatory domain.

The antigen binding domain may be operably linked to another domain of the CAR, such as the transmembrane domain or the intracellular domain, both described elsewhere herein, for expression in the cell. In one embodiment, a first nucleic acid sequence encoding the antigen binding domain is operably linked to a second nucleic acid encoding a transmembrane domain, and further operably linked to a third a nucleic acid sequence encoding an intracellular signaling domain.

The antigen binding domains described herein can be combined with any of the transmembrane domains described herein, any of the intracellular signaling domains or cytoplasmic domains described herein, or any of the other domains described herein that may be included in a CAR expressed by the vectors. In some embodiments, the CAR comprises a hinge domain, such as, but not limited to, those described herein. In some embodiments, the CAR comprises a spacer domain, such as, but not limited to, those described herein. In some embodiments, one or more of the antigen binding domain, transmembrane domain, and intracellular signaling domain is separated by a linker.

Extracellular/Antigen Binding Domain

The antigen binding domain of a CAR is an extracellular region of the CAR for binding to a specific target antigen including proteins, carbohydrates, and glycolipids. In some embodiments, the CAR comprises affinity to a target antigen on a target cell. The target antigen may include any type of protein, or epitope thereof, associated with the target cell. For example, the CAR may comprise affinity to a target antigen on a target cell that indicates a particular disease state of the target cell.

In one embodiment, the target cell antigen is a tumor associated antigen (TAA). Examples of tumor associated antigens (TAAs), include but are not limited to, differentiation antigens such as MART-1/MelanA (MART-I), gp100 (Pmel 17), tyrosinase, TRP-1, TRP-2 and tumor-specific multilineage antigens such as MAGE-1, MAGE-3, BAGE, GAGE-1, GAGE-2, p15; overexpressed embryonic antigens such as CEA; overexpressed oncogenes and mutated tumor-suppressor genes such as p53, Ras, HER-2/neu; unique tumor antigens resulting from chromosomal translocations; such as BCR-ABL, E2A-PRL, H4-RET, IGH-IGK, MYL-RAR; and viral antigens, such as the Epstein Barr virus antigens EBVA and the human papillomavirus (HPV) antigens E6 and E7. Other large, protein-based antigens include TSP-180, MAGE-4, MAGE-5, MAGE-6, RAGE, NY-ESO, p185erbB2, p180erbB-3, c-met, nm-23H1, PSA, TAG-72, CA 19-9, CA 72-4, CAM 17.1, NuMa, K-ras, beta-Catenin, CDK4, Mum-1, p 15, p 16, 43-9F, 5T4, 791Tgp72, alpha-fetoprotein, beta-HCG, BCA225, BTAA, CA 125, CA 15-3\CA 27.29\BCAA, CA 195, CA 242, CA-50, CAM43, CD68\P1, CO-029, FGF-5, G250, Ga733\EpCAM, HTgp-175, M344, MA-50, MG7-Ag, MOV18, NB/70K, NY-CO-1, RCASI, SDCCAG16, TA-90\Mac-2 binding protein\cyclophilin C-associated protein, TAAL6, TAG72, TLP, and TPS. In some embodiments, the antigen binding domain of the CAR targets an antigen that includes but is not limited to CD19, CD20, CD22, ROR1, Mesothelin, CD33/IL3Ra, c-Met, PSMA, PSCA, Glycolipid F77, EGFRVIII, GD-2, MY-ESO-1 TCR, MAGE A3 TCR, CD19, BCMA, CD33, or CD79b, and the like.

In some embodiments, the extracellular domain binds to CD20, CD22, CD123, CD38, CD19, BCMA, CD33, CD8, CCR7 or CD79b.

Depending on the desired antigen to be targeted, the CAR can be engineered to include the appropriate antigen binding domain that is specific to the desired antigen target. For example, if CD19 is the desired antigen that is to be targeted, an antibody for CD19 can be used as the antigen bind moiety for incorporation into the CAR.

In some embodiments, the target cell antigen is CD19. As such, in some embodiments, a CAR has affinity for CD19 on a target cell. This should not be construed as limiting in any way, as a CAR having affinity for any target antigen is suitable for use in any of the compositions or methods provided for herein.

As described herein, a CAR of the present disclosure having affinity for a specific target antigen on a target cell may comprise a target-specific binding domain. In some embodiments, the target-specific binding domain is a murine target-specific binding domain, e.g., the target-specific binding domain is of murine origin. In some embodiments, the target-specific binding domain is a human target-specific binding domain, e.g., the target-specific binding domain is of human origin.

In some embodiments, a CAR of the present disclosure may have affinity for one or more target antigens on one or more target cells. In some embodiments, a CAR may have affinity for one or more target antigens on a target cell. In such embodiments, the CAR is a bispecific CAR, or a multispecific CAR. In some embodiments, the CAR comprises one or more target-specific binding domains that confer affinity for one or more target antigens. In some embodiments, the CAR comprises one or more target-specific binding domains that confer affinity for the same target antigen. For example, a CAR comprising one or more target-specific binding domains having affinity for the same target antigen could bind distinct epitopes of the target antigen. When a plurality of target-specific binding domains is present in a CAR, the binding domains may be arranged in tandem and may be separated by linker peptides. For example, in a CAR comprising two target-specific binding domains, the binding domains are connected to each other covalently on a single polypeptide chain, through an oligo- or polypeptide linker, an Fc hinge region, or a membrane hinge region.

In some embodiments, the antigen binding domain is as provided herein. In some embodiments, the antigen binding domain is selected from the group consisting of an antibody, an antigen binding fragment (Fab), and a single-chain variable fragment (scFv). In some embodiments, the antigen binding domain is a VHH. In some embodiments, the antigen binding domain is a FN3 domain. In some embodiments, the antigen binding domain is a DARPIN. In some embodiments, a CD19 binding domain is selected from the group consisting of a CD19-specific antibody, a CD19-specific Fab, and a CD19-specific scFv. In one embodiment, a CD19 binding domain is a CD19-specific antibody. In some embodiments, a CD19 binding domain is a CD19-specific Fab. In some embodiments, a CD19 binding domain is a CD19-specific scFv. CD19 is just one example and any other target antigen can be substituted for the antibody or antibody type molecule. In some embodiments, the target antigen is CD20, CD22, CD123, CD38, CD19, BCMA, CD33, CD8, CCR7, or CD79b.

The antigen binding domain can include any domain that binds to the antigen and may include, but is not limited to, a monoclonal antibody, a polyclonal antibody, a synthetic antibody, a human antibody, a humanized antibody, a non-human antibody, and any fragment thereof. In some embodiments, the antigen binding domain portion comprises a mammalian antibody or a fragment thereof. The choice of antigen binding domain may depend upon the type and number of antigens that are present on the surface of a target cell.

As used herein, the term "single-chain variable fragment" or "scFv" is a fusion protein of the variable regions of the heavy (VH) and light chains (VL) of an immunoglobulin (e.g., mouse or human) covalently linked to form a VH:VL heterodimer. The heavy (VH) and light chains (VL) are either joined directly or joined by a peptide-encoding linker, which connects the N-terminus of the VH with the C-terminus of the VL, or the C-terminus of the VH with the N-terminus of the VL. In some embodiments, the antigen binding domain (e.g., CD19 binding domain) comprises an scFv having the configuration from N-terminus to C-terminus, VH-linker-VL. In some embodiments, the antigen binding domain comprises an scFv having the configuration from N-terminus to C-terminus, VL-linker-VH.

In some embodiments, the linker is rich in glycine for flexibility, as well as serine or threonine for solubility. The linker can link the heavy chain variable region and the light chain variable region of the extracellular antigen-binding domain. Non-limiting examples of linkers are disclosed in Shen et al., Anal. Chem. 80(6): 1910-1917 (2008) and WO 2014/087010, the contents of which are hereby incorporated by reference in their entireties. Various linker sequences are known in the art, including, without limitation, glycine serine (GS) linkers such as $(GS)_n$, $(GSGGS)_n$ (SEQ ID NO: 1), $(GGGS)_n$ (SEQ ID NO: 2), $(GGGGS)_n$ (SEQ ID NO: 3), $(GGSGG)_n$ (SEQ ID NO:4) where each n is, independently, an integer of at least 1 or 1-5. In some embodiments, the serine of the linker is replaced with an alanine.

Despite removal of the constant regions and the introduction of a linker, scFv proteins retain the specificity of the original immunoglobulin. Single chain Fv polypeptide antibodies can be expressed from a nucleic acid comprising VH- and VL-encoding sequences as described by Huston, et al. (Proc. Nat. Acad. Sci. USA, 85:5879-5883, 1988). See, also, U.S. Pat. Nos. 5,091,513, 5,132,405 and 4,956,778; and U.S. Patent Publication Nos. 20050196754 and 20050196754. Antagonistic scFvs having inhibitory activity have been described (see, e.g., Zhao et al., Hyrbidoma (Larchmt) 2008 27(6):455-51; Peter et al., J Cachexia Sarcopenia Muscle 2012 Aug. 12; Shieh et al., J Imunol 2009 183(4):2277-85; Giomarelli et al., Thromb Haemost 2007 97(6):955-63; Fife eta., J Clin Invst 2006 116(8):2252-61; Brocks et al., Immunotechnology 1997 3(3): 173-84; Moosmayer et al., Ther Immunol 1995 2(10:31-40). Agonistic scFvs having stimulatory activity have been described (see, e.g., Peter et al., J Bioi Chem 2003 25278(38):36740-7; Xie et al., Nat Biotech 1997 15(8):768-71; Ledbetter et al., Crit Rev Immunol 1997 17(5-6):427-55; Ho et al., BioChim Biophys Acta 2003 1638(3):257-66).

As used herein, "Fab" refers to a fragment of an antibody structure that binds to an antigen but is monovalent and does not have a Fc portion, for example, an antibody digested by the enzyme papain yields two Fab fragments and an Fc fragment (e.g., a heavy (H) chain constant region; Fc region that does not bind to an antigen).

As used herein, "F(ab')2" refers to an antibody fragment generated by pepsin digestion of whole IgG antibodies, wherein this fragment has two antigen binding (ab') (bivalent) regions, wherein each (ab') region comprises two separate amino acid chains, a part of a H chain and a light (L) chain linked by an S—S bond for binding an antigen and where the remaining H chain portions are linked together. A "F(ab')2" fragment can be split into two individual Fab' fragments.

Other examples of antibodies or antigen binding domains are provided for herein and can also be used in the CAR construct.

In some embodiments, the antigen binding domain may be derived from the same species in which the CAR will ultimately be used. For example, for use in humans, the antigen binding domain of the CAR may comprise a human antibody or a fragment thereof. In some embodiments, the antigen binding domain may be derived from a different species in which the CAR will ultimately be used. For example, for use in humans, the antigen binding domain of the CAR may comprise a murine antibody or a fragment thereof.

Transmembrane Domain

CARs comprise a transmembrane domain. The transmembrane domain of a subject CAR is a region that is capable of spanning the plasma membrane of a cell (e.g., an immune cell or precursor thereof). The transmembrane domain is for insertion into a cell membrane, e.g., a eukaryotic cell membrane. In some embodiments, the transmembrane domain connects the extracellular/antigen binding domain and the intracellular domain of a CAR.

In some embodiments, the transmembrane domain is naturally associated with one or more of the domains in the CAR. In some embodiments, the transmembrane domain can be selected or modified by one or more amino acid substitutions to avoid binding of such domains to the transmembrane domains of the same or different surface membrane proteins, to minimize interactions with other members of the receptor complex.

The transmembrane domain may be derived either from a natural or a synthetic source. Where the source is natural, the domain may be derived from any membrane-bound or transmembrane protein, e.g., a Type I transmembrane protein. Where the source is synthetic, the transmembrane domain may be any artificial sequence that facilitates insertion of the CAR into a cell membrane, e.g., an artificial hydrophobic sequence. Examples of the transmembrane domains include, without limitation, transmembrane domains derived from (i.e. comprise at least the transmembrane region(s) of) the alpha or beta chain of the T cell receptor, CD28, CD3 epsilon, CD3 zeta, CD45, CD4, CD5, CD7, CD8, CD9, CD16, CD22, CD33, CD37, CD64, CD80, CD86, CD134 (OX-40), CD137 (4-1BB), CD154 (CD40L), Toll-like receptor 1 (TLR1), TLR2, TLR3, TLR4, TLR5, TLR6, TLR7, TLR8, or TLR9. In some embodiments, the transmembrane domain may be synthetic, in which case it will comprise predominantly hydrophobic residues such as leucine and valine. In some embodiments, a triplet of phenylalanine, tryptophan and valine are at each end of a synthetic transmembrane domain.

The transmembrane domains described herein can be combined with any of the antigen binding domains described herein, any of the intracellular domains described herein, or any of the other domains described herein that may be included in a subject CAR.

In some embodiments, the transmembrane domain further comprises a hinge region. Accordingly, in some embodiments, a subject CAR may also include a hinge region. The hinge region of the CAR is a hydrophilic region which is located between the antigen binding domain and the transmembrane domain. The hinge region may include a domain selected from Fc fragments of antibodies, hinge regions of antibodies, CH2 regions of antibodies, CH3 regions of antibodies, artificial hinge sequences or combinations thereof. Examples of hinge regions include, without limitation, a CD8a hinge, artificial hinges made of polypeptides which may be as small as, three glycines (Gly), as well as CH1 and CH3 domains of IgGs (such as human IgG4).

In some embodiments, a subject CAR of the present disclosure includes a hinge region that connects the antigen binding domain with the transmembrane domain, which, in turn, connects to the intracellular domain. The hinge region can be capable of supporting the antigen binding domain to recognize and bind to the target antigen on the target cells (see, e.g., Hudecek et al., *Cancer Immunol. Res.* (2015) 3(2): 125-135). In some embodiments, the hinge region is a flexible domain. Without being bound to any particular theory, the hinge region can allow the antigen binding domain to have a structure to optimally recognize the specific structure and density of the target antigens on a cell such as tumor cell (Hudecek et al., supra). The flexibility of the hinge region can permit the hinge region to adopt many different conformations.

In some embodiments, the hinge region is an immunoglobulin heavy chain hinge region. In some embodiments, the hinge region is a hinge region polypeptide derived from a receptor (e.g., a CD8-derived hinge region).

The hinge region can have a length of from about 4 amino acids to about 50 amino acids, e.g., from about 4 aa to about 10 aa, from about 10 aa to about 15 aa, from about 15 aa to about 20 aa, from about 20 aa to about 25 aa, from about 25 aa to about 30 aa, from about 30 aa to about 40 aa, or from about 40 aa to about 50 aa. In some embodiments, the hinge region can have a length of greater than 5 aa, greater than 10 aa, greater than 15 aa, greater than 20 aa, greater than 25 aa, greater than 30 aa, greater than 35 aa, greater than 40 aa, greater than 45 aa, greater than 50 aa, greater than 55 aa, or more.

Suitable hinge regions can be readily selected and can be of any of a number of suitable lengths, such as from 1 amino acid (e.g., Gly) to 20 amino acids, from 2 amino acids to 15 amino acids, from 3 amino acids to 12 amino acids, including 4 amino acids to 10 amino acids, 5 amino acids to 9 amino acids, 6 amino acids to 8 amino acids, or 7 amino acids to 8 amino acids, and can be 1, 2, 3, 4, 5, 6, or 7 amino acids. Suitable hinge regions can have a length of greater than 20 amino acids (e.g., 30, 40, 50, 60 or more amino acids).

For example, hinge regions can include glycine polymers $(G)_n$, glycine-serine polymers (including, for example, $(GS)_n$, $(GSGGS)_n$ (SEQ ID NO:1) and $(GGGS)_n$ (SEQ ID NO:

2), where each n is, independently, an integer of at least one or 1-5), glycine-alanine polymers, alanine-serine polymers, and other flexible linkers known in the art. Glycine and glycine-serine polymers can be used. Glycine polymers can also be used.

In some embodiments, the hinge region is an immunoglobulin heavy chain hinge region. Immunoglobulin hinge region amino acid sequences are known in the art; see, e.g., Tan et al., *Proc. Natl. Acad. Sci. USA* (1990) 87(1): 162-166; and Huck et al., *Nucleic Acids Res.* (1986) 14(4): 1779-1789. The hinge region can comprise an amino acid sequence of a human IgG1, IgG2, IgG3, or IgG4, hinge region. In some embodiments, the hinge region can include one or more amino acid substitutions and/or insertions and/or deletions compared to a wild-type (naturally-occurring) hinge region.

In some embodiments, the hinge region can comprise an amino acid sequence derived from human CD8, or a variant thereof.

Intracellular Signaling Domain

A subject CAR also includes an intracellular signaling domain. The terms "intracellular signaling domain" and "intracellular domain" are used interchangeably herein. The intracellular signaling domain of the CAR is responsible for activation of at least one of the effector functions of the cell in which the CAR is expressed (e.g., immune cell). The intracellular signaling domain transduces the effector function signal and directs the cell (e.g., immune cell) to perform its specialized function, e.g., harming and/or destroying a target cell.

Examples of an intracellular domain include, but are not limited to, the cytoplasmic portion of a surface receptor, co-stimulatory molecule, and any molecule that acts in concert to initiate signal transduction in the T cell, as well as any derivative or variant of these elements and any synthetic sequence that has the same functional capability.

Examples of intracellular signaling domains include, without limitation, the ζ chain of the T cell receptor complex or any of its homologs, e.g., n chain, FcsRIγ and β chains, MB 1 (Iga) chain, B29 (Ig) chain, etc., human CD3 zeta chain, CD3 polypeptides (Δ, δ and ε), syk family tyrosine kinases (Syk, ZAP 70, etc.), src family tyrosine kinases (Lck, Fyn, Lyn, etc.), and other molecules involved in T cell transduction, such as CD2, CD5 and CD28. In some embodiments, the intracellular signaling domain may be human CD3 zeta chain, FcγRIII, FcsRI, cytoplasmic tails of Fc receptors, an immunoreceptor tyrosine-based activation motif (ITAM) bearing cytoplasmic receptors, and combinations thereof.

In some embodiments, the intracellular signaling domain of the CAR includes any portion of one or more co-stimulatory molecules, such as at least one signaling domain from CD2, CD3, CD8, CD27, CD28, ICOS, 4-1BB, PD-1, any derivative or variant thereof, any synthetic sequence thereof that has the same functional capability, and any combination thereof.

Other examples of the intracellular domain include a fragment or domain from one or more molecules or receptors including, but not limited to, TCR, CD3 zeta, CD3 gamma, CD3 delta, CD3 epsilon, CD86, common FcR gamma, FcR beta (Fc Epsilon RIb), CD79a, CD79b, Fcgamma RIIa, DAP10, DAP12, T cell receptor (TCR), CD8, CD27, CD28, 4-1BB (CD137), OX9, OX40, CD30, CD40, PD-1, ICOS, a KIR family protein, lymphocyte function-associated antigen-1 (LFA-1), CD2, CD7, LIGHT, NKG2C, B7-H3, a ligand that specifically binds with CD83, CDS, ICAM-1, GITR, BAFFR, HVEM (LIGHTR), SLAMF7, NKp80 (KLRF1), CD127, CD160, CD19, CD4, CD8alpha, CD8beta, IL2R beta, IL2R gamma, IL7R alpha, ITGA4, VLA1, CD49a, ITGA4, IA4, CD49D, ITGA6, VLA-6, CD49f, ITGAD, CD11d, ITGAE, CD103, ITGAL, CD11a, LFA-1, ITGAM, CDlib, ITGAX, CD11c, ITGB1, CD29, ITGB2, CD18, LFA-1, ITGB7, TNFR2, TRANCE/RANKL, DNAMI (CD226), SLAMF4 (CD244, 2B4), CD84, CD96 (Tactile), CEACAMI, CRT AM, Ly9 (CD229), CD160 (BY55), PSGLI, CD100 (SEMA4D), CD69, SLAMF6 (NTB-A, Ly108), SLAM (SLAMF1, CD150, IPO-3), BLAME (SLAMF8), SELPLG (CD162), LTBR, LAT, GADS, SLP-76, PAG/Cbp, NKp44, NKp30, NKp46, NKG2D, Toll-like receptor 1 (TLR1), TLR2, TLR3, TLR4, TLR5, TLR6, TLR7, TLR8, TLR9, other co-stimulatory molecules described herein, any derivative, variant, or fragment thereof, any synthetic sequence of a co-stimulatory molecule that has the same functional capability, and any combination thereof.

Additional examples of intracellular domains include, without limitation, intracellular signaling domains of several types of various other immune signaling receptors, including, but not limited to, first, second, and third generation T cell signaling proteins including CD3, B7 family costimulatory, and Tumor Necrosis Factor Receptor (TNFR) superfamily receptors (see, e.g., Park and Brentjens, J. Clin. Oncol. (2015) 33(6): 651-653). Additionally, intracellular signaling domains may include signaling domains used by NK and NKT cells (see, e.g., Hermanson and Kaufman, Front. Immunol. (2015) 6: 195) such as signaling domains of NKp30 (B7-H6) (see, e.g., Zhang et al., J. Immunol. (2012) 189(5): 2290-2299), and DAP 12 (see, e.g., Topfer et al., J. Immunol. (2015) 194(7): 3201-3212), NKG2D, NKp44, NKp46, DAP10, and CD3z.

Intracellular signaling domains of a CAR can include any desired signaling domain that provides a distinct signal (e.g., increased production of one or more cytokines by the cell; change in transcription of a target gene; change in activity of a protein; change in cell behavior, e.g., cell death; cellular proliferation; cellular differentiation; cell survival; modulation of cellular signaling responses; etc.) in response to activation of the CAR (i.e., activated by antigen and dimerizing agent). In some embodiments, the intracellular signaling domain includes at least one (e.g., one, two, three, four, five, six, etc.) ITAM motifs as described below. In some embodiments, the intracellular signaling domain includes DAP10/CD28 type signaling chains. In some embodiments, the intracellular signaling domain is not covalently attached to the membrane bound CAR, but is instead diffused in the cytoplasm.

Intracellular signaling domains can also include immunoreceptor tyrosine-based activation motif (ITAM)-containing intracellular signaling polypeptides. In some embodiments, an ITAM motif is repeated twice in an intracellular signaling domain, where the first and second instances of the ITAM motif are separated from one another by 6 to 8 amino acids. In some embodiments, the intracellular signaling domain of a subject CAR comprises 3 ITAM motifs.

In some embodiments, intracellular signaling domains includes the signaling domains of human immunoglobulin receptors that contain immunoreceptor tyrosine based activation motifs (ITAMs) such as, but not limited to, FcgammaRI, FcgammaRIIA, FcgammaRIIC, FcgammaRIIIA, FcRL5 (see, e.g., Gillis et al., Front. Immunol. (2014) 5:254).

A suitable intracellular signaling domain can also be an ITAM motif-containing portion that is derived from a polypeptide that contains an ITAM motif. For example, a suitable intracellular signaling domain can be an ITAM motif-containing domain from any ITAM motif-containing protein. Thus, a suitable intracellular signaling domain need not contain the entire sequence of the entire protein from which it is derived. Examples of suitable ITAM motif-containing polypeptides include, but are not limited to: DAP12, FCERIG (Fc epsilon receptor I gamma chain), CD3D (CD3 delta), CD3E (CD3 epsilon), CD3G (CD3 gamma), CD3Z (CD3 zeta), and CD79A (antigen receptor complex-associated protein alpha chain).

In some embodiments, the intracellular signaling domain is derived from DAP12 (also known as TYROBP; TYRO protein tyrosine kinase binding protein; KARAP; PLOSL; DNAX-activation protein 12; KAR-associated protein; TYRO protein tyrosine kinase-binding protein; killer activating receptor associated protein; killer-activating receptor-associated protein; etc.). In one embodiment, the intracellular signaling domain is derived from FCERIG (also known as FCRG; Fc epsilon receptor I gamma chain; Fc receptor gamma-chain; fc-epsilon RI-gamma; fcRgamma; fceRl gamma; high affinity immunoglobulin epsilon receptor subunit gamma;

immunoglobulin E receptor, high affinity, gamma chain; etc.). In some embodiments, the intracellular signaling domain is derived from T-cell surface glycoprotein CD3 delta chain (also known as CD3D; CD3-DELTA; T3D; CD3 antigen, delta subunit; CD3 delta; CD3d antigen, delta polypeptide (TiT3 complex); OKT3, delta chain; T-cell receptor T3 delta chain; T-cell surface glycoprotein CD3 delta chain; etc.). In some embodiments, the intracellular signaling domain is derived from T-cell surface glycoprotein CD3 epsilon chain (also known as CD3e, T-cell surface antigen T3/Leu-4 epsilon chain, T-cell surface glycoprotein CD3 epsilon chain, AI504783, CD3, CD3epsilon, T3e, etc.). In some embodiments, the intracellular signaling domain is derived from T-cell surface glycoprotein CD3 gamma chain (also known as CD3G, T-cell receptor T3 gamma chain, CD3-GAMMA, T3G, gamma polypeptide (TiT3 complex), etc.). In some embodiments, the intracellular signaling domain is derived from T-cell surface glycoprotein CD3 zeta chain (also known as CD3Z, T-cell receptor T3 zeta chain, CD247, CD3-ZETA, CD3H, CD3Q, T3Z, TCRZ, etc.). In some embodiments, the intracellular signaling domain is derived from CD79A (also known as B-cell antigen receptor complex-associated protein alpha chain; CD79a antigen (immunoglobulin-associated alpha); MB-1 membrane glycoprotein; ig-alpha; membrane-bound immunoglobulin-associated protein; surface IgM-associated protein; etc.). In some embodiments, an intracellular signaling domain suitable for use in a CAR of the present disclosure includes a DAP10/CD28 type signaling chain. In some embodiments, an intracellular signaling domain suitable for use in a CAR of the present disclosure includes a ZAP70 polypeptide. In some embodiments, the intracellular signaling domain includes a cytoplasmic signaling domain of TCR zeta, FcR gamma, FcR beta, CD3 gamma, CD3 delta, CD3 epsilon, CD5, CD22, CD79a, CD79b, or CD66d. In some embodiments, the intracellular signaling domain in the CAR includes a cytoplasmic signaling domain of human CD3 zeta.

While usually the entire intracellular signaling domain can be employed, in many cases it is not necessary to use the entire chain. To the extent that a truncated portion of the intracellular signaling domain is used, such truncated portion may be used in place of the intact chain as long as it transduces the effector function signal. The intracellular signaling domain includes any truncated portion of the intracellular signaling domain sufficient to transduce the effector function signal.

The intracellular signaling domains described herein can be combined with any of the antigen binding domains described herein, any of the transmembrane domains described herein, or any of the other domains described herein that may be included in the CAR.

In Vivo CART

The present disclosure provides methods for producing or generating a cell comprising a protein or polypeptide or polypeptide of interest, in a subject in vivo. In some embodiments, the methods comprise administering the engineered viral particle(s), such as those provided for herein. In some embodiments, the engineered viral particle comprises an engineered envelope harboring a mutated fusion protein, a chimeric gag protein, and an engineered targeting moiety for binding to a target cell, wherein the mutated fusion protein does not bind to its natural receptor; and a nucleic acid encoding a polypeptide of interest. In some embodiments, the engineered viral particle comprises an engineered envelope harboring a mutated fusion protein and an engineered targeting moiety for binding to a target cell, wherein the mutated fusion protein does not bind to its natural receptor; and a nucleic acid molecule encoding a polypeptide of interest.

In some embodiments, the methods comprise administering a first viral particle and a second viral particle. The first viral particle comprises a chimeric gag protein, a first targeting moiety that binds to a first target on a cell and a first nucleic acid molecule that encodes a first portion of a protein or a polypeptide of interest. The second viral particle comprises a chimeric gag protein, a second targeting moiety that binds to a second target on the cell and a second nucleic acid molecule that encodes a second portion of the protein or the polypeptide of interest. When expressed in the cell, the first and second portions of the protein or the polypeptide bind together, or interact with one another, to form a complete protein or polypeptide in the cell in the subject.

In certain embodiments, the method further comprises administering a dimerizing agent to the subject to form the protein or polypeptide in the subject. Any dimerizing agent, as discussed in detail elsewhere herein, may be used. In certain embodiments, administering the dimerizing agent is required to form the complete protein, such as a CAR. The use of the dimerizing agent can provide an additional layer of control of the method and function of the protein in vivo.

In certain embodiments, the first portion and the second portion of the protein or the polypeptide comprise an intein domain and the intein domain is excised to link the first and second portion to form the complete protein or polypeptide.

In certain embodiments, the cell is a T cell, a CD4+ T cell, a CD8+ T cell, a NK cell, an alpha-beta T cell, a gamma-delta T cell, a lymphoid progenitor cell, a hematopoietic stem cell, a myeloid cell, a monocyte, a macrophage, a central memory T cell, a naïve T cells, an activated T cell, a regulatory T Cell (Treg), or a CD8+naïve/central memory cell (CD8+CCR7+) and CD4+naïve/central memory cell (CD4+CCR7+). In some embodiments, the cell is a CD4+ CD8+ cell. These cell types are not to be limiting and as any type of cell can be generated using the methods and compositions provided herein.

In certain embodiments, the polypeptide of interest is a chimeric antigen receptor (CAR). Non-limiting examples of CARs are provided herein, but these are for illustrative purposes only and any type of CAR could be expressed in vivo using the compositions and methods provided herein.

In certain embodiments, the polypeptide of interest is a hemoglobin beta chain.

In certain embodiments, the viral vectors or particles are administered to the subject by injecting the vectors into the peripheral blood of the subject. In certain embodiments, the viral vectors or particles are administered to the subject by injecting the vectors into a lymph node in the subject.

In some embodiments, methods of producing CART cells directly in a subject are provided that do not, in some embodiments, involve, or use, the ex vivo production, expansion, or activation of T cells. In some embodiments, the methods comprise using a lentiviral particle pseudotyped with (a) mutated measles and/or (b) Nipah virus glycoproteins. In some embodiments, the lentiviral particle is modified so that it cannot infect a target cell, without a specific targeting domain also being present on the surface of the particle. In this way, CD4 T cells (using an anti-CD4 targeting domain) or CD8 T cells (using an anti-CD8 targeting domain) are transduced. The transgene carried by the vectors encodes a CAR. T cells can be transduced in the circulation by injection of the vectors into the peripheral blood. Alternatively, T cells resident in lymphatic organs can be transduced by, for example, injecting vectors directly into a T cell rich organ such as a lymph node.

Methods of Treatment

Also provided herein are methods of treating a disease in a subject in need thereof.

In some embodiments, the methods provided include, but are not limited to, methods of treating a disease in a subject in need thereof, comprising administering to the subject the viral particle(s) provided herein to treat the disease.

In certain embodiments, the disease is a cancer. In addition, the compositions provided for herein can be used in methods for the treatment of any condition related to a cancer, such as a cell-mediated immune response against a tumor cell(s), where it is desirable to treat or alleviate the disease. The types of cancers to be treated include, but are not limited to, carcinoma, blastoma, sarcoma, certain leukemia or lymphoid malignancies, benign and malignant tumors, malignancies e.g., sarcomas, carcinomas, and melanomas. Other exemplary cancers include, but are not limited to, breast cancer, prostate cancer, ovarian cancer, cervical cancer, skin cancer, pancreatic cancer, colorectal cancer, renal cancer, liver cancer, brain cancer, lymphoma, leukemia, lung cancer, thyroid cancer, and the like. The cancers may be non-solid tumors (such as hematological tumors) or solid tumors. Adult tumors/cancers and pediatric tumors/cancers are also included. In one embodiment, the cancer is a hematological tumor. In one embodiment, the cancer is a carcinoma. In one embodiment, the cancer is a sarcoma. In one embodiment, the cancer is a leukemia. In one embodiment the cancer is a solid tumor.

Solid tumors are abnormal masses of tissue that usually do not contain cysts or liquid areas. Solid tumors can be benign or malignant. Different types of solid tumors are named for the type of cells that form them (such as sarcomas, carcinomas, and lymphomas). Examples of solid tumors, such as sarcomas and carcinomas, include fibrosarcoma, myxosarcoma, liposarcoma, chondrosarcoma, osteosarcoma, synovioma, mesothelioma, Ewing's tumor, leiomyosarcoma, rhabdomyosarcoma, colon carcinoma, lymphoid malignancy, pancreatic cancer, breast cancer, lung cancers, ovarian cancer, prostate cancer, hepatocellular carcinoma, squamous cell carcinoma, basal cell carcinoma, adenocarcinoma, sweat gland carcinoma, medullary thyroid carcinoma, papillary thyroid carcinoma, pheochromocytomas sebaceous gland carcinoma, papillary carcinoma, papillary adenocarcinomas, medullary carcinoma, bronchogenic carcinoma, renal cell carcinoma, hepatoma, bile duct carcinoma, choriocarcinoma, Wilms' tumor, cervical cancer, testicular tumor, seminoma, bladder carcinoma, melanoma, CNS tumors (such as a glioma (such as brainstem glioma and mixed gliomas), glioblastoma (also known as glioblastoma multiforme) astrocytoma, CNS lymphoma, germinoma, medulloblastoma, Schwannoma craniopharyogioma, ependymoma, pinealoma, hemangioblastoma, acoustic neuroma, oligodendroglioma, menangioma, neuroblastoma, retinoblastoma and brain metastases).

Carcinomas that can be amenable to therapy by the methoda disclosed herein include, but are not limited to, esophageal carcinoma, hepatocellular carcinoma, basal cell carcinoma (a form of skin cancer), squamous cell carcinoma (various tissues), bladder carcinoma, including transitional cell carcinoma (a malignant neoplasm of the bladder), bronchogenic carcinoma, colon carcinoma, colorectal carcinoma, gastric carcinoma, lung carcinoma, including small cell carcinoma and non-small cell carcinoma of the lung, adrenocortical carcinoma, thyroid carcinoma, pancreatic carcinoma, breast carcinoma, ovarian carcinoma, prostate carcinoma, adenocarcinoma, sweat gland carcinoma, sebaceous gland carcinoma, papillary carcinoma, papillary adenocarcinoma, cystadenocarcinoma, medullary carcinoma, renal cell carcinoma, ductal carcinoma in situ or bile duct carcinoma, choriocarcinoma, seminoma, embryonal carcinoma, Wilm's tumor, cervical carcinoma, uterine carcinoma, testicular carcinoma, osteogenic carcinoma, epithelial carcinoma, and nasopharyngeal carcinoma.

In certain exemplary embodiments, the compositions provided herein can be used in methods to treat a myeloma, or a condition related to myeloma. Examples of myeloma or conditions related thereto include, without limitation, light chain myeloma, non-secretory myeloma, monoclonal gamopathy of undertermined significance (MGUS), plasmacytoma (e.g., solitary, multiple solitary, extramedullary plasmacytoma), amyloidosis, and multiple myeloma. In some embodiments, a methods of treating multiple myeloma are provided. In some embodiments, the multiple myeloma is refractory myeloma. In some embodiments, the multiple myeloma is relapsed myeloma.

In certain exemplary embodiments, the in vivo modified immune cells produced using the vectors and compositions provided herein are used to treat a melanoma, or a condition related to melanoma. Examples of melanoma or conditions related thereto include, without limitation, superficial spreading melanoma, nodular melanoma, lentigo maligna melanoma, acral lentiginous melanoma, amelanotic melanoma, or melanoma of the skin (e.g., cutaneous, eye, vulva, vagina, rectum melanoma). In some embodiments, the melanoma is cutaneous melanoma In some embodiments, the melanoma is refractory melanoma. In some embodiments, the melanoma is relapsed melanoma.

In some embodiments, the vectors and compositions provided herein are used to treat a sarcoma, or a condition related to sarcoma. Examples of sarcoma or conditions related thereto include, without limitation, angiosarcoma, chondrosarcoma, chordoma, endotheliosarcoma, Ewing's sarcoma, fibrosarcoma, gastrointestinal stromal tumor, leiomyosarcoma, liposarcoma, lymphangiosarcoma, lymphangioendotheliosarcoma, mesothelioma, malignant peripheral nerve sheath tumor, myxosarcoma, osteogenic sarcoma, osteosarcoma, pleomorphic sarcoma, rhabdomyosarcoma, synovioma, synovial sarcoma, and other soft tissue sarcomas. In some embodiments, the sarcoma is synovial sarcoma. In some embodiments, the sarcoma is liposarcoma such as myxoid/round cell liposarcoma, differentiated/dedifferentiated liposarcoma, or pleomorphic liposarcoma. In some embodiments, the sarcoma is myxoid/round cell liposarcoma. In some embodiments, the sarcoma is refractory sarcoma. In some embodiments, the sarcoma is relapsed sarcoma.

In certain embodiments, the compositions and vectors are used in methods for treating sickle cell disease. In some embodiments, the viral vectors or particles are administered to a subject suffering from sickle cell disease, wherein the particles encode the hemoglobin beta chain. When expressed in the cell, the hemoglobin beta chain is expressed and alleviates the symptoms of sickle cell disease to treat the disease.

In certain embodiments, the methods comprise administering a dimerizing agent to form the complete protein or polypeptide in the cell from the portions of the complete protein encoded by the plurality of the vectors.

In some embodiments, the subject has been treated with a therapeutic agent targeting the disease or condition, e.g. the tumor, prior to administration of the composition or plurality of viral vectors. In some aspects, the subject is refractory or non-responsive to the other therapeutic agent. In some embodiments, the subject has persistent or relapsed disease, e.g., following treatment with another therapeutic intervention, including chemotherapy, radiation, and/or hematopoietic stem cell transplantation (HSCT), e.g., allogenic HSCT. In some embodiments, the administration effectively treats the subject despite the subject having become resistant to another therapy.

In some embodiments, the subject is responsive to the other therapeutic agent, and treatment with the therapeutic agent reduces disease burden. In some aspects, the subject is initially responsive to the therapeutic agent, but exhibits a relapse of the disease or condition over time. In some embodiments, the subject has not relapsed. In some such embodiments, the subject is determined to be at risk for relapse, such as at a high risk of relapse, and thus the cells are administered prophylactically, e.g., to reduce the likelihood of or prevent relapse. In some aspects, the subject has not received prior treatment with another therapeutic agent.

The administration of the compositions may be carried out in any convenient manner known to those of skill in the art. For example, the compositions may be administered to a subject by aerosol inhalation, injection, ingestion, transfusion, implantation or transplantation. The compositions described herein may be administered to a patient transarterially, subcutaneously, intradermally, intratumorally, intranodally, intramedullary, intramuscularly, by intravenous (i.v.) injection, or intraperitoneally. In other instances, the compositions is injected directly into a site of a local disease site in the subject, a lymph node, an organ, a tumor, and the like.

For the prevention or treatment of disease, the appropriate dosage may depend on the type of disease to be treated, the severity and course of the disease, whether the composition is administered for preventive or therapeutic purposes, previous therapy, the subject's clinical history and response to the treatment, and the discretion of the attending physician. The composition is, in some embodiments, suitably administered to the subject at one time or over a series of treatments.

In some embodiments, the composition is administered as part of a combination treatment, such as simultaneously with or sequentially with, in any order, another therapeutic intervention, such as an antibody or engineered cell or receptor or agent, such as a cytotoxic or therapeutic agent. The composition(s), in some embodiments, is co-administered with one or more additional therapeutic agents or in connection with another therapeutic intervention, either simultaneously or sequentially in any order. In some contexts, the composition is co-administered with another therapy sufficiently close in time such that the composition enhances the effect of one or more additional therapeutic agents, or vice versa. In some embodiments, the composition is administered prior to the one or more additional therapeutic agents. In some embodiments, the composition is administered after the one or more additional therapeutic agents. In some embodiments, the one or more additional agents includes a cytokine, such as IL-2, for example, to enhance persistence. In some embodiments, the methods comprise administration of a chemotherapeutic agent. In some embodiments, the methods do not comprise the administration of a chemotherapeutic agent.

In certain embodiments, the compositions may be administered to a subject in combination with an immune checkpoint antibody (e.g., an anti-PD1, anti-CTLA-4, or anti-PDL1 antibody). For example, viral vectors may be administered in combination with an antibody or antibody fragment targeting, for example, PD-1 (programmed death 1 protein). Examples of anti-PD-1 antibodies include, but are not limited to, pembrolizumab (KEYTRUDA®, formerly lambrolizumab, also known as MK-3475), and nivolumab (BMS-936558, MDX-1106, ONO-4538, OPDIVA®) or an antigen-binding fragment thereof. In certain embodiments, the compositions may be administered in combination with an anti-PD-L1 antibody or antigen-binding fragment thereof. Examples of anti-PD-L1 antibodies include, but are not limited to, BMS-936559, MPDL3280A (TECENTRIQ®, Atezolizumab), and MEDI4736 (Durvalumab, Imfinzi). In certain embodiments, the composition may be administered in combination with an anti-CTLA-4 antibody or antigen-binding fragment thereof. An example of an anti-CTLA-4 antibody includes, but is not limited to, Ipilimumab (trade name Yervoy). Other types of immune checkpoint modulators may also be used including, but not limited to, small molecules, siRNA, miRNA, and CRISPR systems. Immune checkpoint modulators may be administered before, after, or concurrently with the viral vector. In certain embodiments, combination treatment comprising an immune checkpoint modulator may increase the therapeutic efficacy of a therapy comprising a composition as provided herein. The other therpeutic can be adminsitered simultaneously, before, or after the vectors provided herein are administered to the subject.

In certain embodiments, the subject is provided a secondary treatment. Secondary treatments include but are not limited to chemotherapy, radiation, surgery, and medications. In some embodiments, the subject is not provided a secondary treatment.

In some embodiments, the methods are performed without a lymphodepletion step, such as the administration of cyclophosphamide and/or fludarabine.

In some embodiments, the subject can be administered a conditioning therapy after the administration of the vectors to kill certain immune cells that are not transduced with the CAR encoded by the plurality of the vectors. This can be done by including a selection marker that is encoded by the plurality of the vectors, such as described in U.S. Patent Publication No. 201909261223. In some embodiments, the conditioning therapy comprises administering an effective amount of cyclophosphamide to the subject. In some embodiments, the conditioning therapy comprises administering an effective amount of fludarabine to the subject. In some embodiments, the conditioning therapy comprises administering an effective amount of a combination of cyclophosphamide and fludarabine to the subject.

In some embodiments, a specific dosage regimen of the present disclosure includes a lymphodepletion step after the administration of the composition. In an exemplary embodiment, the lymphodepletion step includes administration of cyclophosphamide and/or fludarabine.

In some embodiments, the lymphodepletion step includes administration of cyclophosphamide at a dose of between about 200 $mg/m^2$/day and about 2000 $mg/m^2$/day (e.g., 200 $mg/m^2$/day, 300 $mg/m^2$/day, or 500 $mg/m^2$/day). In an exemplary embodiment, the dose of cyclophosphamide is about 300 $mg/m^2$/day. In some embodiments, the lymphodepletion step includes administration of fludarabine at a dose of between about 20 $mg/m^2$/day and about 900 $mg/m^2$/day (e.g., 20 $mg/m^2$/day, 25 $mg/m^2$/day, 30 $mg/m^2$/day, or 60 $mg/m^2$/day). In an exemplary embodiment, the dose of fludarabine is about 30 $mg/m^2$/day.

In some embodiment, the lymphodepletion step includes administration of cyclophosphamide at a dose of between about 200 $mg/m^2$/day and about 2000 $mg/m^2$/day (e.g., 200 $mg/m^2$/day, 300 $mg/m^2$/day, or 500 $mg/m^2$/day), and fludarabine at a dose of between about 20 $mg/m^2$/day and about 900 $mg/m^2$/day (e.g., 20 $mg/m^2$/day, 25 $mg/m^2$/day, 30 $mg/m^2$/day, or 60 $mg/m^2$/day). In an exemplary embodiment, the lymphodepletion step includes administration of cyclophosphamide at a dose of about 300 $mg/m^2$/day, and fludarabine at a dose of about 30 $mg/m^2$/day.

In an exemplary embodiment, the dosing of cyclophosphamide is 300 $mg/m^2$/day over three days, and the dosing of fludarabine is 30 $mg/m^2$/day over three days.

It is known in the art that one of the adverse effects of the use of CAR T cells can be the onset of immune activation, known as cytokine release syndrome (CRS). CRS is immune activation resulting in elevated inflammatory cytokines. CRS is a known on-target toxicity, development of which likely correlates with efficacy. Clinical and laboratory measures range from mild CRS (constitutional symptoms and/or grade-2 organ toxicity) to severe CRS (sCRS; grade ≥3 organ toxicity, aggressive clinical intervention, and/or potentially life threatening). Clinical features include: high fever, malaise, fatigue, myalgia, nausea, anorexia, tachycardia/hypotension, capillary leak, cardiac dysfunction, renal impairment, hepatic failure, and disseminated intravascular coagulation. Dramatic elevations of cytokines including interferon-gamma, granulocyte macrophage colony-stimulating factor, IL-10, and IL-6 have been shown following CAR T-cell infusion. One CRS signature is elevation of cytokines including IL-6 (severe elevation), IFN-gamma, TNF-alpha (moderate), and IL-2 (mild). Elevations in clinically available markers of inflammation including ferritin and C-reactive protein (CRP) have also been observed to correlate with the CRS syndrome. The presence of CRS generally correlates with expansion and progressive immune activation of adoptively transferred cells. It has been demonstrated that the degree of CRS severity is dictated by disease burden at the time of infusion as patients with high tumor burden experience a more sCRS.

Accordingly, in some embodiments, the methods comprise, following the diagnosis of CRS, appropriate CRS management strategies to mitigate the physiological symptoms of uncontrolled inflammation without dampening the antitumor efficacy of the in vivo engineered cells (e.g., CAR T cells). CRS management strategies are known in the art. For example, systemic corticosteroids may be administered to rapidly reverse symptoms of sCRS (e.g., grade 3 CRS) without compromising initial antitumor response.

In some embodiments, an anti-IL-6R antibody may be administered. An example of an anti-IL-6R antibody is the Food and Drug Administration-approved monoclonal antibody tocilizumab, also known as atlizumab (marketed as Actemra, or RoActemra). Tocilizumab is a humanized monoclonal antibody against the interleukin-6 receptor (IL-6R). Administration of tocilizumab has demonstrated near-immediate reversal of CRS.

CRS is generally managed based on the severity of the observed syndrome and interventions are tailored as such. CRS management decisions may be based upon clinical signs and symptoms and response to interventions, not solely on laboratory values alone.

Mild to moderate cases generally are treated with symptom management with fluid therapy, non-steroidal anti-inflammatory drug (NSAID) and antihistamines as needed for adequate symptom relief. More severe cases include patients with any degree of hemodynamic instability; with any hemodynamic instability, the administration of tocilizumab is recommended. The first-line management of CRS may be tocilizumab, in some embodiments, at the labeled dose of 8 mg/kg IV over 60 minutes (not to exceed 800 mg/dose); tocilizumab can be repeated Q8 hours. If suboptimal response to the first dose of tocilizumab, additional doses of tocilizumab may be considered. Tocilizumab can be administered alone or in combination with corticosteroid therapy. Patients with continued or progressive CRS symptoms, inadequate clinical improvement in 12-18 hours or poor response to tocilizumab, may be treated with high-dose corticosteroid therapy, generally hydrocortisone 100 mg IV or methylprednisolone 1-2 mg/kg. In patients with more severe hemodynamic instability or more severe respiratory symptoms, patients may be administered high-dose corticosteroid therapy early in the course of the CRS. CRS management guidance may be based on published standards (Lee et al. (2019) *Biol Blood Marrow Transplant*, doi.org/10.1016/j.bbmt.2018.12.758; Neelapu et al. (2018) *Nat Rev Clin Oncology,* 15:47; Teachey et al. (2016) (*Cancer Discov,* 6(6): 664-679).

Features consistent with Macrophage Activation Syndrome (MAS) or Hemophagocytic lymphohistiocytosis (HLH) have been observed in patients treated with CAR-T therapy (Henter, 2007), coincident with clinical manifestations of the CRS. MAS appears to be a reaction to immune activation that occurs from the CRS, and should therefore be considered a manifestation of CRS. MAS is similar to HLH (also a reaction to immune stimulation). The clinical syndrome of MAS is characterized by high grade non-remitting fever, cytopenias affecting at least two of three lineages, and hepatosplenomegaly. It is associated with high serum ferritin, soluble interleukin-2 receptor, and triglycerides, and a decrease of circulating natural killer (NK) activity.

In some embodiments, methods of treating cancer in a subject in need thereof are provided, the methods comprising administering to the subject any of the compositions, such as the viral particle(s), provided herein. In some embodiments methods of treating cancer in a subject in need thereof are provided, the methods comprising administering to the subject a compostion generated by any one of the methods disclosed herein.

Pharmaceutical Compositions and Formulations

The compositions disclosed herein can comprise a pharmaceutical composition, and for example include a pharmaceutically acceptable carrier, and/or a pharmaceutical formulation.

The term "pharmaceutical formulation" refers to a preparation which is in such form as to permit the biological activity of an active ingredient contained therein to be effective, and which contains no additional components which are unacceptably toxic to a subject to which the formulation would be administered. A "pharmaceutically acceptable carrier" refers to an ingredient in a pharmaceutical formulation, other than an active ingredient, which is nontoxic to a subject. A pharmaceutically acceptable carrier includes, but is not limited to, a buffer, excipient, stabilizer, or preservative. In some aspects, the choice of carrier is determined in part by the particular cell and/or by the method of administration. Accordingly, there are a variety of suitable formulations. For example, the pharmaceutical composition can contain preservatives.

Suitable preservatives may include, for example, methylparaben, propylparaben, sodium benzoate, and benzalkonium chloride. In some aspects, a mixture of two or more preservatives is used. The preservative or mixtures thereof are typically present in an amount of about 0.0001% to about 2% by weight of the total composition. Carriers are described, e.g., by Remington's Pharmaceutical Sciences 16th edition, Osol, A. Ed. (1980). Pharmaceutically acceptable carriers are generally nontoxic to recipients at the dosages and concentrations employed, and include, but are not limited to: buffers such as phosphate, citrate, and other organic acids; antioxidants including ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as polyethylene glycol (PEG).

Buffering agents in some aspects are included in the compositions. Suitable buffering agents include, for example, citric acid, sodium citrate, phosphoric acid, potassium phosphate, and various other acids and salts. In some aspects, a mixture of two or more buffering agents is used. The buffering agent or mixtures thereof are typically present in an amount of about 0.001% to about 4% by weight of the total composition. Methods for preparing administrable pharmaceutical compositions are known. Exemplary methods are described in more detail in, for example, Remington: The Science and Practice of Pharmacy, Lippincott Williams & Wilkins; 21st ed. (May 1, 2005).

The formulations can include aqueous solutions. The formulation or composition may also contain more than one active ingredient useful for the particular indication, disease, or condition being treated with the composition, preferably those with activities complementary to the composition, where the respective activities do not adversely affect one another. Such active ingredients are suitably present in combination in amounts that are effective for the purpose intended. Thus, in some embodiments, the pharmaceutical composition further includes other pharmaceutically active agents or drugs, such as chemotherapeutic agents, e.g., asparaginase, busulfan, carboplatin, cisplatin, daunorubicin, doxorubicin, fluorouracil, gemcitabine, hydroxyurea, methotrexate, paclitaxel, rituximab, vinblastine, and/or vincristine. The pharmaceutical composition in some embodiments contains the composition in amounts effective to treat or prevent the disease or condition, such as a therapeutically effective or prophylactically effective amount. Therapeutic or prophylactic efficacy in some embodiments is monitored by periodic assessment of treated subjects. The desired dosage can be delivered by a single bolus administration of the composition, by multiple bolus administrations of the composition, or by continuous infusion administration of the composition. In some embodiments, the pharmaceutical composition does not include a chemotherapeutic.

Formulations include those for oral, intravenous, intraperitoneal, subcutaneous, pulmonary, transdermal, intramuscular, intranasal, buccal, sublingual, or suppository administration. In some embodiments, the composition is administered parenterally. The term "parenteral," as used herein, includes intravenous, intramuscular, subcutaneous, rectal, vaginal, and intraperitoneal administration. In some embodiments, the composition is administered to the subject using peripheral systemic delivery by intravenous, intraperitoneal, or subcutaneous injection. Compositions in some embodiments are provided as sterile liquid preparations, e.g., isotonic aqueous solutions, suspensions, emulsions, dispersions, or viscous compositions, which may in some aspects be buffered to a selected pH. Liquid preparations are normally easier to prepare than gels, other viscous compositions, and solid compositions. Additionally, liquid compositions are somewhat more convenient to administer, especially by injection. Viscous compositions, on the other hand, can be formulated within the appropriate viscosity range to provide longer contact periods with specific tissues. Liquid or viscous compositions can comprise carriers, which can be a solvent or dispersing medium containing, for example, water, saline, phosphate buffered saline, polyoi (for example, glycerol, propylene glycol, liquid polyethylene glycol) and suitable mixtures thereof.

Sterile injectable solutions can be prepared by incorporating the composition in a solvent, such as in admixture with a suitable carrier, diluent, or excipient such as sterile water, physiological saline, glucose, dextrose, or the like. The compositions can contain auxiliary substances such as wetting, dispersing, or emulsifying agents (e.g., methylcellulose), pH buffering agents, gelling or viscosity enhancing additives, preservatives, flavoring agents, and/or colors, depending upon the route of administration and the preparation desired. Standard texts may in some aspects be consulted to prepare suitable preparations.

Various additives which enhance the stability and sterility of the compositions, including antimicrobial preservatives, antioxidants, chelating agents, and buffers, can be added. Prevention of the action of microorganisms can be ensured by various antibacterial and antifungal agents, for example, parabens, chlorobutanol, phenol, and sorbic acid. Prolonged absorption of the injectable pharmaceutical form can be brought about by the use of agents delaying absorption, for example, aluminum monostearate and gelatin.

The formulations to be used for in vivo administration are generally sterile. Sterility may be readily accomplished, e.g., by filtration through sterile filtration membranes.

In some embodiments, the following embodiments are provided:

1. An engineered viral particle comprising
   i. an engineered envelope comprising a mutated fusion protein, a chimeric gag protein, and an engineered targeting moiety for binding to a target cell, wherein the mutated fusion protein does not bind to its natural receptor; and ii. a nucleic acid encoding a polypeptide of interest.

2. The engineered viral particle of embodiment 1, wherein the chimeric gag protein is xHIV gag protein.
3. The engineered viral particle of embodiments 1 or 2, wherein the viral particle further comprises nucleotide sequence encoding a SIV element, and/or a Pol protein.
4. The engineered viral particle of embodiment 2, wherein the xHIV gag protein is encoded by the nucleic acid sequence as set forth in SEQ ID NO: 5.
5. The engineered viral particle of embodiment 2, wherein the xHIV gag protein is encoded by the nucleic acid sequence as set forth in SEQ ID NO: 6.
6. The engineered viral particle of embodiment 3, wherein the SIV element is encoded by the nucleic acid sequence as set forth in SEQ ID NO: 7.
7. The engineered viral particle of embodiment 3, wherein the Pol protein is encoded by the nucleic acid sequence as set forth in SEQ ID NO: 8.
8. The engineered viral particle of embodiment 2, wherein the xHIV gag protein comprises an amino acid sequence as set forth in SEQ ID NO: 9.
9. The engineered viral particle of embodiment 3, wherein the Pol protein comprises an amino acid sequence as set forth in SEQ ID NO: 10.
10. The engineered viral particle of any one of embodiments 1-9, wherein the targeting moiety is fused to the mutated fusion protein.
11. The engineered viral particle of embodiments 1-10, wherein the viral particle is a lentivirus pseudotyped with a measles virus (MV) hemagglutinin (HA) protein or an MV fusion (F) protein, a Nipah F protein, or a Nipah G protein, wherein the MV-HA protein or the MV-F protein comprises a mutated binding domain compared to its naturally occurring binding domain.
12. The engineered viral particle of embodiment 11, wherein the targeting moiety is fused to the MV-HA protein the MV-F protein, the Nipah F protein, or the Nipah G protein.
13. The engineered viral particle of any one of the preceeding embodiments, wherein the targeting moiety is an antibody, a scFv antibody, an antigen binding domain, a DARPIN, a VHH domain antibody, a nanobody, single domain antibody, a FN3 domain, or any combination thereof.
14. The engineered viral particle of any one of the preceeding embodiments, wherein the targeting moiety is selected from the group consisting of Stem Cell Factor protein (SCF, KIT-ligand, KL, or steel factor) or a moiety that binds to cKit (CD117), CD4, CD8, CD3, CD5, CD6, CD7, CD2, TCR alpha, TCR beta, TCR gamma, TCR delta, CD10, CD34, CD110, CD33, CD14, CD68, CCR7, CD62L, CD25, CCR2, CCR3, CCR4, CCR5, CCR6, CCR7, and CXCR3.
15. The engineered viral particle of any one of the preceeding embodiments, wherein the polypeptide of interest is a chimeric antigen receptor (CAR) or a portion thereof.
16. The engineered viral particle of embodiment 15, wherein the chimeric antigen receptor comprises an extracellular domain, transmembrane domain, and an intracellular signaling domain.
17. The engineered viral particle of embodiment 16, wherein the extracellular domain binds to CD20, CD22, CD123, CD38, CD19, BCMA, CD33, or CD79b.
18. The engineered viral particle of embodiment 1, wherein the polypeptide of interest is a hemoglobin beta chain.
19. The engineered viral particle of any of the preceding embodiments, wherein the viral particle is a pseudotyped lentiviral vector, an adenovirus, or an adeno-associated virus.
20. The engineered viral particle of embodiment 19, wherein the pseudotyped lentiviral vector is pseudotyped with a morbillivirus or a henipavirus, such as a measles virus, glycoprotein and/or a Nipah virus glycoprotein.
21. The engineered viral particle of embodiment 19, wherein the pseudotyped vector is pseudotyped with a F protein or H protein of a morbillivirus.
22. A method of in vivo gene delivery comprising administering an engineered viral particle to a subject in need of delivery, wherein the engineered viral particle comprises
    i. an engineered envelope harboring a mutated fusion protein, a chimeric gag protein and an engineered targeting moiety for binding to a target cell, wherein the mutated fusion protein does not bind to its natural receptor; and
    ii. a nucleic acid encoding a polypeptide of interest
    iii. wherein the administration of the engineered viral particle induces an in vivo activity in the target cell associated with the polypeptide of interest.
23. The method of embodiment 22, wherein the chimeric gag protein is xHIV gag protein.
24. The method of embodiments 22 or 23, wherein the viral particle further comprises a nucleotide sequence encoding a SIV element, and/or a Pol protein.
25. The method of embodiment 23, wherein the xHIV gag protein is encoded by the nucleic acid sequence as set forth in SEQ ID NO: 5.
26. The method of embodiment 23, wherein the xHIV gag protein is encoded by the nucleic acid sequence as set forth in SEQ ID NO: 6.
27. The method of embodiment 24, wherein the SIV element is encoded by the nucleic acid sequence as set forth in SEQ ID NO: 7.
28. The method of embodiment 24, wherein the Pol protein is encoded by the nucleic acid sequence as set forth in SEQ ID NO: 8.
29. The method of embodiment 23, wherein the xHIV gag protein comprises an amino acid sequence as set forth in SEQ ID NO: 9.
30. The method of embodiment 24, wherein the Pol protein comprises an amino acid sequence as set forth in SEQ ID NO: 10.
31. The method of any one of embodiments 22-30, wherein the target cell is a T cell, a CD4+ T cell, a CD8+ T cell, a NK cell, an alpha-beta T cell, a gamma-delta T cell, a lymphoid progenitor cell, a hematopoietic stem cell, a myeloid cell, a monocyte, a macrophage, a central memory T cell, a naïve T cell, an activated T cell, a regulatory T Cell (Treg), or a T-Cell$^{CD8+CCR7+}$
32. A cell comprising the polypeptide of interest encoded for by the engineered viral particle of any one of embodiments 1-21.

33. The cell of embodiment 32, wherein the cell is a T cell, a CD4+ T cell, a CD8+ T cell, a NK cell, an alpha-beta T cell, a gamma-delta T cell, a lymphoid progenitor cell, a hematopoietic stem cell, a myeloid cell, a monocyte, a macrophage, a central memory T cell, a naïve T cells, an activated T cell, or a regulatory T Cell (Treg), or a T-Cell$^{CD8+CCR7+}$
34. A method of treating a disease in a subject, the method comprising administering to the subject the engineered viral particle of any one of embodiments 1-21, wherein the engineered viral particle expresses the polypeptide of interest in a cell.
35. The method of embodiment 34, wherein the disease is cancer or sickle cell disease.
36. The method of embodiments 34 or 35, wherein the cell is a T cell, a CD4+ T cell, a CD8+ T cell, a NK cell, an alpha-beta T cell, a gamma-delta T cell, a lymphoid progenitor cell, a hematopoietic stem cell, a myeloid cell, a monocyte, a macrophage, a central memory T cell, a naïve T cells, an activated T cell, a regulatory T Cell (Treg), or a T-Cell$^{CD8+CCR7+}$
37. A viral vector system comprising a first viral particle and a second viral particle, wherein:
    a.) the first viral particle comprises a chimeric gag protein, a first targeting moiety that binds to a first target on a cell and a first nucleic acid molecule that encodes a first portion of a protein or a polypeptide of interest;
    b.) the second viral particle comprises a chimeric gag protein, a second targeting moiety that binds to a second target on the cell and a second nucleic acid molecule that encodes a second portion of the protein or the polypeptide of interest,
    c.) wherein the first and second portions of the protein or the polypeptide are capable of forming a complete protein or polypeptide of interest inside the cell.
38. The viral vector system of embodiment 23, wherein the chimeric gag protein is xHIV gag protein.
39. The viral vector system of embodiments 37 or 38, wherein the viral particle further comprises nucleotide sequence encoding a SIV element, and/or a Pol protein.
40. The viral vector system of embodiment 38, wherein the xHIV gag protein is encoded by the nucleic acid sequence as set forth in SEQ ID NO: 5.
41. The viral vector system of embodiment 38, wherein the xHIV gag protein is encoded by the nucleic acid sequence as set forth in SEQ ID NO: 6.
42. The viral vector system of embodiment 39, wherein the SIV element is encoded by the nucleic acid sequence as set forth in SEQ ID NO: 7.
43. The viral vector system of embodiment 39, wherein the Pol protein is encoded by the nucleic acid sequence as set forth in SEQ ID NO: 8.
44. The viral vector system of embodiment 38, wherein the xHIV gag protein comprises an amino acid sequence as set forth in SEQ ID NO: 9.
45. The viral vector system of embodiment 39, wherein the Pol protein comprises an amino acid sequence as set forth in SEQ ID NO: 10.
46. The viral vector system of any one of embodiments 37-45, wherein the first target and the second target are different.
47. The viral vector system any one of embodiments 37-45, wherein the protein or polypeptide of interest is a chimeric antigen receptor.
48. The viral vector system of embodiment 47, wherein the chimeric antigen receptor comprises an extracellular domain, transmembrane domain, and an intracellular signaling domain.
49. The viral vector system of embodiment 48, wherein the extracellular domain binds to CD20, CD22, CD123, CD38, CD19, BCMA, CD33, or CD79b.
50. The viral vector system of any one of embodiments embodiment 37-45, wherein the protein or polypeptide is a hemoglobin beta chain.
51. The viral vector system of any one of embodiments 37-50, wherein the first targeting moiety and the second targeting moiety are each independently selected from the group consisting of a protein that binds to the first target, an antigen binding domain, a DARPIN, and a FN3 domain, or any combination thereof.
52. The viral vector system of any one of embodiments 37-51, wherein the first targeting moiety and the second targeting moiety are each independently selected from the group consisting of Stem Cell Factor protein (SCF, KIT-ligand, KL, or steel factor) or a moiety that binds to cKit (CD117), CD4, CD8, CD3, CD5, CD6, CD7, CD2, TCR alpha, TCR beta, TCR gamma, TCR delta, CD10, CD34, CD110, CD33, CD14, CD68, CCR7, CD62L, CD25, CCR2, CCR3, CCR4, CCR5, CCR6, CCR7, and CXCR3.
53. The viral vector system of embodiment 52, wherein the first targeting moiety is selected from the group consisting of Stem Cell Factor protein (SCF, KIT-ligand, KL, or steel factor) or a moiety that binds to cKit (CD117), CD4, CD8, CD3, CD5, CD6, CD7, CD2, TCR alpha, TCR beta, TCR gamma, TCR delta, CD10, CD34, CD110, CD33, CD14, or CD68.
54. The viral vector system of embodiments 52 or 53, wherein the second targeting moiety binds to CCR7, CD62L, CD25, CCR2, CCR3, CCR4, CCR5, CCR6, CCR7, or CXCR3.
55. The viral vector system of any one of embodiments 37-51, wherein the first target and the second target are each independently selected from the group consisting of cKit (CD117), CD4, CD8, CD3, CD5, CD6, CD7, CD2, TCR alpha, TCR beta, TCR gamma, TCR delta, CD10, CD34, CD110, CD33, CD14, CD68, CCR7, CD62L, CD25, CCR2, CCR3, CCR4, CCR5, CCR6, CCR7, and CXCR3.
56. The viral vector system of any one of embodiments 37-55, wherein the first target is cKit (CD117), CD4, CD8, CD3, CD5, CD6, CD7, CD2, TCR alpha, TCR beta, TCR gamma, TCR delta, CD10, CD34, CD110, CD33, CD14, or CD68.
57. The viral vector system of any one of embodiments 37-56, wherein the second target is CCR7, CD62L, CD25, CCR2, CCR3, CCR4, CCR5, CCR6, CCR7, or CXCR3.
58. The viral vector system of any one of embodiments 37-57, wherein the first viral vector is a pseudotyped viral vector.
59. The viral vector system of any one of embodiments 37-58, wherein the second viral vector is a pseudotyped viral vector.
60. The viral vector system of any one of embodiments 37-59, wherein the first and second viral vector are each, independently, a pseudotyped lentiviral vector, an adenovirus, or an adeno-associated virus.
61. The viral vector system of embodiment 60, wherein the pseudotyped lentiviral vector is pseudotyped with a morbillivirus, such as a measles virus, glycoprotein and/or a Nipah virus glycoprotein.

62. The viral vector system of embodiment 60, wherein the first and/or second viral vector is pseudotyped with a F protein or H protein of a morbillivirus.
63. The viral vector system of any one of embodiments 37-62, wherein the cell is a T cell, a CD4+ T cell, a CD8+ T cell, a NK cell, an alpha-beta T cell, a gamma-delta T cell, a lymphoid progenitor cell, a hematopoietic stem cell, a myeloid cell, a monocyte, a macrophage, a central memory T cell, a naïve T cell, an activated T cell, a regulatory T Cell (Treg), or a T-Cell$^{CD8+CCR7+}$
64. The viral vector system of any one of embodiments 37-63, wherein the first and second portions of the protein or polypeptide form a complete protein in the presence of a dimerizing agent.
65. The viral vector system of any one of embodiments 37-63, wherein the protein or polypeptide is a chimeric antigen receptor or a hemoglobin beta chain.
66. The viral vector system of embodiments 64 or 65, wherein the dimerizing agent is rimiducid ((1R)-3-(3,4-dimethoxyphenyl)-1-[3-({[2-(2-{3-[(1R)-3-(3,4-dimethoxyphenyl)-1-[(2S)-1-[(2S)-2-(3,4,5-trimethoxyphenyl)butanoyl]piperidine-2-carbonyloxy]propyl]phenoxy}acetamido)ethyl]carbamoyl}methoxy)phenyl]propyl (2S)-1-[(2S)-2-(3,4,5-trimethoxyphenyl)butanoyl]piperidine-2-carboxylate (AP1903)), erythropoietin, or rapamycin.
67. The viral vector system of any one of embodiments embodiment 37-63, wherein the first and second portions of the protein or polypeptide can bind together through the excision of an intein domain.
68. The viral vector system of any one of embodiments embodiment 37-45, wherein the first portion of the protein comprises an extracellular domain of a chimeric antigen receptor and the second portion of the protein comprises the transmembrane domain, and an intracellular signaling domain.
69. A cell comprising the viral vector system of any one of embodiments 37-68.
70. The cell of any one of embodiment 69, wherein the cell is a T cell, a CD4+ T cell, a CD8+ T cell, a NK cell, an alpha-beta T cell, a gamma-delta T cell, a lymphoid progenitor cell, a hematopoietic stem cell, a myeloid cell, a monocyte, a macrophage, a central memory T cell, a naïve T cells, an activated T cell, or a regulatory T Cell (Treg), or a T-Cell$^{CD8+CCR7+}$
71. A method of in vivo gene delivery comprising administering to a subject in need of thereof a first viral particle and a second viral particle, wherein:
    a.) the first viral particle comprises a chimeric gag protein, a first targeting moiety that binds to a first target on a cell and a first nucleic acid molecule that encodes a first portion of a protein or a polypeptide of interest;
    b.) the second viral particle comprises a chimeric gag protein, a second targeting moiety that binds to a second target on the cell and a second nucleic acid molecule that encodes a second portion of the protein or the polypeptide of interest,
    c.) wherein the first and second portions of the protein or the polypeptide are capable of forming a complete protein or polypeptide of interest inside the cell.
72. The method of embodiment 71, wherein the chimeric gag protein is xHIV gag protein.
73. The method of embodiment 71, further comprising administering a dimerizing agent to form the protein or polypeptide in the subject.
74. The method of embodiment 71, wherein the first portion and the second portion comprise an intein domain and the intein domain is excised to conjugate the first and second portion to form the protein or polypeptide.
75. The method of embodiment 71, wherein the cell is a T cell, a CD4+ T cell, a CD8+ T cell, a NK cell, an alpha-beta T cell, a gamma-delta T cell, a lymphoid progenitor cell, a hematopoietic stem cell, a myeloid cell, a monocyte, a macrophage, a central memory T cell, a naïve T cells, an activated T cell, a regulatory T Cell (Treg), or a CD8+naïve/central memory cell (CD8+CCR7+) and CD4+naïve/central memory cell (CD4+CCR7+).
76. The method of any one of embodiments 71-75, wherein the protein or polypeptide is a chimeric antigen receptor.
77. The method of any one of embodiments 71-75, wherein the protein or polypeptide is a hemoglobin beta chain.
78. The method of any one of embodiments 71-77, wherein the first viral vector is a pseudotyped viral vector.
79. The method of any one of embodiments 71-78, wherein the second viral vector is a pseudotyped viral vector.
80. The method of any one of embodiments 71-79, wherein the first and second viral vector are each, independently, a pseudotyped lentiviral vector, an adenovirus, or an adeno-associated virus.
81. The method of embodiment 80, wherein the pseudotyped lentiviral vector is pseudotyped with a morbillivirus or a henipavirus, such as a measles virus, glycoprotein and/or a Nipah virus glycoprotein.
82. The method of embodiment 80, wherein the first and/or second viral vector is pseudotyped with a F protein or H protein of a morbillivirus.
83. A method of treating a disease in a subject, the method comprising administering to the subject a first viral particle and a second viral particle, wherein:
    a.) the first viral particle comprises a chimeric gag protein, a first targeting moiety that binds to a first target on a cell and a first nucleic acid molecule that encodes a first portion of a protein or a polypeptide of interest;
    b.) the second viral particle comprises a chimeric gag protein, a second targeting moiety that binds to a second target on the cell and a second nucleic acid molecule that encodes a second portion of the protein or the polypeptide of interest,
    c.) wherein the first and second portions of the protein or the polypeptide are capable of forming a complete protein or polypeptide of interest inside the cell.
84. The method of embodiment 83, wherein the disease is cancer or sickle cell disease.
85. The method of embodiments 83 or 84, further comprising administering a dimerizing agent to form the protein or polypeptide in the cell.
86. The method of embodiments 83 or 84, wherein the first portion and the second portion comprise an intein domain and the intein domain is excised to conjugate the first and second portion to form the protein or polypeptide.

87. The method of any one of embodiments 83-86, wherein the cell is a T cell, a CD4+ T cell, a CD8+ T cell, a NK cell, an alpha-beta T cell, a gamma-delta T cell, a lymphoid progenitor cell, a hematopoietic stem cell, a myeloid cell, a monocyte, a macrophage, a central memory T cell, a naïve T cells, an activated T cell, a regulatory T Cell (Treg), or a T-Cell$^{CD8+CCR7+}$
88. The method of any one of embodiments 83-87, wherein the protein or polypeptide is a chimeric antigen receptor.
89. The method of any one of embodiments 83-87, wherein the protein or polypeptide is a hemoglobin beta chain.
90. The method of any one of embodiments 83-89, wherein the first viral vector is a pseudotyped viral vector.
91. The method of any one of embodiments 83-90, wherein the second viral vector is a pseudotyped viral vector.
92. The method of any one of embodiments 83-91, wherein the first and second viral vector are each, independently, a pseudotyped lentiviral vector, an adenovirus, or an adeno-associated virus.
93. The method of embodiment 92, wherein the pseudotyped lentiviral vector is pseudotyped with a morbillivirus, such as a measles virus, glycoprotein and/or a Nipah virus glycoprotein.
94. The method of embodiment 93, wherein the first and/or second viral vector is pseudotyped with a F protein or H protein of a morbillivirus.
95. An engineered viral particle comprising an engineered envelope comprising a mutated fusion protein and an engineered targeting moiety for binding to a target cell, wherein the mutated fusion protein does not bind to its natural receptor; and a nucleic acid molecule encoding a polypeptide of interest.
96. The engineered viral particle of embodiment 95, wherein the targeting moiety is fused to the mutated fusion protein.
97. The engineered viral particle of embodiments 95 or 96, wherein the viral particle is a lentivirus pseudotyped with a measles virus (MV) hemagglutinin (HA) protein or an MV fusion (F) protein or a Nipah virus F or G protein, a.) wherein the MV-HA protein, the MV-F protein, the Nipah virus F, or the Nipah virus G protein comprises a mutated binding domain compared to its naturally occurring receptor.
98. The engineered viral particle of embodiment 97, wherein the targeting moiety is fused to the MV-HA protein, the MV-F protein, the Nipah virus F, or the Nipah virus G protein.
99. The engineered viral particle of any one of embodiments 95-98, wherein the targeting moiety is a scFv, an antigen binding domain, a DARPIN, a FN3 domain, a VHH, or any combination thereof.
100. The engineered viral particle of any one embodiments 95-99, wherein the targeting moiety is selected from the group consisting of Stem Cell Factor protein (SCF, KIT-ligand, KL, or steel factor) or a moiety that binds to cKit (CD117), CD4, CD8, CD3, CD5, CD6, CD7, CD2, TCR alpha, TCR beta, TCR gamma, TCR delta, CD10, CD34, CD110, CD33, CD14, CD68, CCR7, CD62L, CD25, CCR2, CCR3, CCR4, CCR5, CCR6, CCR7, and CXCR3.
101. The engineered viral particle of any one embodiments 95-100, wherein the polypeptide of interest is a chimeric antigen receptor (CAR) or a portion thereof.
102. The engineered viral particle of embodiment 101, wherein the chimeric antigen receptor comprises an extracellular domain, transmembrane domain, and an intracellular signaling domain.
103. The engineered viral particle of embodiment 102, wherein the extracellular domain binds to CD20, CD22, CD123, CD38, CD19, BCMA, CD33, or CD79b.
104. The engineered viral particle of embodiment 95, wherein the polypeptide of interest is a hemoglobin beta chain.
105. The engineered viral particle of any one of embodiments 95-104, wherein the viral particle is a pseudotyped lentiviral vector, an adenovirus, or an adeno-associated virus.
106. The engineered viral particle of embodiment 105, wherein the pseudotyped lentiviral vector is pseudotyped with a morbillivirus or henipavirus, such as a measles virus, glycoprotein and/or a Nipah virus glycoprotein.
107. The engineered viral particle of embodiment 106, wherein the pseudotyped vector is pseudotyped with a F protein and/or H protein of a morbillivirus or a F protein and/or a G protein of a henipavirus.
108. A method of in vivo gene delivery comprising administering an engineered viral particle to a subject in need of delivery, wherein the engineered viral particle is a particle of any one of embodiments 95-108, wherein the administration of the engineered viral particle induces an in vivo activity in a target cell associated with the polypeptide of interest.
109. The method of embodiment 108, wherein the target cell is a T cell, a CD4+ T cell, a CD8+ T cell, a NK cell, an alpha-beta T cell, a gamma-delta T cell, a lymphoid progenitor cell, a hematopoietic stem cell, a myeloid cell, a monocyte, a macrophage, a central memory T cell, a naïve T cell, an activated T cell, a regulatory T Cell (Treg), or a T-Cell$^{CD8+CCR7+}$
110. A cell comprising the polypeptide of interest encoded for by the engineered viral particle of any one of embodiments 95-108.
111. The cell of embodiment 110, wherein the cell is a T cell, a CD4+ T cell, a CD8+ T cell, a NK cell, an alpha-beta T cell, a gamma-delta T cell, a lymphoid progenitor cell, a hematopoietic stem cell, a myeloid cell, a monocyte, a macrophage, a central memory T cell, a naïve T cells, an activated T cell, or a regulatory T Cell (Treg), or a T-Cell$^{CD8+CCR7+}$
112. A method of treating a disease in a subject, the method comprising administering to the subject the engineered viral particle of any one of embodiments 95-108, wherein the engineered viral particle expresses the polypeptide of interest in a cell.
113. The method of embodiment 112, wherein the disease is cancer or sickle cell disease.
114. The method of embodiments 112 or 113, wherein the cell is a T cell, a CD4+ T cell, a CD8+ T cell, a NK cell, an alpha-beta T cell, a gamma-delta T cell, a lymphoid progenitor cell, a hematopoietic stem cell, a myeloid cell, a monocyte, a macrophage, a central memory T cell, a naïve T cells, an activated T cell, a regulatory T Cell (Treg), or a T-Cell$^{CD8-CCR7+}$
115. An engineered viral particle comprising:
  i. an engineered envelope comprising a polypeptide having the amino acid sequence of SEQ ID NO: 9;
  ii. a heterologous polypeptide targeting moiety for binding to a target cell; and iii. a nucleic acid molecule encoding a heterologous polypeptide of interest.

116. The engineered viral particle of embodiment 115, wherein the targeting moiety is 116 fused to a mutated fusion protein present on the surface of the engineered viral particle.

117. The engineered viral particle of embodiment 115, wherein the viral particle is a lentivirus pseudotyped with:

a) a measles virus (MV) hemagglutinin (HA) protein and/or an MV fusion (F) protein and wherein the MV-HA protein or the MV-F protein comprises a mutation or a mutated binding domain compared to its naturally occurring protein; or b) a Nipah virus F protein and/or a Nipah virus G protein and wherein the a Nipah virus F protein and/or a Nipah virus G protein comprises a mutation or a mutated binding domain compared to its naturally occurring protein 118. The engineered viral particle of embodiment 115, wherein the targeting moiety is fused to the MV-HA protein and/or the MV-F protein or the Nipah virus F protein and/or a Nipah virus G protein.

119. The engineered viral particle of embodiment 115, wherein the targeting moiety is a scFv, an antigen binding domain, a DARPIN, a VHH, or a FN3 domain.

120. The engineered viral particle of embodiment 115, wherein the targeting moiety binds to protein selected from the group consisting of Stem Cell Factor protein (SCF, KIT-ligand, KL, or steel factor) or a moiety that binds to cKit (CD1 17), CD4, CD8, CD3, CD3D, CD3E, CD3G, CD3Z, CD5, CD6, CD7, CD2, TCR alpha, TCR beta, TCR gamma, TCR delta, CD10, CD34, CD110, CD33, CD14, CD68, CCR7, CD62L, CD25, CCR2, CCR3, CCR4, CCR5, CCR6, CCR7, and CXCR3.

121. The engineered viral particle of embodiment 115, wherein the heterologous polypeptide of interest is a chimeric antigen receptor (CAR).

122. The engineered viral particle of embodiment 121, wherein the chimeric antigen receptor comprises an extracellular domain, transmembrane domain, and an intracellular signaling domain.

123. The engineered viral particle of embodiment 122, wherein the extracellular domain binds to CD20, CD22, CD123, CD38, CD19, BCMA, CD33, or CD79b.

124. The engineered viral particle of embodiment 115, wherein the heterologous polypeptide of interest is a hemoglobin beta chain.

125. The engineered viral particle of embodiment 115, wherein the viral particle is a pseudotyped lentiviral vector, an adenovirus, or an adeno-associated virus.

126. The engineered viral particle of embodiment 125, wherein the pseudotyped lentiviral vector is pseudotyped with a morbillivirus or a henipavirus.

127. The engineered viral particle of embodiment 126, wherein the morbillivirus is a measles virus.

128. The engineered viral particle of embodiment 126, wherein the henipavirus is a Nipah virus.

129. The engineered viral particle of embodiment 125, wherein the pseudotyped lentiviral vector comprises a morbillivirus F protein and/or H protein.

130. The engineered viral particle of embodiment 129, wherein the morbillivirus F protein and/or H protein is a measles F protein and/or H protein.

131. The engineered viral particle of embodiment 130, wherein the measles F protein comprises the amino acid sequence of SEQ ID NO: 11 and the measles H protein comprises the amino acid sequence of SEQ ID NO: 12.

132. The engineered viral particle of embodiment 125, wherein the pseudotyped lentiviral vector comprises a henipavirus F protein and/or G protein.

133. The engineered viral particle of embodiment 132, wherein the henipavirus G protein is a Nipah G protein and the henipavirus F protein is a Nipah F protein 134. The engineered viral particle of embodiment 133, wherein the Nipah F protein comprises the amino acid sequence of SEQ ID NO: 13 and the Nipah G protein comprises the amino acid sequence of SEQ ID NO: 14.

135. A method of delivering a nucleic acid molecule encoding a heterologous protein of interest to a cell, the method comprising contacting the engineered viral particle of embodiment 115 to a cell, thereby delivering the nucleic acid molecule encoding the heterologous protein of interest to the cell.

136. The method of embodiment 135, wherein the contacting comprises administering the engineered viral particle of embodiment 1 to a subject to deliver the nucleic acid molecule encoding the heterologous protein of interest to a cell in vivo.

137. The method of embodiment 135, wherein the cell is contacted with the engineered viral particle of embodiment ex vivo.

138. A viral vector system comprising a first viral particle and a second viral particle, wherein:

a.) the first viral particle comprises a first targeting moiety that binds to a first target on a cell and a first nucleic acid molecule that encodes a first portion of a protein or a polypeptide of interest;

b.) the second viral particle comprises a second targeting moiety that binds to a second target on the cell and a second nucleic acid molecule that encodes a second portion of the protein or the polypeptide of interest, wherein the first and second portions of the protein or the polypeptide are capable of forming a complete protein or polypeptide of interest inside the cell.

139. The viral vector system of embodiment 138, wherein the first target and the second target are different.

140. The viral vector system of embodiment 138, wherein the protein or polypeptide of interest is a chimeric antigen receptor.

141. The viral vector system of embodiment 139, wherein the chimeric antigen receptor comprises an extracellular domain, transmembrane domain, and an intracellular signaling domain.

142 The viral vector system of embodiment 141, wherein the extracellular domain binds to CD20, CD22, CD123, CD38, CD19, BCMA, CD33, or CD79b.

143. The viral vector system of embodiment 138, wherein the protein or polypeptide is a hemoglobin beta chain.

144. The viral vector system of any one of embodiments 138-143, wherein the first targeting moiety and the second targeting moiety are each independently selected from the group consisting of a protein that binds to the first target, an antigen binding domain, a DARPIN, a VHH, a scFV, and a FN3 domain, or any combination thereof.

145. The viral vector system of any one of embodiments 138-144, wherein the first targeting moiety and the second targeting moiety are each independently selected from the group consisting of Stem Cell Factor protein (SCF, KIT-ligand, KL, or steel factor) or a moiety that binds to cKit (CD117), CD4, CD8, CD3, CD5, CD6, CD7, CD2, TCR alpha, TCR beta, TCR gamma, TCR delta, CD10, CD34, CD110, CD33, CD14, CD68, CCR7, CD62L, CD25, CCR2, CCR3, CCR4, CCR5, CCR6, CCR7, and CXCR3.

146. The viral vector system of embodiment 145, wherein the first targeting moiety is selected from the group consisting of Stem Cell Factor protein (SCF, KIT-ligand, KL, or steel factor) or a moiety that binds to cKit (CD117), CD4, CD8, CD3, CD5, CD6, CD7, CD2, TCR alpha, TCR beta, TCR gamma, TCR delta, CD10, CD34, CD110, CD33, CD14, or CD68.

147. The viral vector system of embodiments 145 or 146, wherein the second targeting moiety binds to CCR7, CD62L, CD25, CCR2, CCR3, CCR4, CCR5, CCR6, CCR7, or CXCR3.

148. The viral vector system of any one of embodiments 138-145, wherein the first target and the second target are each independently selected from the group consisting of cKit (CD117), CD4, CD8, CD3, CD5, CD6, CD7, CD2, TCR alpha, TCR beta, TCR gamma, TCR delta, CD10, CD34, CD110, CD33, CD14, CD68, CCR7, CD62L, CD25, CCR2, CCR3, CCR4, CCR5, CCR6, CCR7, and CXCR3.

149. The viral vector system of any one of embodiments 138-148, wherein the first target is cKit (CD117), CD4, CD8, CD3, CD5, CD6, CD7, CD2, TCR alpha, TCR beta, TCR gamma, TCR delta, CD10, CD34, CD110, CD33, CD14, or CD68.

150. The viral vector system of any one of embodiments 138-149, wherein the second target is CCR7, CD62L, CD25, CCR2, CCR3, CCR4, CCR5, CCR6, CCR7, or CXCR3.

151. The viral vector system of any one of embodiments 138-150, wherein the first viral vector is a pseudotyped viral vector.

152. The viral vector system of any one of embodiments 138-151, wherein the second viral vector is a pseudotyped viral vector.

153. The viral vector system of any one of embodiments 138-152, wherein the first and second viral vector are each, independently, a pseudotyped lentiviral vector, an adenovirus, or an adeno-associated virus.

154. The viral vector system of embodiment 153, wherein the pseudotyped lentiviral vector is pseudotyped with a morbillivirus or henipavirus, such as a measles virus H protein or glycoprotein and/or a Nipah virus F protein and/or G protein.

155. The viral vector system of embodiment 154, wherein the first and/or second viral vector is pseudotyped with a F protein or H protein of a morbillivirus.

156. The viral vector system of any one of embodiments 138-155, wherein the cell is a T cell, a CD4+ T cell, a CD8+ T cell, a NK cell, an alpha-beta T cell, a gamma-delta T cell, a lymphoid progenitor cell, a hematopoietic stem cell, a myeloid cell, a monocyte, a macrophage, a central memory T cell, a naïve T cell, an activated T cell, a regulatory T Cell (Treg), or a T-Cell$^{CD8+CCR7+}$ 157. The viral vector system of any one of embodiments 138-156, wherein the first and second portions of the protein or polypeptide form a complete protein in the presence of a dimerizing agent.

158. The viral vector system of any one of embodiments 138-157, wherein the protein or polypeptide is a chimeric antigen receptor or a hemoglobin beta chain.

159. The viral vector system of embodiments 157 or 158, wherein the dimerizing agent is rimiducid ((1R)-3-(3,4-dimethoxyphenyl)-1-[3-({[2-(2-{3-[(1R)-3-(3,4-dimethoxyphenyl)-1-[(2S)-1-[(2S)-2-(3,4,5-trimethoxyphenyl)butanoyl]piperidine-2-carbonyloxy]propyl]phenoxy}acetamido)ethyl]carbamoyl}methoxy)phenyl]propyl (2S)-1-[(2S)-2-(3,4,5-trimethoxyphenyl)butanoyl]piperidine-2-carboxylate (AP1903)), erythropoietin, or rapamycin.

160. The viral vector system of any one of embodiments embodiment 138-156, wherein the first and second portions of the protein or polypeptide can bind together through the excision of intein domain.

161. The viral vector system of embodiment 138, wherein the first portion of the protein comprises an extracellular domain of a chimeric antigen receptor and the second portion of the protein comprises the transmembrane domain, and an intracellular signaling domain.

162. A cell comprising a first nucleic acid molecule that encodes a first portion of a chimeric antigen receptor and a second nucleic acid molecule that encodes a second portion of the chimeric antigen receptor, wherein the first portion of the chimeric antigen receptor and the second portion of the chimeric antigen receptor are capable of binding to one another to form a complete chimeric antigen receptor in the presence of a dimerizing agent or dimerizing domain.

163. The cell of embodiment 162, wherein the dimerizing agent is rimiducid ((1R)-3-(3,4-dimethoxyphenyl)-1-[3-({[2-(2-{3-[(1R)-3-(3,4-dimethoxyphenyl)-1-[(2S)-1-[(2S)-2-(3,4,5-trimethoxyphenyl)butanoyl]piperidine-2-carbonyloxy]propyl]phenoxy}acetamido)ethyl]carbamoyl}methoxy)phenyl]propyl (2S)-1-[(2S)-2-(3,4,5-trimethoxyphenyl)butanoyl]piperidine-2-carboxylate (AP1903)), erythropoietin, or rapamycin.

164. The cell of embodiment 163, wherein the dimerizing domain is an intein domain. 165. A cell comprising a first nucleic acid molecule that encodes a first portion of a protein or polypeptide and a second nucleic acid molecule that encodes a second portion of the protein or the polypeptide, wherein the first and second portions of the protein or the polypeptide can bind together to form a complete protein or polypeptide.

166. The cell of embodiment 165, wherein the protein or polypeptide is a hemoglobin beta chain.

167. The cell of embodiment 165, wherein the protein or polypeptide is a heterologous chimeric antigen receptor, wherein the heterologous chimeric antigen chimer receptor comprises a first portion of the chimeric antigen receptor and a second portion of the chimeric antigen receptor, wherein the first portion and the second portion bind to one another to form the chimeric antigen receptor through a dimerizing agent or dimerizing domain, such as an intein domain.

168. The cell of any one of embodiments 165-167, wherein the cell is a T cell, a CD4+ T cell, a CD8+ T cell, a NK cell, an alpha-beta T cell, a gamma-delta T cell, a lymphoid progenitor cell, a hematopoietic stem cell, a myeloid cell, a monocyte, a macrophage, a central memory T cell, a naïve T cells, an activated T cell, or a regulatory T Cell (Treg), or a T-Cell$^{CD8+CCR7+}$ 169. A method of in vivo or ex vivo gene delivery comprising administering to a subject in need of delivery a first viral particle and a second viral particle, wherein:
   a.) the first viral particle comprises a first targeting moiety that binds to a first target on a cell and a first nucleic acid molecule that encodes a first portion of a protein or polypeptide of interest;
   b.) the second viral particle comprises a second targeting moiety that binds to a second target on the cell and a second nucleic acid molecule that encodes a second portion of the protein or the polypeptide of interest,
   wherein the first and second portions of the protein or the polypeptide are capable of forming a complete protein or polypeptide inside the cell.
170. The method of embodiment 169, further comprising administering a dimerizing agent to form the protein or polypeptide in the subject.
171. The method of embodiment 169, wherein the first portion and the second portion comprise an intein domain and the intein domain is excised to conjugate the first and second portion to form the protein or polypeptide.
172. The method of embodiment 169, wherein the cell is a T cell, a CD4+ T cell, a CD8+ T cell, a NK cell, an alpha-beta T cell, a gamma-delta T cell, a lymphoid progenitor cell, a hematopoietic stem cell, a myeloid cell, a monocyte, a macrophage, a central memory T cell, a naïve T cells, an activated T cell, a regulatory T Cell (Treg), or a CD8+naïve/central memory cell (CD8+CCR7+) and CD4+naïve/central memory cell (CD4+CCR7+).
173. The method of any one of embodiments 169-172, wherein the protein or polypeptide is a chimeric antigen receptor.
174. The method of any one of embodiments 169-172 wherein the protein or polypeptide is a hemoglobin beta chain.
175. The method of any one of embodiments 169-174, wherein the first viral vector is a pseudotyped viral vector.
176. The method of any one of embodiments 169-175, wherein the second viral vector is a pseudotyped viral vector.
177. The method of any one of embodiments 169-176, wherein the first and second viral vector are each, independently, a pseudotyped lentiviral vector, an adenovirus, or an adeno-associated virus.
178. The method of embodiment 177, wherein the pseudotyped lentiviral vector is pseudotyped with a morbillivirus or a henipavirus, such as a measles virus, glycoprotein and/or a Nipah virus glycoprotein.
179. The method of embodiment 178, wherein the first and/or second viral vector is pseudotyped with a F protein or H protein of a morbillivirus or a F protein or G protein of a henipavirus.
180. A method of treating a disease in a subject, the method comprising administering to the subject a first viral particle and a second viral particle, wherein:
   a.) the first viral particle comprises a first targeting moiety that binds to a first target on a cell and a first nucleic acid molecule that encodes a first portion of a protein or polypeptide of interest;
   b.) the second viral particle comprises a second targeting moiety that binds to a second target on the cell and a second nucleic acid molecule that encodes a second portion of the protein or the polypeptide of interest,
   wherein the first and second portions of the protein or the polypeptide are capable of forming a complete protein or polypeptide in the cell to treat the disease.
181. The method of embodiment 180, wherein the disease is cancer or sickle cell disease.
182. The method of embodiments 180 or 181, further comprising administering a dimerizing agent to form the protein or polypeptide in the cell.
183. The method of any one of embodiments 180-182, wherein the first portion and the second portion comprise an intein domain and the intein domain is excised to conjugate the first and second portion to form the protein or polypeptide.
184 The method of embodiments any one of embodiments 180-183, wherein the cell is a T cell, a CD4+ T cell, a CD8+ T cell, a NK cell, an alpha-beta T cell, a gamma-delta T cell, a lymphoid progenitor cell, a hematopoietic stem cell, a myeloid cell, a monocyte, a macrophage, a central memory T cell, a naïve T cells, an activated T cell, a regulatory T Cell (Treg), or a T-Cell$^{CD8+CCR7+}$
185. The method of any one of embodiments 180-184, wherein the protein or polypeptide is a chimeric antigen receptor.
186. The method of any one of embodiments 180-184 wherein the protein or polypeptide is a hemoglobin beta chain.
187. The method of any one of embodiments 180-186, wherein the first viral vector is a pseudotyped viral vector.
188. The method of any one of embodiments 180-187, wherein the second viral vector is a pseudotyped viral vector.
189. The method of any one of embodiments 180-188, wherein the first and second viral vector are each, independently, a pseudotyped lentiviral vector, an adenovirus, or an adeno-associated virus.
190. The method of embodiment 189, wherein the pseudotyped lentiviral vector is pseudotyped with a morbillivirus, such as a measles virus, glycoprotein and/or a Nipah virus glycoprotein.
191. The method of embodiment 190, wherein the first and/or second viral vector is pseudotyped with a F protein and/or H protein of a morbillivirus or a F protein and/or a G protein of a henipavirus.

The contents of the articles, patents, and patent applications, and all other documents and electronically available information mentioned or cited herein, are hereby incorporated by reference in their entirety to the same extent as if each individual publication was specifically and individually indicated to be incorporated by reference. Applicants reserve the right to physically incorporate into this application any and all materials and information from any such articles, patents, patent applications, or other physical and electronic documents.

While the present invention has been described with reference to the specific embodiments thereof, it should be understood by those skilled in the art that various changes may be made and equivalents may be substituted without departing from the true spirit and scope of the invention. It will be readily apparent to those skilled in the art that other suitable modifications and adaptations of the methods described herein may be made using suitable equivalents without departing from the scope of the embodiments disclosed herein. In addition, many modifications may be made to adapt a particular situation, material, composition of matter, process, process step or steps, to the objective, spirit and scope of the present invention. All such modifications are intended to be within the scope of the claims appended hereto. Having now described certain embodiments in detail, the same will be more clearly understood by reference to the following examples, which are included for purposes of illustration only and are not intended to be limiting.

EXAMPLES

The embodiments are now described with reference to the following Examples. These Examples are provided for the purpose of illustration only, and the embodiments are not limited to these Examples, but rather encompasses all variations that are evident as a result of the teachings provided herein.

Example 1

Pseudotyped Viral Vector System Containing Chimeric Gag

The present disclosure is, in part, based on the finding that substituting xHIV gag protein, a chimeric gag protein from SIV, for the HIV gag protein found in standard pseudotyped lentiviral vectors, enhances transduction efficiency.

Figure 1B:
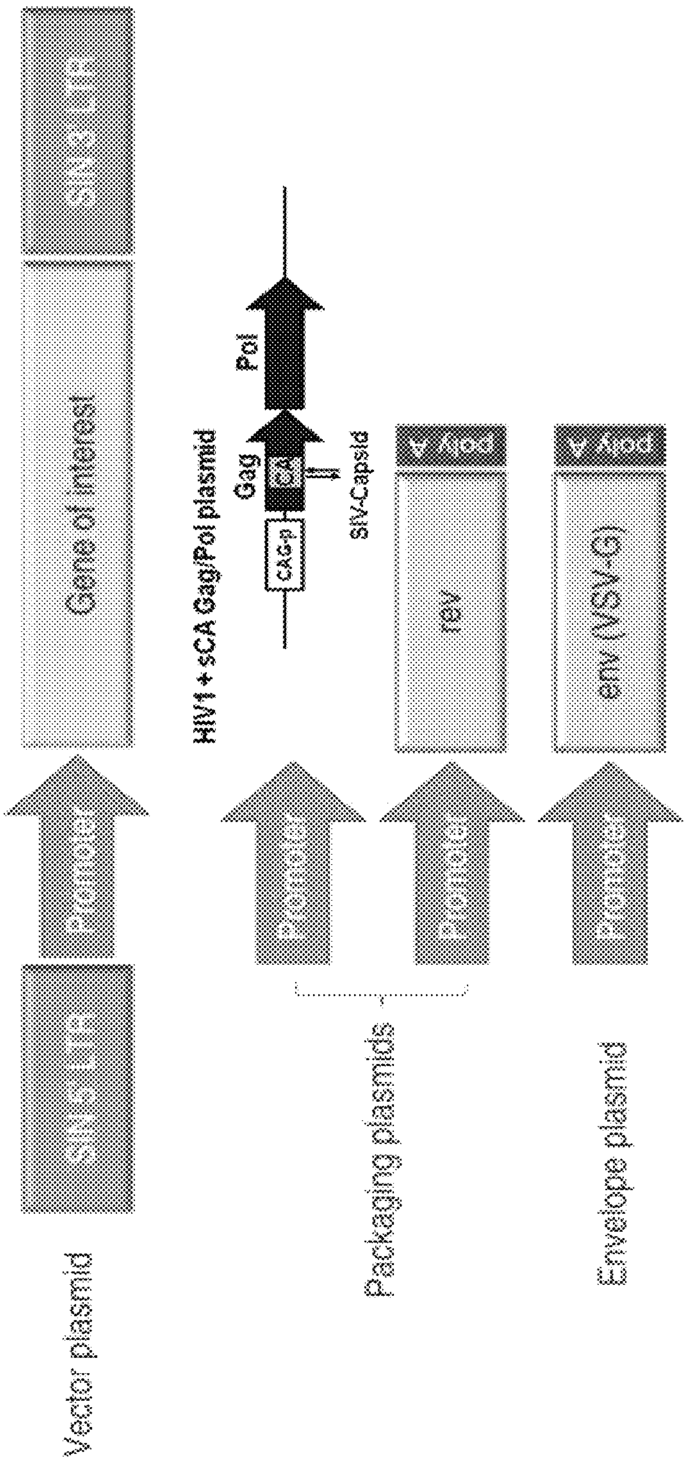

Improved measles virus (MV)-pseudotyped lentiviral vectors and viral vector systems were generated herein by replacing the HIV gag-pol sequence (illustrated in the FIG. 1A) with a sequence encoding xHIV as set forth in SEQ ID NO: 5, which comprises xHIV gag protein, which is a chimeric gag protein from SIV and HIV (FIG. 1B) (Uchida et al. J. Virol, October 2009, p. 9854-9862; Pavlakis, U.S. Pat. No. 8,076,100B2) (FIGS. 1A-1B). The xHIV gag protein encoded by the polynucleotide sequence is protein of SEQ ID NO: 9.

Figure 2A:
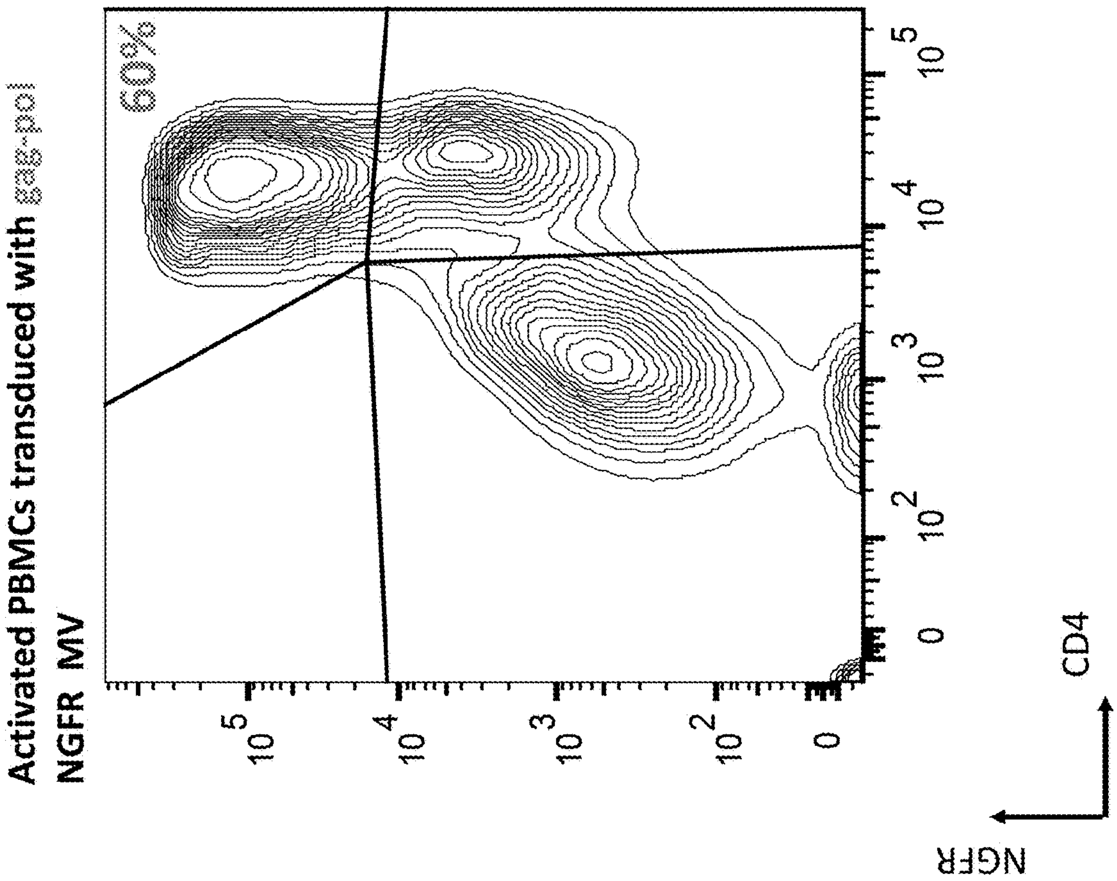
Figure 2B:
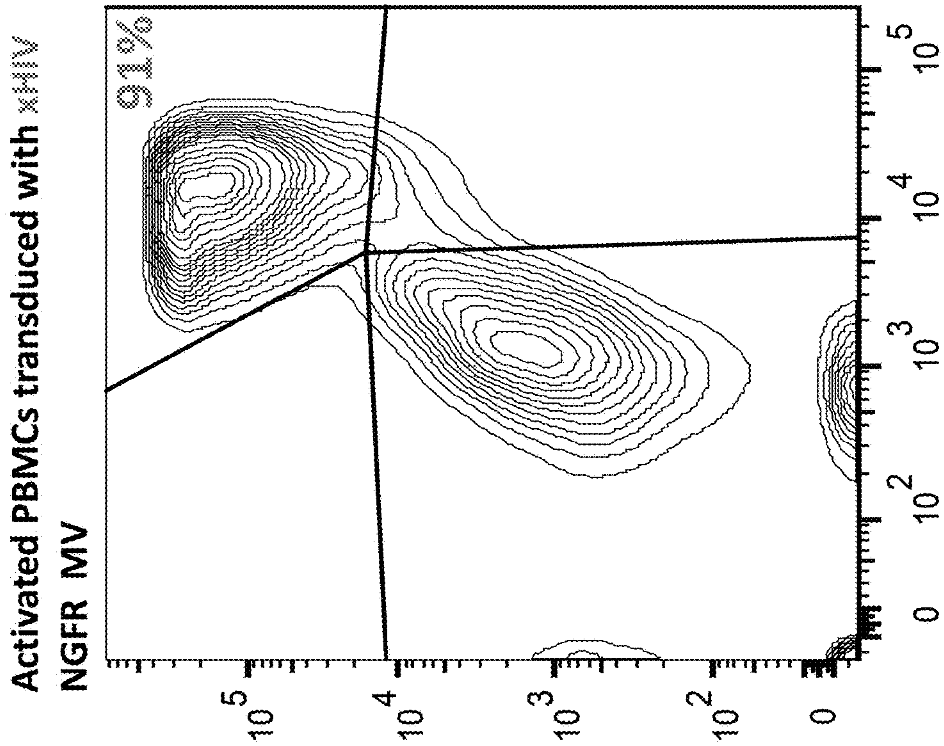

Activated PBMCs were transduced with a pseudotyped viral vector system containing HIV gag-pol and truncated NGFR (gag-pol NGFR MV) (FIG. 2A and FIG. 2C) or a pseudotyped viral vector system containing the chimeric xHIV and truncated NGFR (xHIV NGFR MV) (FIG. 2B and FIG. 2D). Results showed that on day 4, CD4" were transduced at a higher rate when using the pseudotyped viral vector system containing the chimeric xHIV (xHIV NGFR MV) compared to the vector system containing the HIV gag-pol (gag-pol NGFR MV) (FIGS. 2A-2B). Additionally, the xHIV vector displayed higher transduction efficiency (FIGS. 2C and 2D).

Figure 3A:
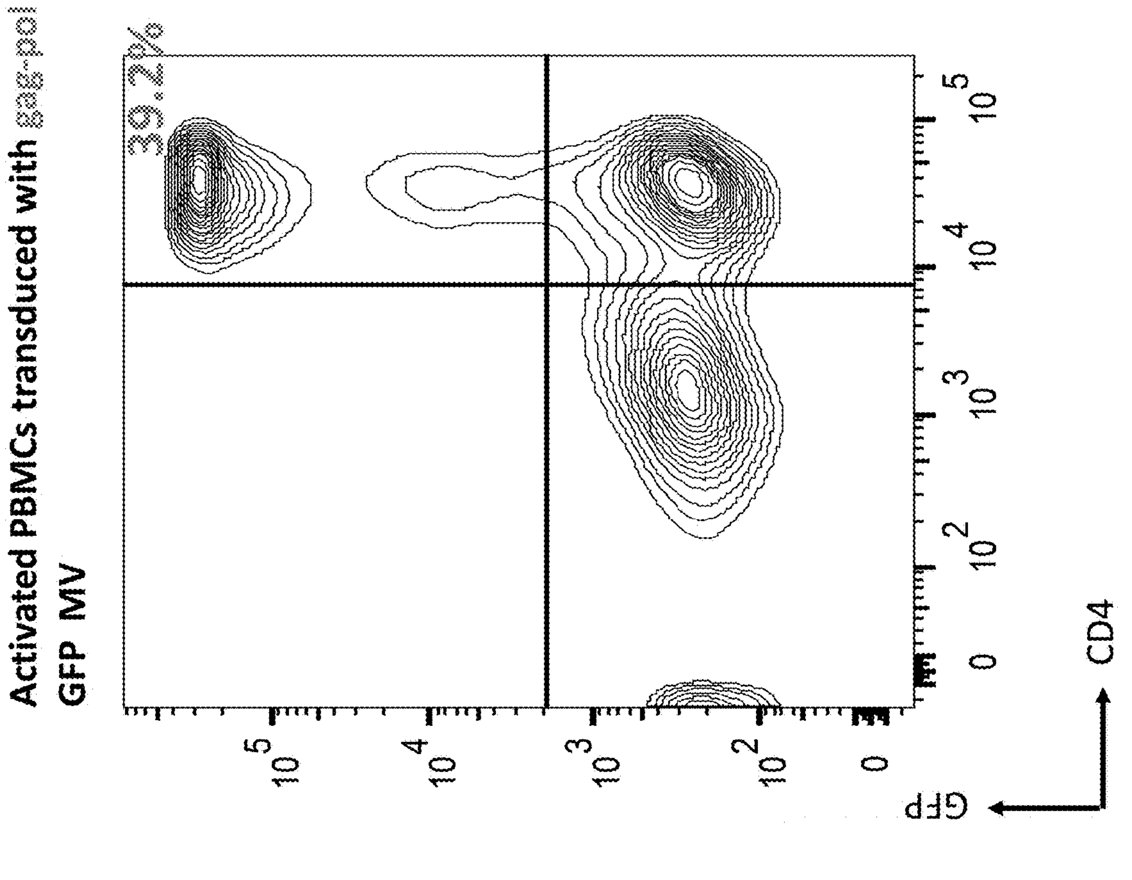
Figure 3B:
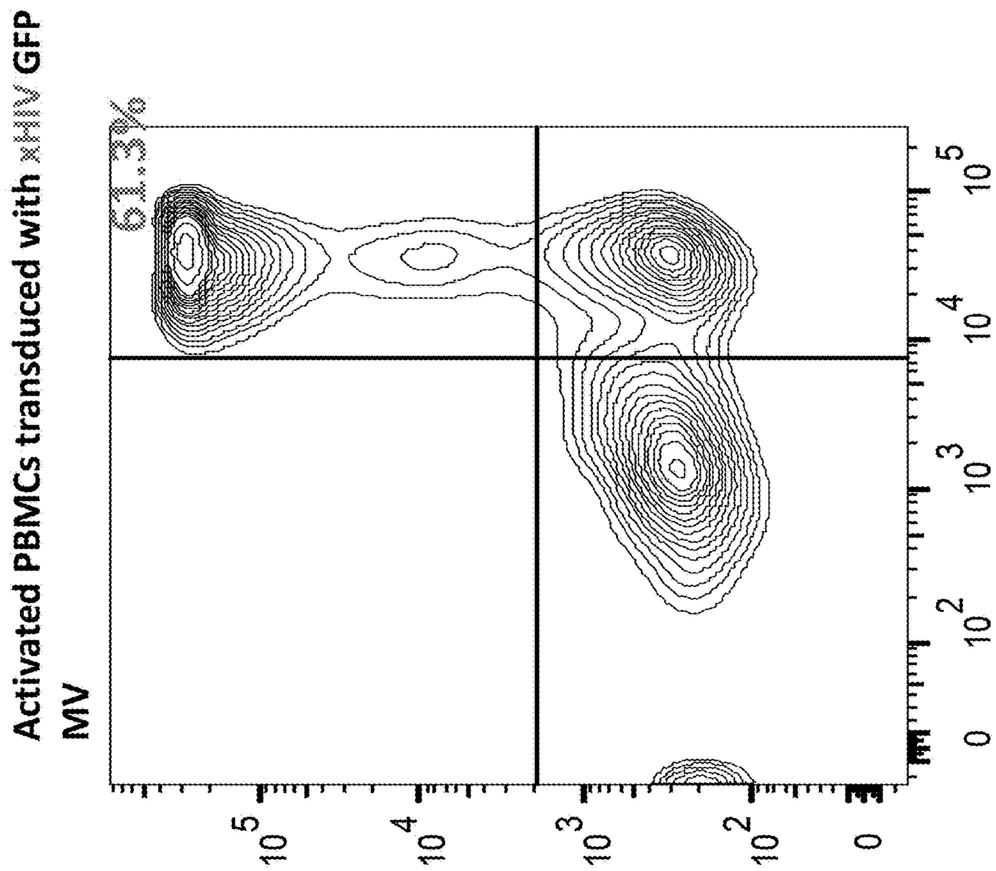

Similar results were obtained from experiments wherein activated PBMCs were transduced with gag-pol GFP MV (FIG. 3A and FIG. 3C) or xHIV GFP MV (FIG. 3B and FIG. 3D). Results from day 4 showed a 3 fold increase in potency with vectors containing chimeric gag (FIGS. 3A-3D).

Figures 4A, 4B:
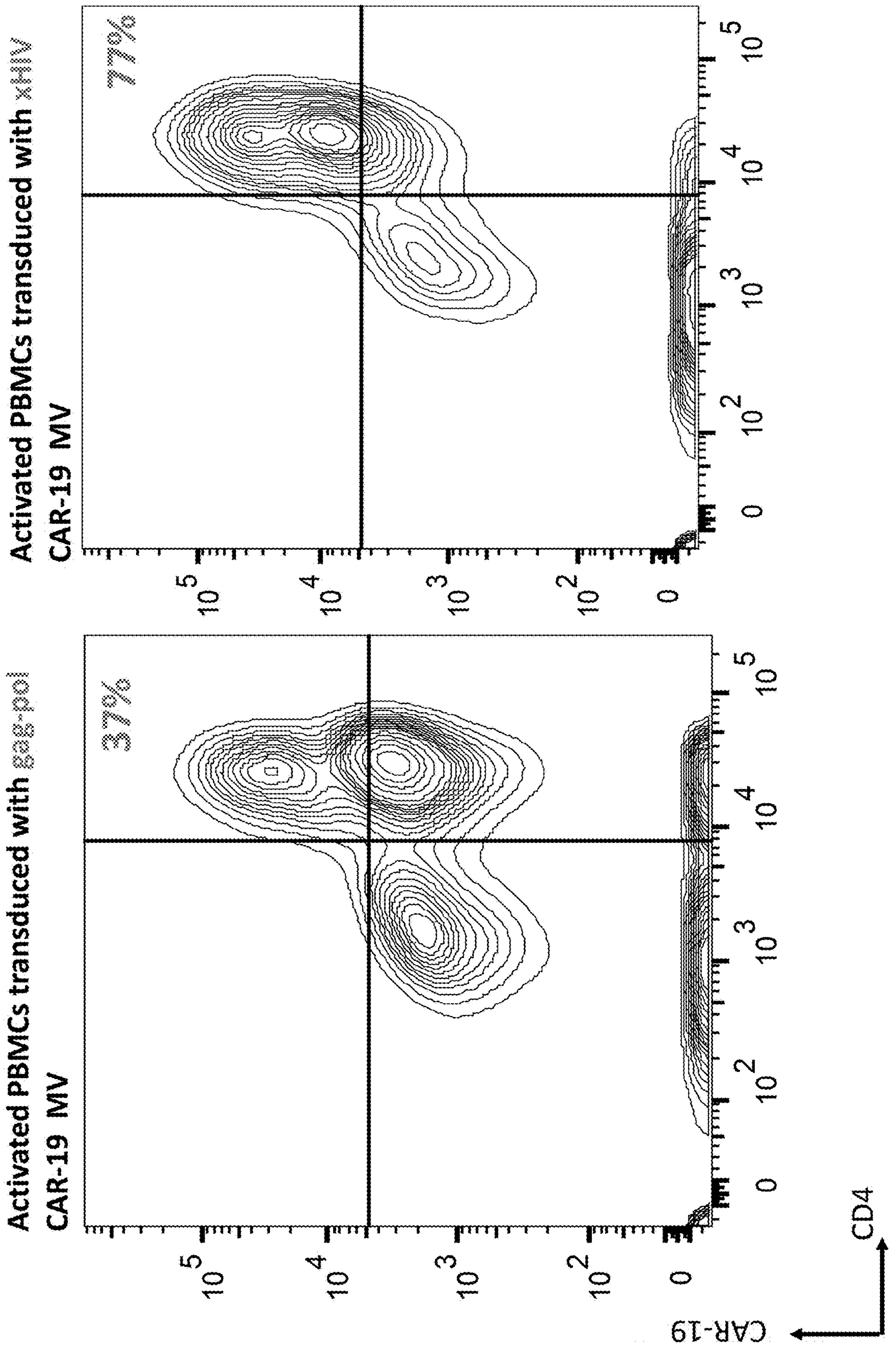
Figure 5B:
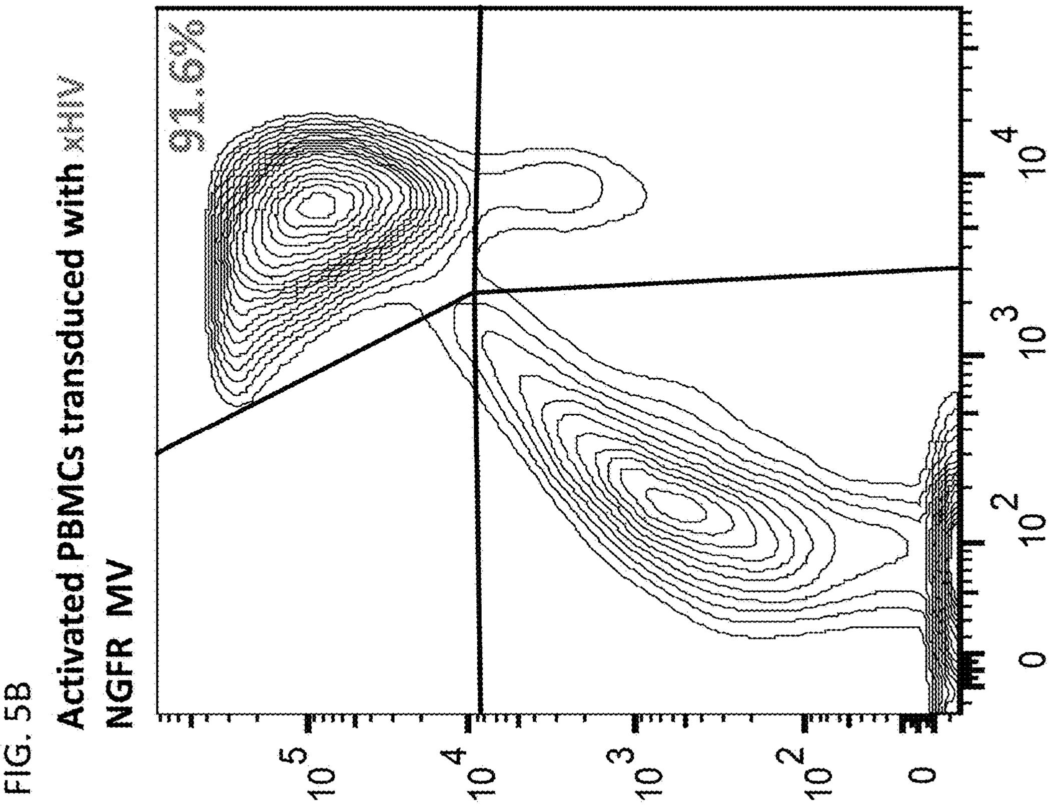
Figure 5A:
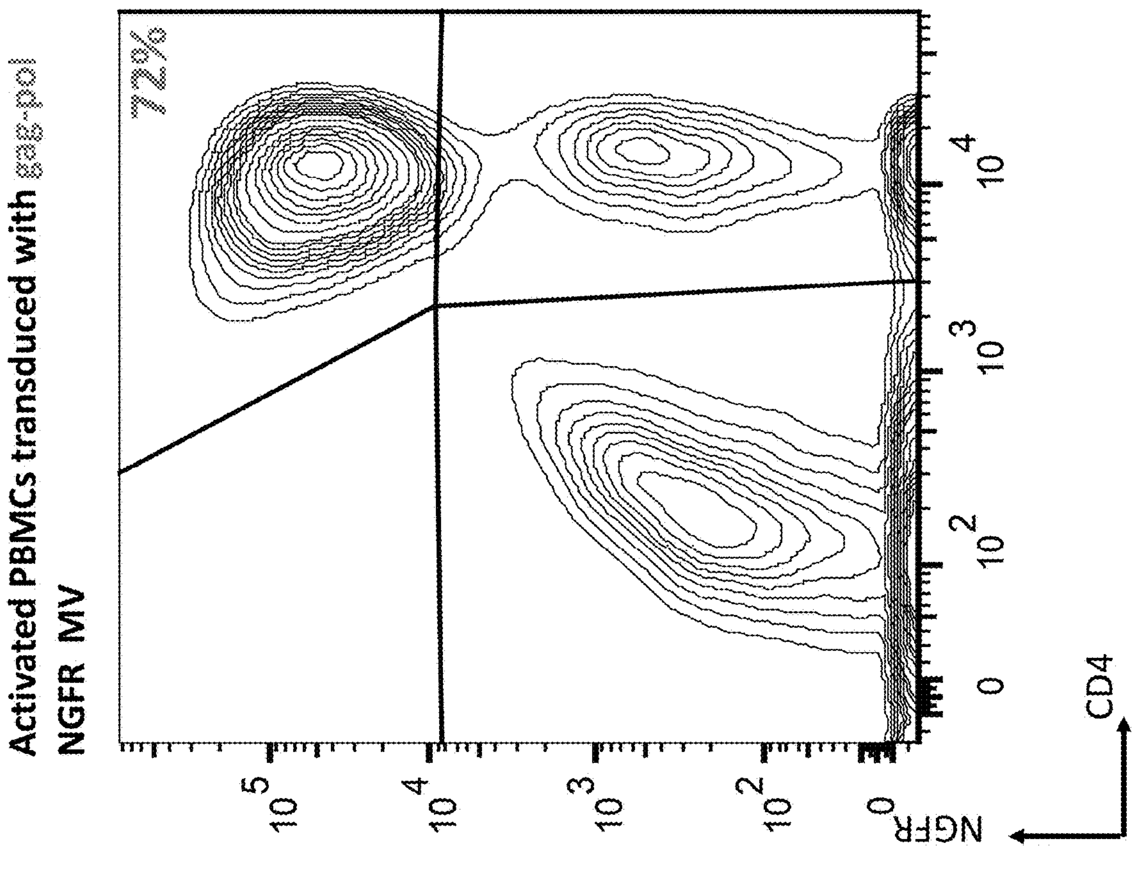
Figure 6A:
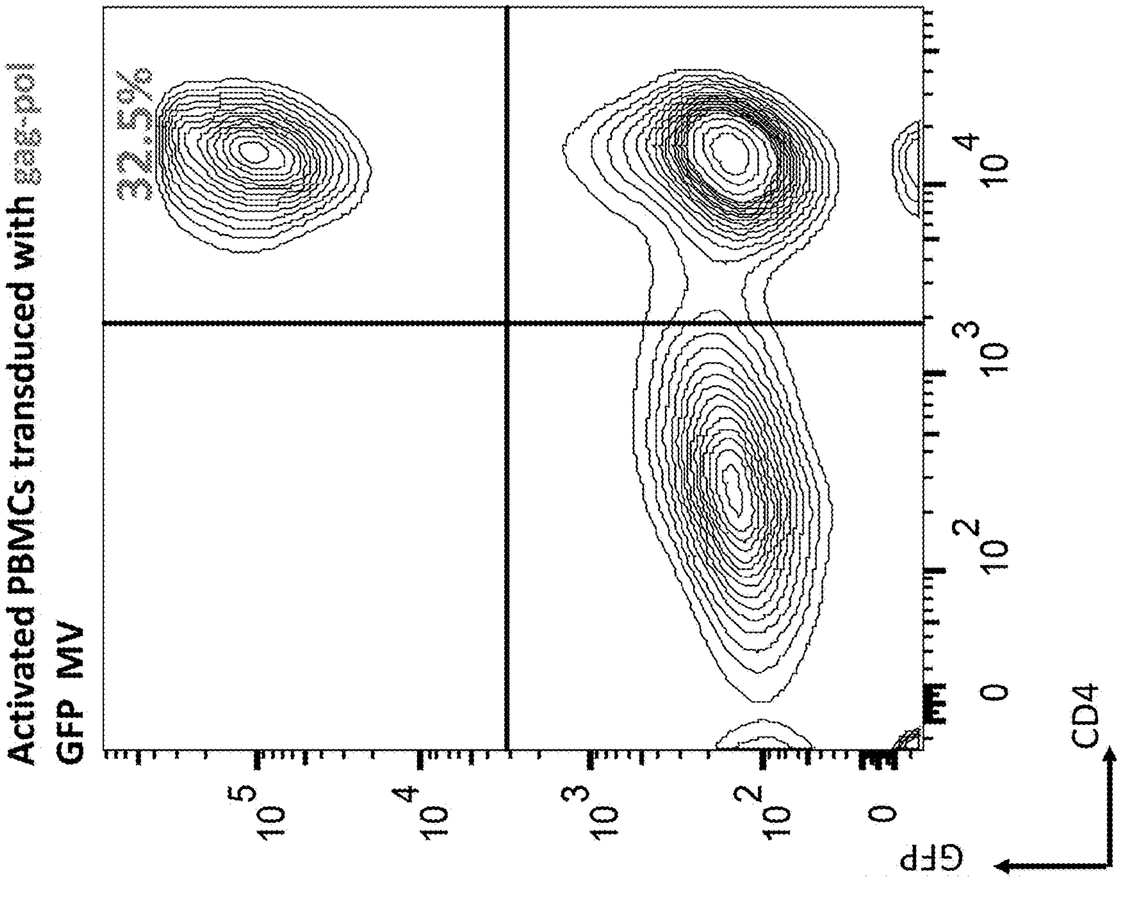
Figure 6B:
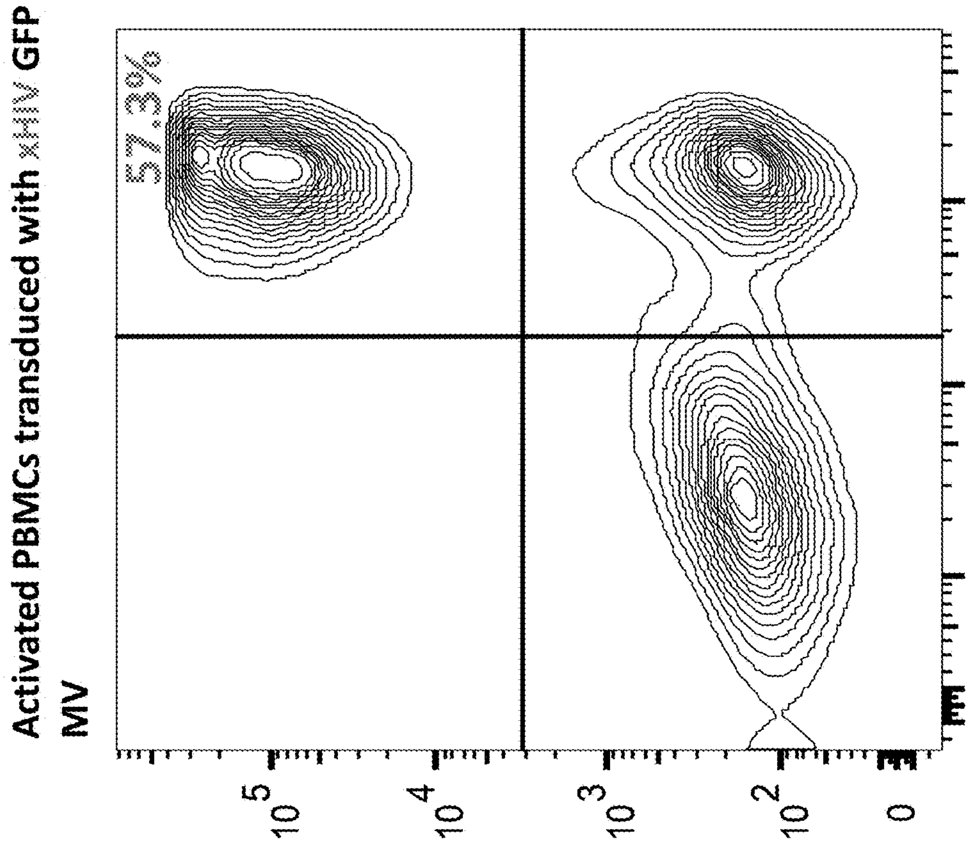

Activated PBMCs were transduced with pseudotyped vectors containing chimeric antigen receptors that target CD19 (CAR-19), packaged using either the HIV gag-pol (gag-pol CAR-19 MV) (FIG. 4A and FIG. 4C) or the chimeric gag (xHIV CAR-19 MV) (FIG. 4B and FIG. 4D). Again, transduction efficiency was increased with the vectors containing the chimeric gag (FIGS. 4A-4B) and 4-5 times less virus was needed (FIGS. 4C-4D).

Figure 7B:
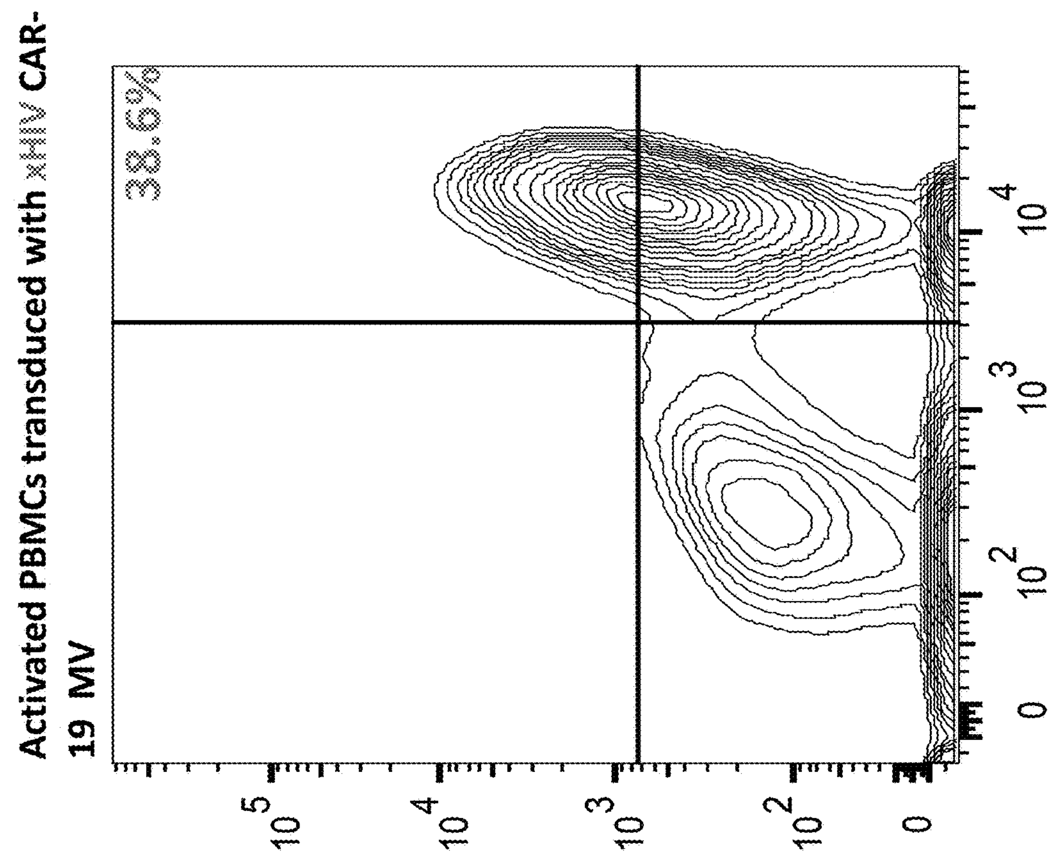
Figure 7A:
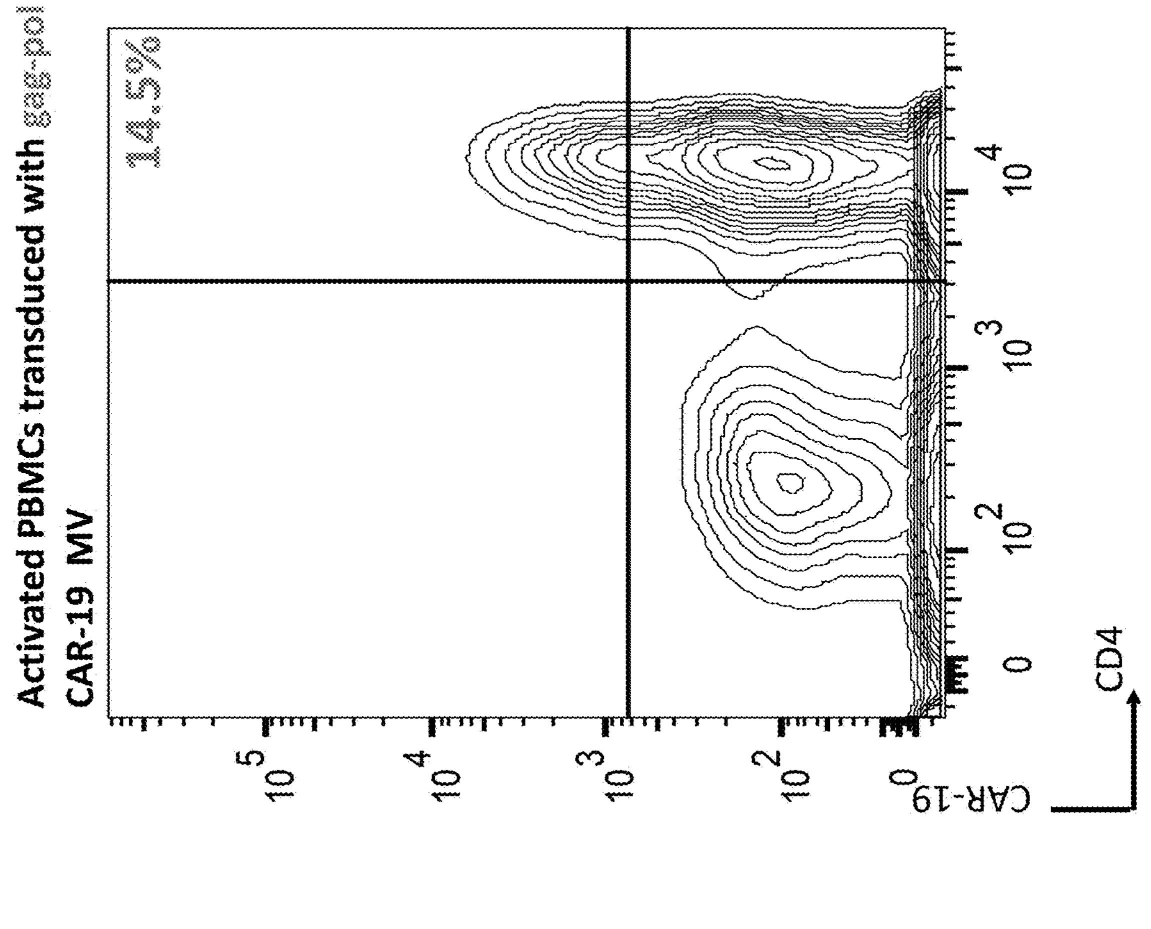

Results from day 12 also demonstrate increased transduction efficiencies in chimeric gag containing vectors (FIGS. 5A-5D, FIGS. 6A-6D, and FIGS. 7A-7D) with higher dilutions displaying larger differences (FIG. 5B, FIG. 5D, FIG. 6B and FIG. 6D). Importantly, an increase in transduction efficiency on day 12 was demonstrated with the pseudotyped vectors containing CAR-19 and chimeric gag (FIGS. 7A-7D), while 10 times less volume was needed (FIG. 7C and FIG. 7D).

Prior to the present invention, the state of the art of gene transfer into T cells for cancer therapy included a variety of ex vivo approaches that range from viral (e.g. lentiviral transduction) to non-viral approaches (e.g. electroporation of transposon plasmids). Since the anti-tumor effect of CAR T cells depends upon their ability to proliferate, stable integration of the transgene is critical. Lentiviruses (LV) commonly used in gene delivery typically (i) lack the pathogenic features of the parental HIV; (ii) lack the ability to generate further infectious particles, and (iii) stably infect a wide variety of cells (by replacing the HIV envelope protein with the G glycoprotein from the vesicular stomatitis virus; VSVG). Susceptibility of cells to infection with VSVG-pseudotyped LV requires expression of the LDL receptor. While activated T cells express the LDL receptor, resting lymphocytes do not and are therefore resistant to transduction with standard VSVG-pseudotyped LV vectors. Thus, to date, genetic modification of T cells has been carried out ex vivo because (i) only the cells of interest are exposed to the virus thus increasing safety and reducing the amount of viral particles needed, and (ii) T cells can be activated ex vivo using anti-CD3/CD28 beads or similar techniques in order to enhance expression of the LDL receptor and improve transduction.

Among the major challenges facing patients and physicians is the duration of the ex vivo manufacturing process, which is at least 17 days and often much longer. Additional logistical issues that limit access, increase time-to-treatment, and generate costs include apheresis availability, GMP suite availability in time for manufacturing, and release testing of each product which is thus treated as a new lot.

As disclosed herein, all these issues could be circumvented by in vivo transduction of T cells after systemic administration in the patient using a specific, efficient viral system. It is contemplated that such a viral system has the following features: (i) viral particles are able to specifically transduce the target cells of interest, (ii) transduction efficiency is high enough to lead to a sufficient number of T cells carrying the transgene after in vivo administration, and (iii) the transduced cells are functional.

To facilitate in vivo gene transfer, viral particles are engineered to bind a cell surface marker of choice for cell entry, rather than their natural receptors. The viral particles express a targeting ligand such as a single-chain variable fragment (scFv) in order to accomplish specific binding to the surface of the target cell. For example, LV is pseudotyped with measles virus hemagglutinin (HA) and fusion (F) proteins that were mutated to prevent binding to their natural receptors CD46 and SLAM. In order to then confer specificity on the MV-pseudotyped LV, the HA gene is modified to express a targeting domain, such as a scFV against CD8 or CD4. In addition, the sequence encoding the HIV gag protein in the pseudotyped lentiviral vector was replaced with a chimeric SIV Gag protein, xHIV. The incorporation of the chimeric gag into the pseudotyped lentiviral vector unexpectedly resulted in enhancing the transduction efficiency without loss of specificity.

Example 2

Erythropoietin Receptor (EpoR)-Based Binding and Signaling Components

A schematic illustrating another embodiment of a signaling complex of the present disclosure is shown in FIGS.

Figure 8B:
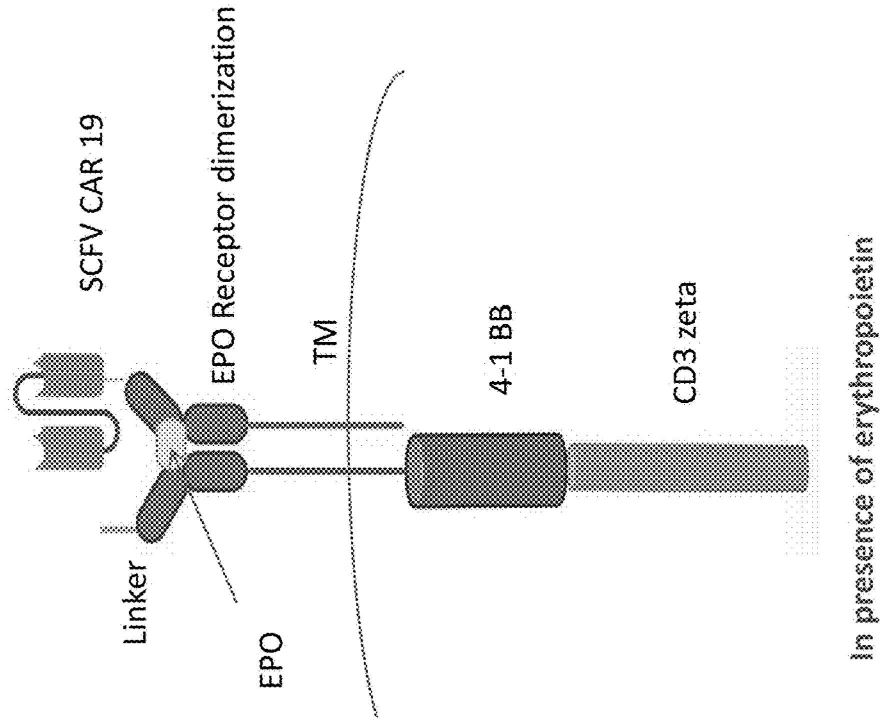
FIGS. 8A-8B is a schematic illustrating a split vector application in accordance with some embodiments of the present disclosure. (A) As described in Example 2, EpoR signaling (e.g., EpoR 4-1BB-CD3 zeta (BBz) endodomain encoded by transgene 1 from lentiviral vector 1 (LV 1)) and EpoR binding (e.g., the CAR-EpoR exodomain encoded by transgene 2 from lentiviral vector 2 (LV 2)) components are individually expressed in a cell using different lentiviral vectors for each. (B) Dimerization domains of EpoR dimerize to provide signaling activity in the presence of the dimerizing agent EPO.
Figure 8A:
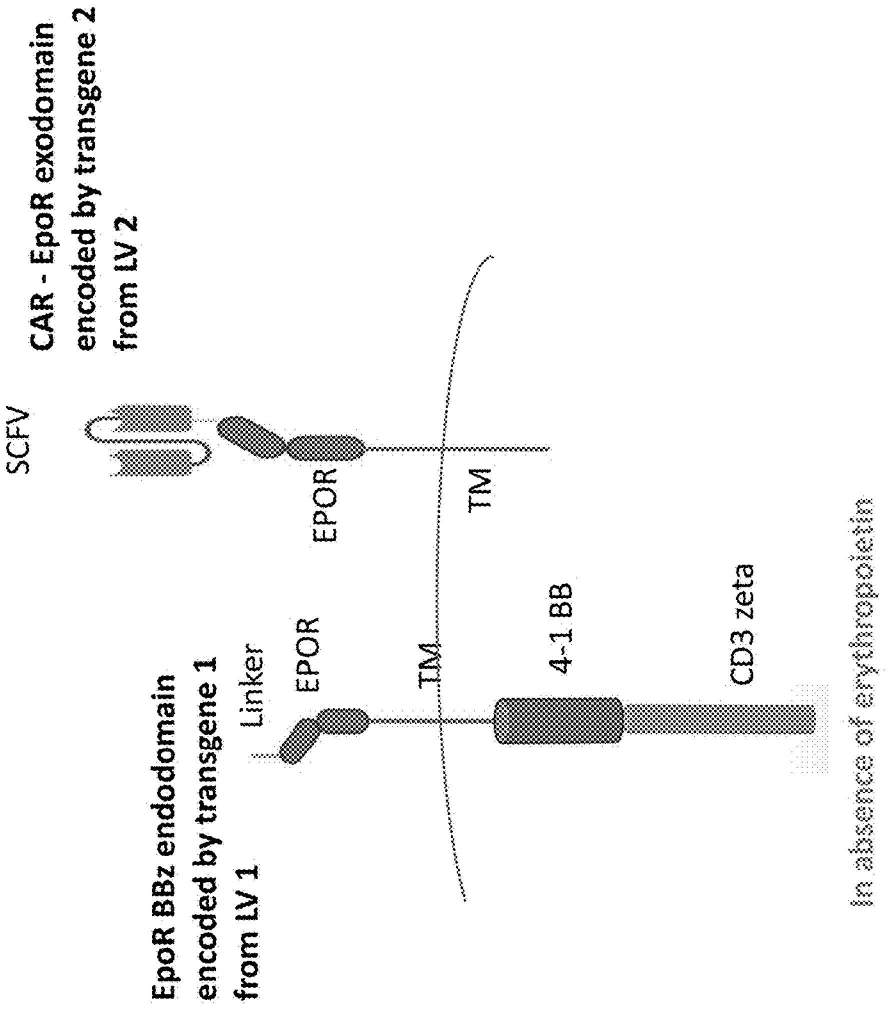
Figure 9:
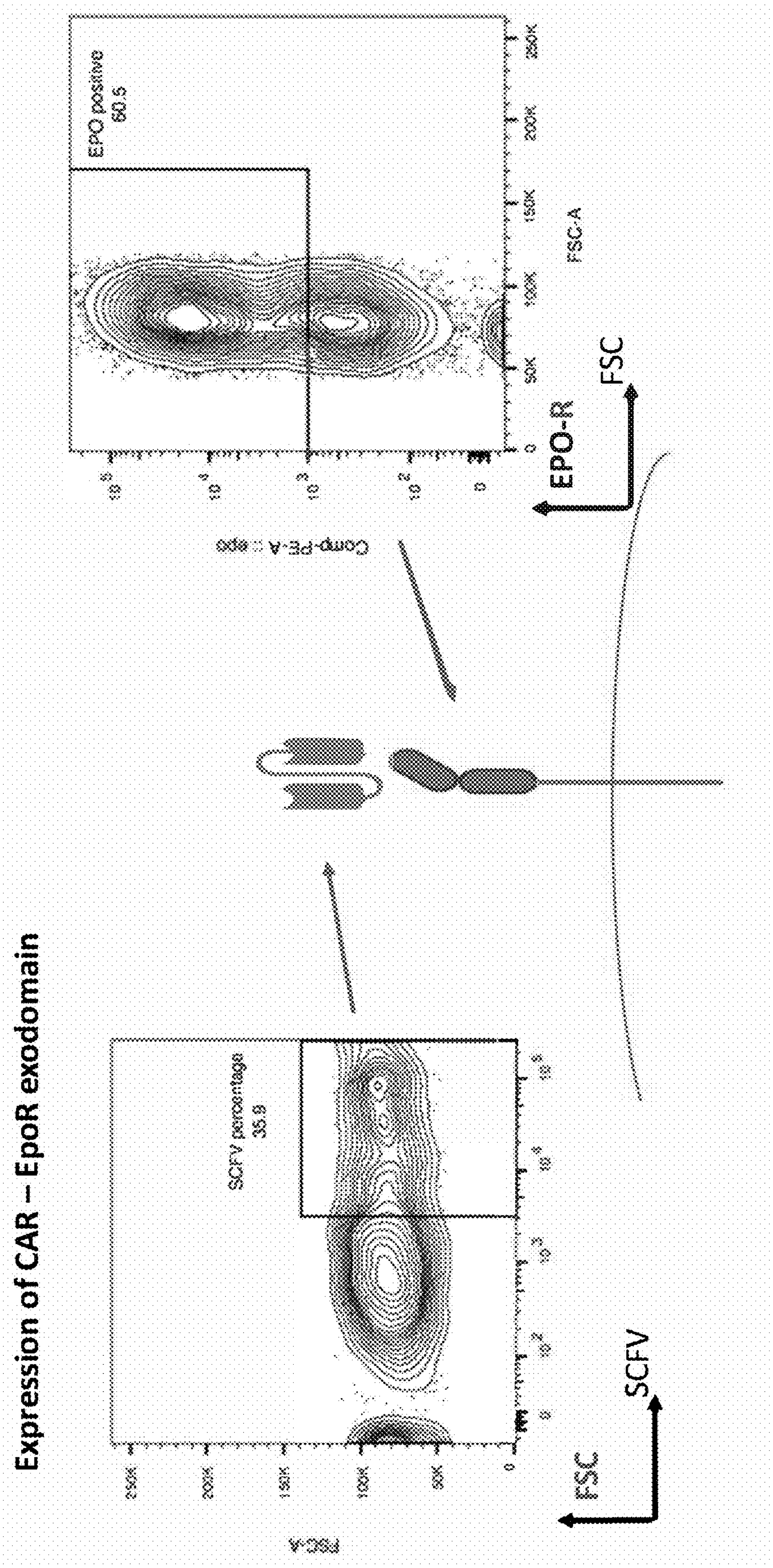
FIG. 9 depicts results from experiments of expression of CAR-EpoR exodomain described in Example 2.
Figure 10:
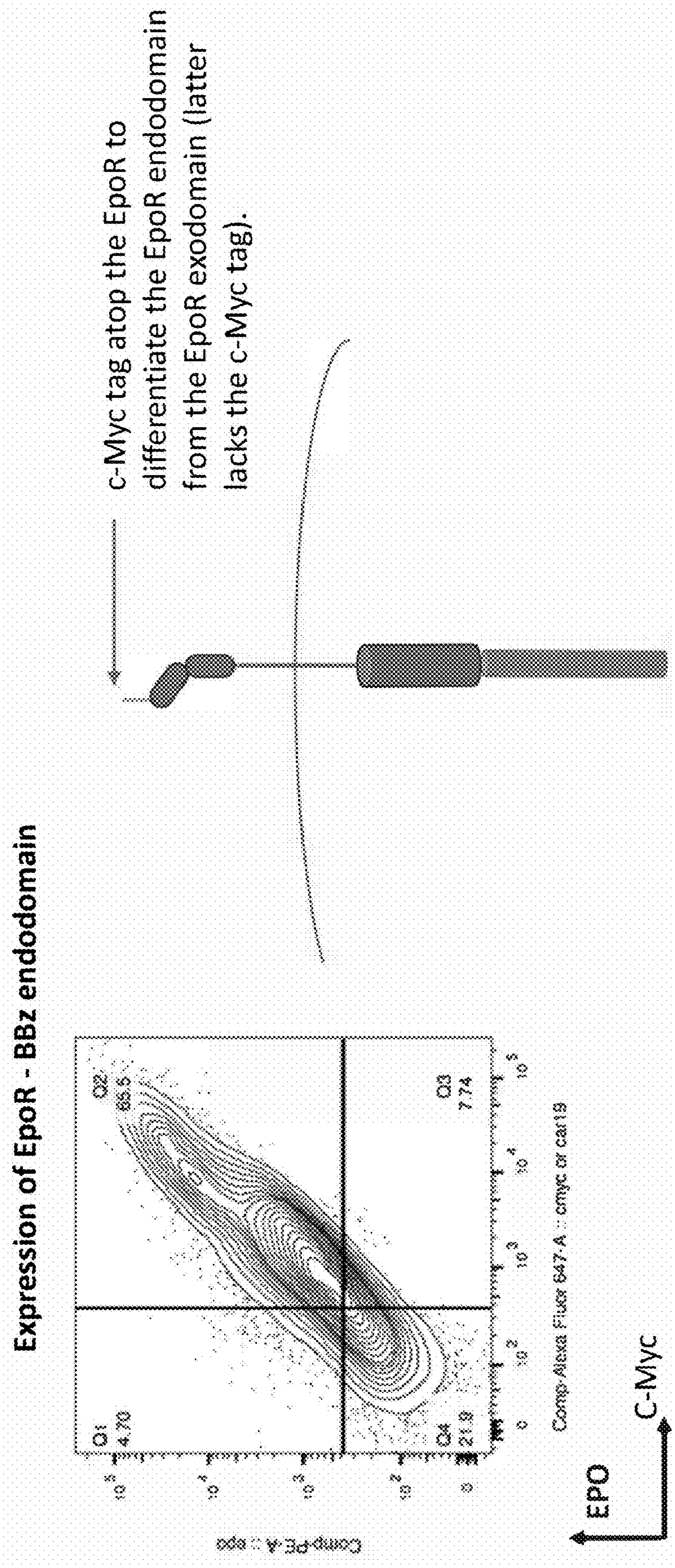
FIG. 10 depicts results from experiments of expression of EpoR BBz endodomain described in Example 2.

8A-8B wherein the EpoR signaling (e.g., EpoR 4-1BB-CD3 zeta (BBz) endodomain encoded by transgene 1 from lentiviral vector 1 (LV 1)) and EpoR binding (e.g., the CAR-EpoR exodomain encoded by transgene 2 from lentiviral vector 2 (LV 2)) components are individually expressed in a cell (e.g., T cell) using different lentiviral vectors for each (FIG. 8A). This exemplified EPOR-based system separates the antigen recognition (e.g., scFV CAR 19) and signaling functions of a CAR into two distinct polypeptides that contain the dimerization domains of EpoR that dimerize to provide signaling activity in the presence of the dimerizating agent EPO (FIG. 8B). The expression of CAR-EpoR exodomain is shown in FIG. 9 and the expression of EpoR BBz endodomain is shown in FIG. 10.

Figure 11:
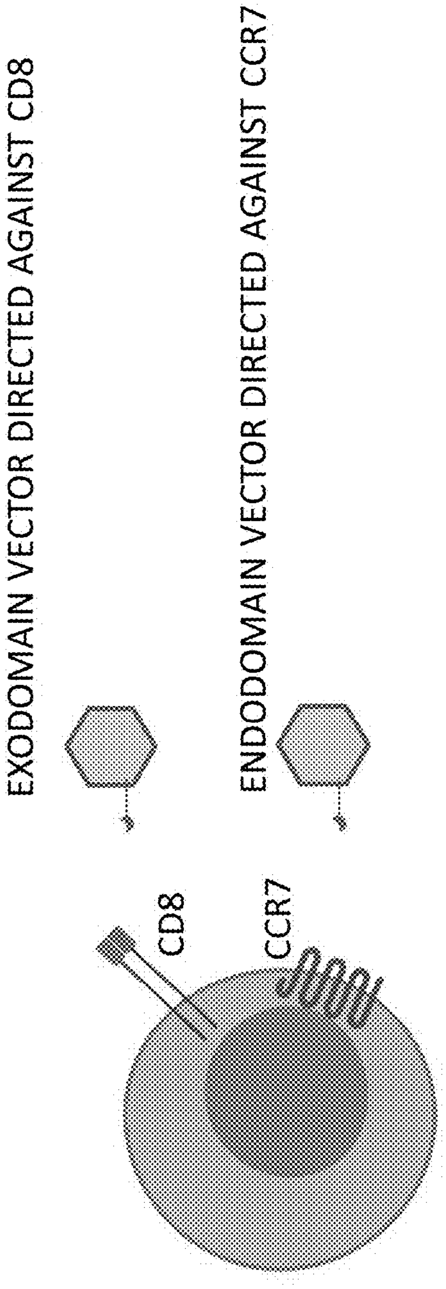
FIG. 11 is a schematic illustrating another embodiment of the split vector application where only CD8+CCR7+ cells contain both the exo- and endo-domains, which can be activated via the CAR and with administration of EPO as described in Example 2.

Such a split vector application can be tailored such that the exodomain vector has a first targeting moiety that binds to a first target (e.g., CD8) on a cell, whereas the endodomain vector has a second targeting moiety that binds to a second target (e.g., CCR7) on the cell, or vice versa. In the schematic of such a concept illustrated in FIG. 11, only CD8+CCR7+ cells can contain both the exo- and endodomains, which can be activated via the CAR and with administration of EPO.

Example 3

Figure 12:
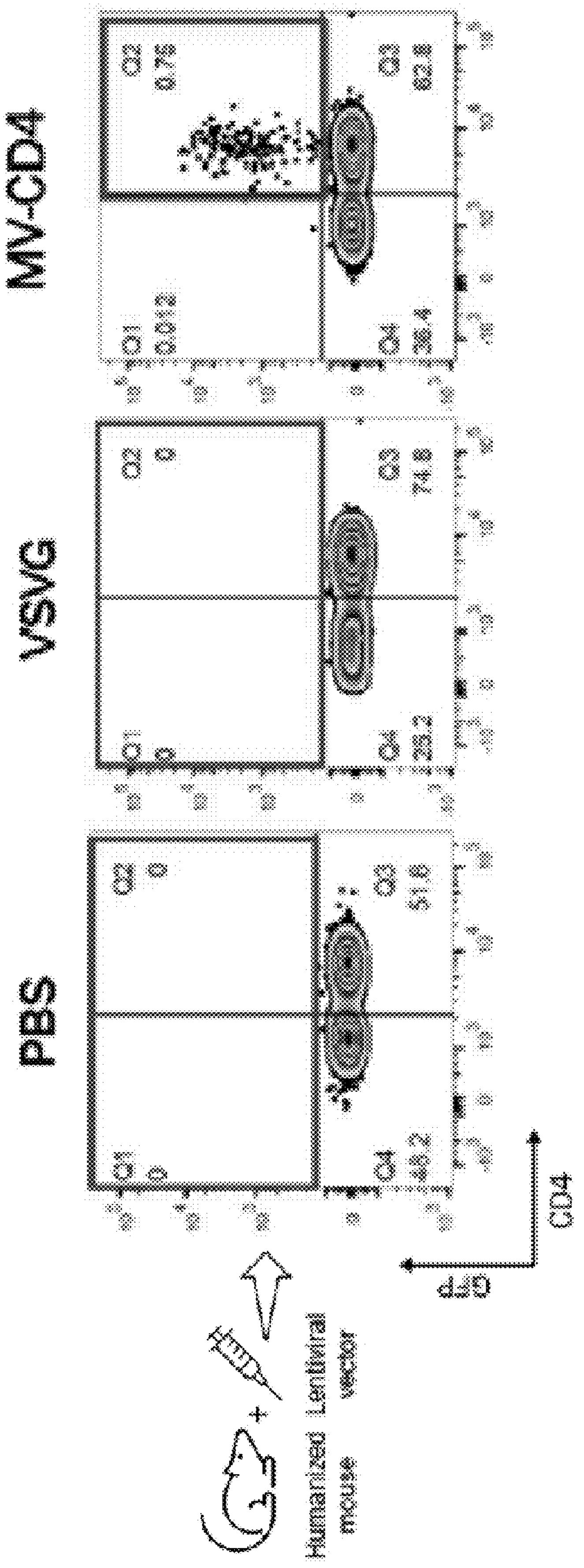
FIG. 12 depicts results from experiments of specific transduction of human CD4 cells in blood of humanized mice with CD4-targeting MV system, GFP reporter, 7 days after IV administration of vector.

Specific Transduction of Human CD4 Cells in Blood or Liver of Humanized Mice Humanized mice were injected with a measles virus (MV-CD4) lentiviral vector targeting CD4 cells and comprising a GFP reporter, a vesicular stomatitis virus G-protein (VSVG) lentiviral vector, or PBS. At 7 days after IV administration, blood was extracted and subjected to analysis using flow cytometry. The data, as provided in FIG. 12, showed specific transduction of human CD4 cells in blood of humanized mice with the MC-CD4 vector.

Figure 13:
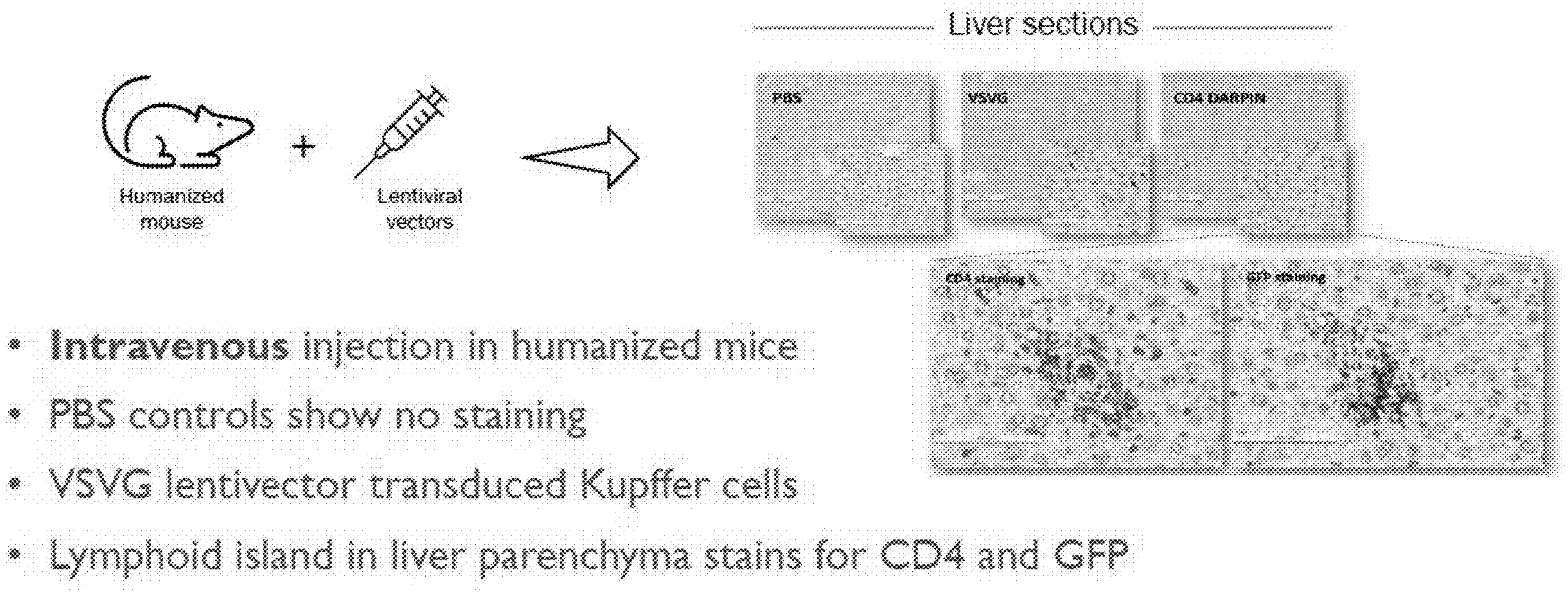
FIG. 13 depicts results from experiments of specific transduction of human CD4 cells in liver of humanized mice with CD4-targeting MV system, GFP reporter, 7 days after IV administration of vector. VSVG control shows non-specific transduction of liver Kupffer cells.

In the same experiment, livers were extracted 7 days following IV administration of MV-CD4, VSVG, or PBS, sectioned and subjected to immunohistochemical staining. The data, as provided in FIG. 13, showed no positive staining against CD4 and GFP in animals injected with PBS, staining of Kupffer cells in animals injected with VSVG lentiviral vector, and staining of the lymphoid island in liver perenchyma of animals injected with MV-CD4. Kupffer cells are the resident macrophages of the liver and primary target of VSVG pseudotyped lentiviral vectors. Positive staining of a lymphoid follicle in liver parenchyma of animals injected with MV-CD4 shows specific transduction of human CD4 cells in liver of humanized mice.

Example 4

Specific Transduction of Human CD4 Cells in Peritoneum of Humanized Mice

Figure 14:
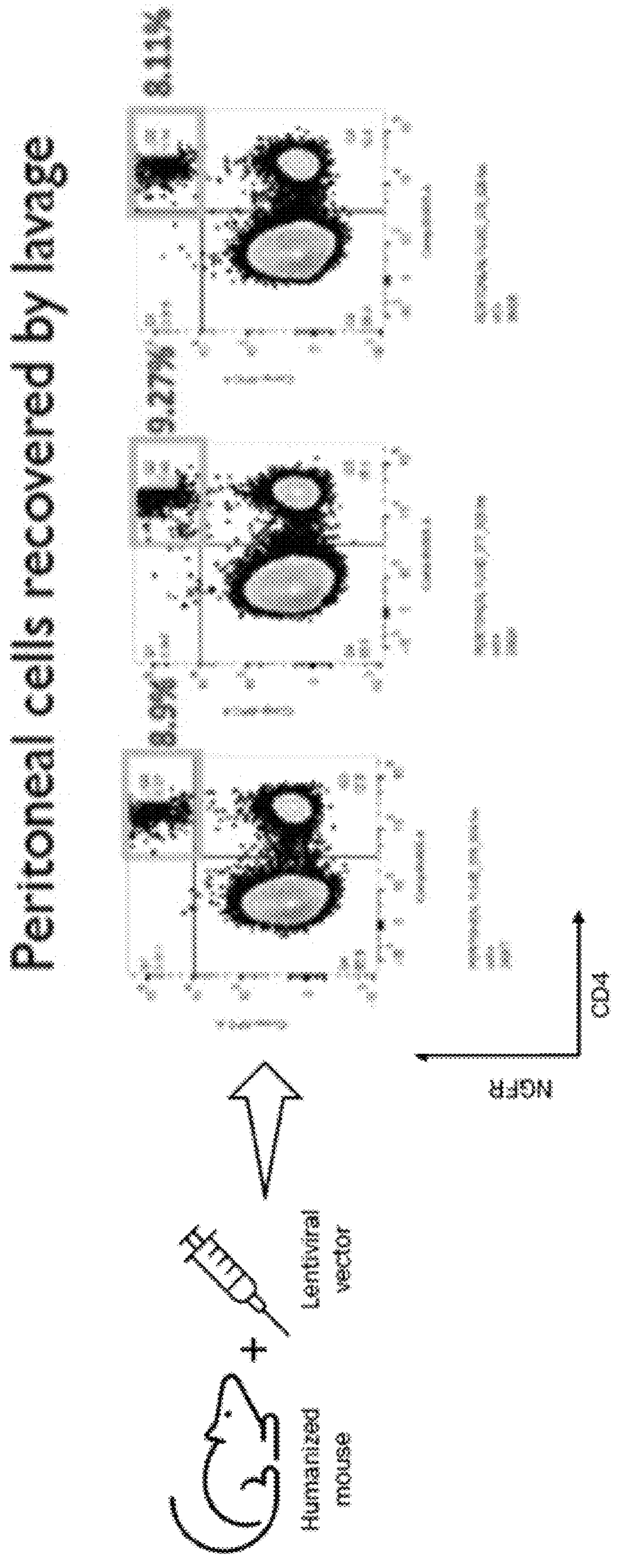
FIG. 14 depicts results from experiments of specific transduction of human CD4 cells in peritoneum of humanized mice with CD4-targeting MV system, NGFR reporter, 7 days after IV administration of vector. Triplicate mice are shown.

Humanized mice were injected with MV-CD4 lentiviral vector comprising a NGFR reporter, a VSVG lentiviral vector, or PBS. Peritoneal cells were recovered by lavage 7 days following IV administration of MV-CD4, VSVG, or PBS, and subjected to flow cytometry. The data, as provided in FIG. 14, showed expression of NGFR in human cells from the peritoneal cavity. Accordingly, CD4+ T cells of humanized mice show specific transduction with MV-CD4.

Example 5

Figure 15:
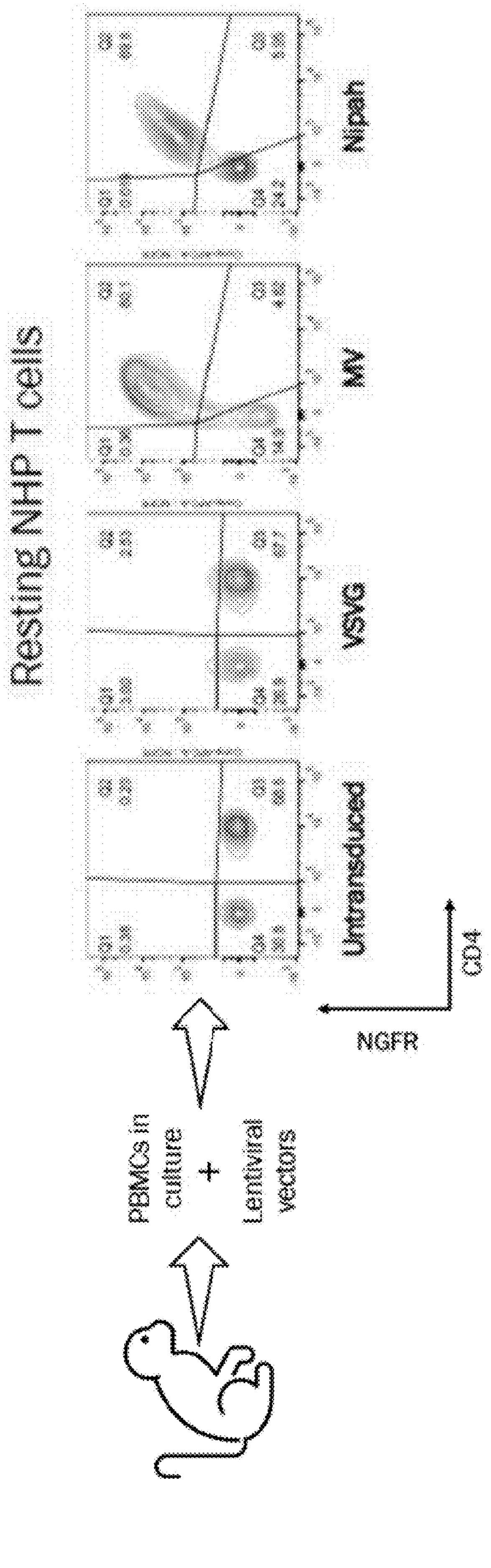
FIG. 15 depicts results from experiments of specific transduction of resting (non-activated) rhesus macaque CD4 cells in vitro. NGFR reporter. VSVG control shows no transduction since the cells are not activated. MV and NV systems show equivalently high and specific transduction.

Specific Transduction of Resting (Non-Activated) Rhesus Macaque CD4 Cells In Vitro PBMCs of rhesus macaque were transduced with a MV lentiviral comprising a NGFR reporter, a Nipah lentiviral vector (NV), a VSVG lentiviral vector, or PBS. Four days after transduction, resting NHP T cells were subjected to flow cytometry. The data, as provided in FIG. 15, showed expression of NGFR and CD4 in cells transduced with MV or NV, but not VSVG or in untransduced cells. Accordingly, resting NHP T cells transduced with MV or NV express CD4.

Example 6

Figure 16:
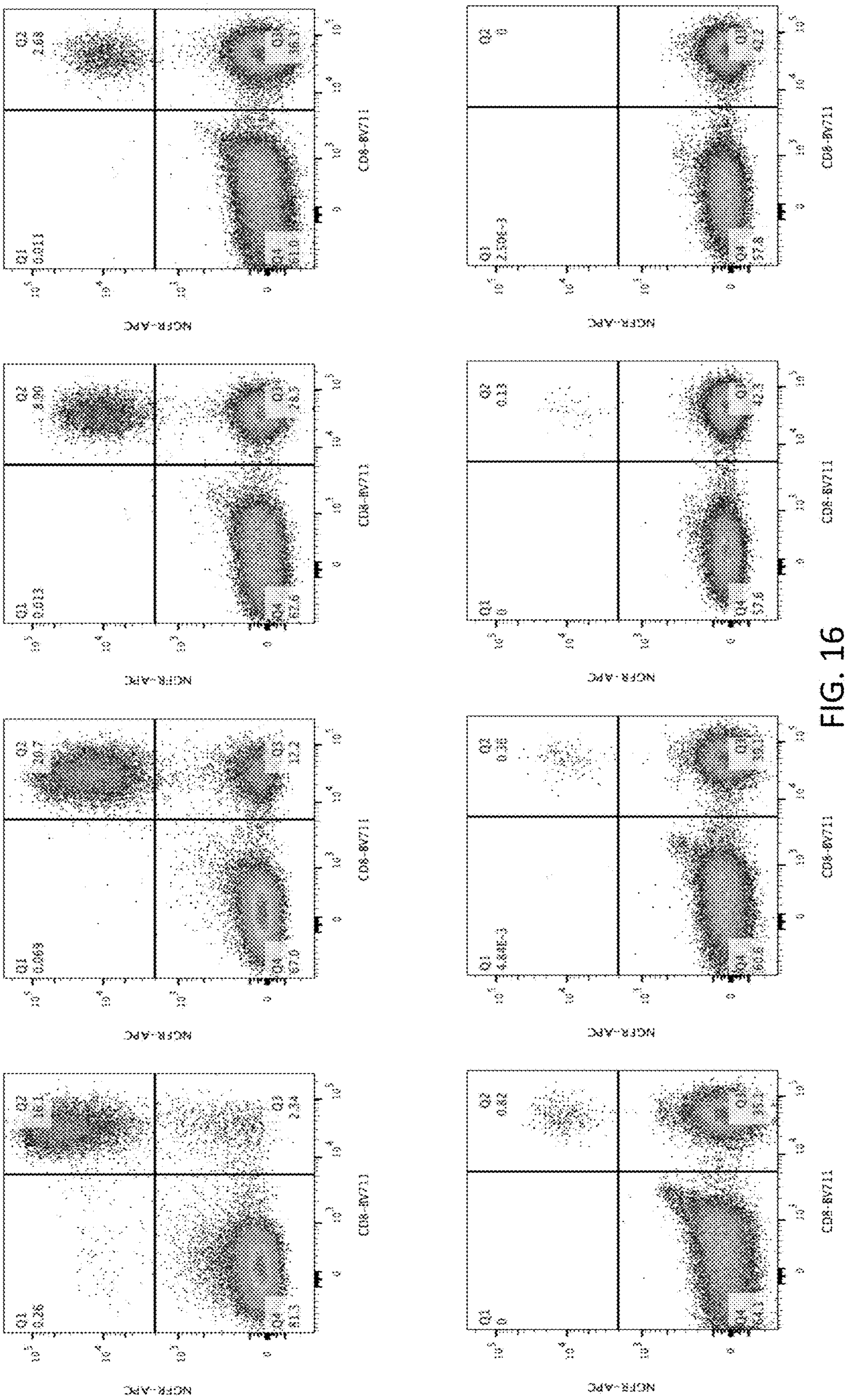
FIG. 16 depicts results from experiments of human T cells stimulated, transduced with MV-pseudotyped, anti-CD8 DARPIN redirected vector made using xHIV gag and activated with IL7 and IL15. Flow cytometry on day 11 shows efficient and specific transgene expression. Individual FACS plots show expression at 3-fold dilutions of viral vector.
Figure 17:
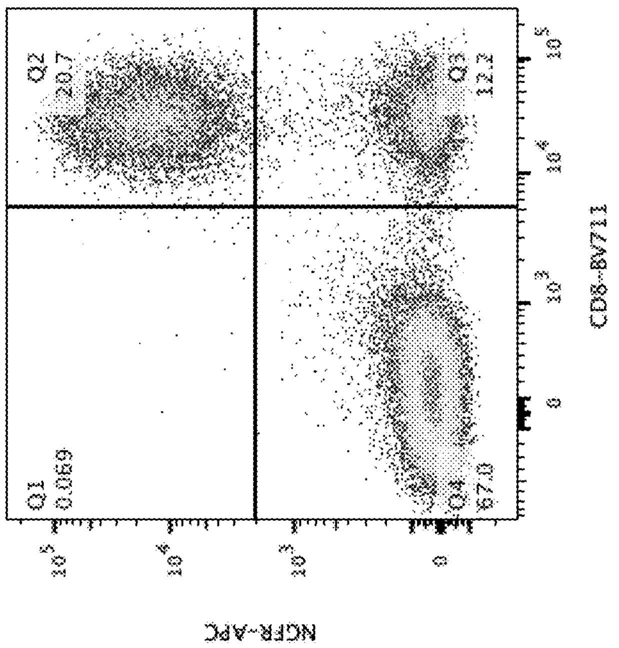
FIG. 17 depicts results from experiments of human T cells stimulated, transduced with MV-pseudotyped, anti-CD8 DARPIN redirected vector made using xHIV gag and activated with IL7 and IL15. Flow cytometry on day 11 shows efficient and specific transgene expression. Exemplary FACS plot from slide 1 is shown as representation. Transduction efficiency is 20.7/20.7+12.2=63%.

Stimulated Human T Cells Transduced with the MV Anti-CD8 DARPIN Vector Show Efficient and Specific Transgene Expression Human T cells were stimulated using anti-CD3/CD28 beads, transduced with MV pseudotyped anti-CD8 DARPIN redirected vector made using xHIV gag and activated with IL7 and IL15. Cells were subjected to flow cytometry on day 11. The data, as provided in FIG. 16 show the expected profile of protein expression at 3-fold dilutions of viral vector, with an exemplary plot shown in FIG. 17. Accordingly, stimulated human T cells transduced with the MV anti-CD8 DARPIN vector show efficient and specific transgene expression.

Example 7

Figure 18:
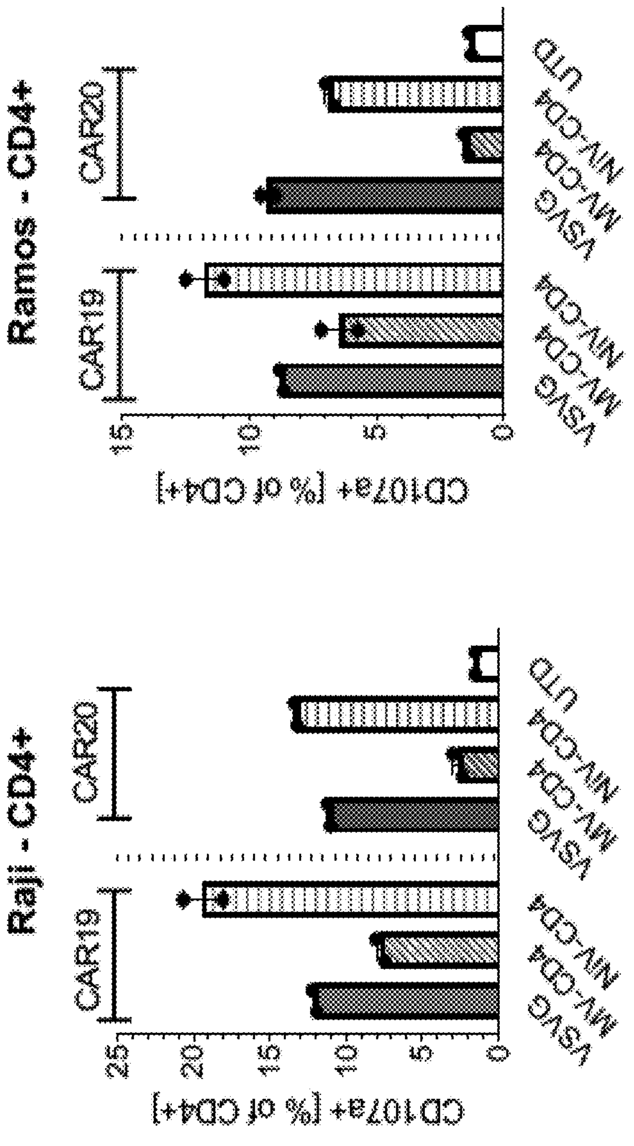
FIG. 18 depicts results from experiments of degranulation in response to two different CD19+CD20+ lymphoma cell lines with anti-CD20 or anti-CD19 BBz CAR20 (VSVG) or antiCD20 or anti-CD19 KIR MV or NiV systems.

Anti-CD19 CAR MV-CD4, Anti-CD19 CAR NiV-CD4, and Anti-CD20 CAR NiV-CD4 Vectors are Functional Degranulation was assessed in Raji or Ramos CD19+ CD20+ lymphoma cell lines in response to anti-CD20 or anti-CD19 BBz CAR20 (VSVG), or anti-CD20 or anti-CD19 KIR MV or NV systems. Degranulation was measured using flow cytometry by calculating the percentage of CD107a+ cells within the population of CD4+ cells. The data, as provided in FIG. 18, showed specific degranulation of T cells transduced with VSVG, anti-CD19 CAR MV-CD4, anti-CD19 CAR NiV-CD4, or anti-CD20 CAR NiV-CD4, but not anti-CD20-MV-CD4 upon exposure to both cell lines. Accordingly, anti-CD19 CAR MV-CD4, anti-CD19 CAR NiV-CD4, and anti-CD20 CAR NiV-CD4 vectors increase degranulation of CD4+ cells.

Example 8

AntiCD20 KIR CAR MV are Functional, Albeit with Slower Kinetics than Anti-CD20 BBz CAR20 (VSVG)

Figure 19:
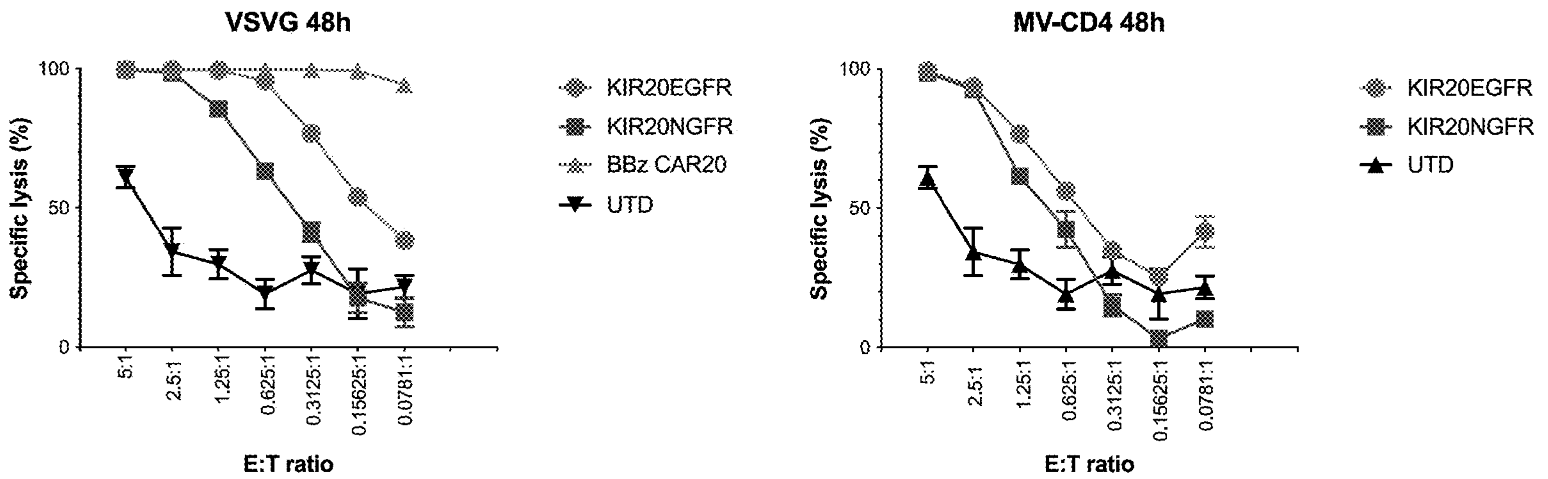
FIG. 19 depicts results from experiments of killing of CD20+ lymphoma cell line with anti-CD20 BBz CAR20 (VSVG) or antiCD20 KIR MV. KIR20 system is slower to respond (kill) than standard BBz-costimulated CAR system.

T cells transduced with KIRCAR20, at efficiency of 17%, were incubated with luciferase-expressing Z138 lymphoma cells at 5:1, 2.5:1, 1.25:1, 0.625:1, 0.3125:1, 0.15625:1, or 0.0781:1 E:T ratios. Cytotoxicity was evaluated at 48 hours following transduction and defined as reduction in luciferase activity, and is shown in FIG. 19. T cells transduced with the KIRCAR20 system required higher E:T ratios to induce specific lysis than the standard BBz-costimulated CAR system. Therefore, T cells transduced with the KIRCAR20 system are functional but induce less prompt killing than the standard BBz CAR system.

Example 9

Figure 20:
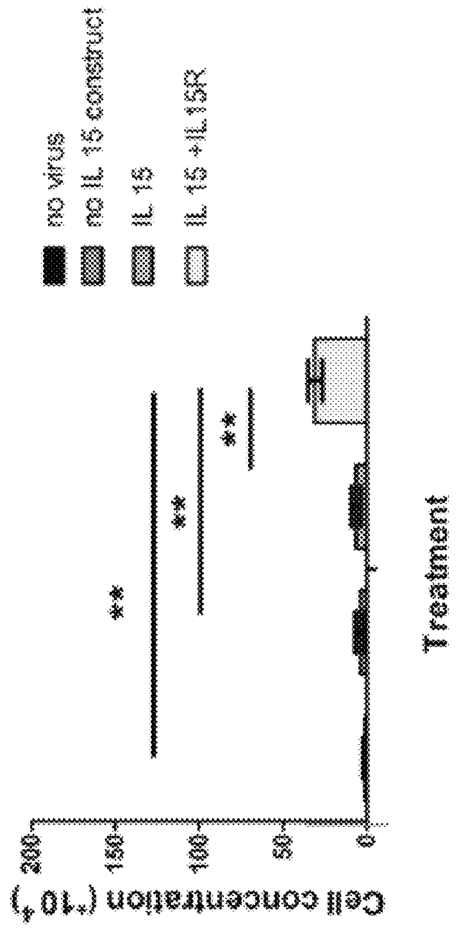
FIG. 20 depicts results from experiments wherein incorporation of an IL15/IL15R expression cassette drives proliferation of transduced cells. 10-fold higher expansion of cells transduced to express the cytokine response cassette compared to controls.

Cells Transduced with the Virus Comprising the IL15/IL15R Expression Cassette Show Improved Proliferation Proliferation of resting human T cells transduced with viruses incorporating an IL15/IL15R expression cassette was measured by analyzing the cell concentration, and is shown in FIG. 20. Cells transduced with the virus incorporating an IL15/IL15R expression showed 10-fold higher expansion of cells transduced to express the cytokine response cassette compared to controls. Accordingly, cells transduced with the virus comprising the cytokine response cassette show improved proliferation.

Example 10

MV Pseudotyped Lentiviral Vectors Transduce CD8 and CD3e Cells

Human T cells were activated with beads and exposed to a CD8 or CD3e targeting MV-pseudotyped lentiviral vector. Flow cytometry data showed expression of NGFR and CD8 or NGFR and CD3e. Accordingly, the MV pseudotyped lentiviral vector targets CD8 and CD3e cells.

Example 11

MV-Based Transduction is Highly Specific and Efficient In Vivo

Human PBMC (10E6) were engrafted into NSG mice and intraperitoneally injected with $2.5\times10^6$ TU CD4-specific MV vector, or VSVG vector. Mice were sacrificed at 2 days or 7 days following administration of the virus. Transduction was measured in the peritoneum, spleen, blood, and marrow. Mice injected with the MV vector showed on target transduction in all analyzed tissues or cells, as compared to VSVG control. Accordingly, MV-based transduction is highly specific and efficient in vivo.

Example 12

Structural Modifications of the Basic CAR Architecture Significantly Improve Transduction CD4+ cells were transduced with a "standard" CAR comprising an scFv, CD8 hinge, TM CD8, 4-1 BB, and CD3 zeta domains; "modified 1" CAR comprising an scFv, NGFR stem, NGFR transmembrane, 4-1BB, and CD3 zeta domains; or "modified 2" CAR comprising an scFv, NGFR Cys domain, NGFR stem, NGFR transmembrane, 4-1 BB, and CD3 zeta domains. Transduction was measured and showed increase in cells transduced with modified 1 and modified 2 CAR constructs, as compare to the standard CAR. Accordingly, structural modifications of the basic CAR architecture significantly improve transduction.

Example 13

Nipah-Based CAR-T Cells Show Similar Activity to VSVG-Based CAR-T Cells

Cells were transduced with the VSVG vector or the Nipah CAR vector. Expression of CD107, GM-CSF, or IFN-gamma was measured by flow cytometry. Cells transduced with the Nipah CAR vector showed similar expression patterns of all 3 markers as compared to VSVG transduced cells. Accordingly, Nipah-based CAR-T cells show similar activity to VSVG-based CAR-T cells.

Example 14

HEK293 cells were transfected with plasmid A plus B or plasmid C (control) to produce NiV or VSV-G pseudotyped virus. Expression of GFP, BFP and mScarlet (RFP) were analyzed by flow cytometry 48 hours later. Co-expression of plasmid A plus plasmid B (i.e, a split vector system) reconstituted mScarlet expression via protein splicing mediated by the inteins present in the expressed polypeptides. Cells were also shown to express GFP and BFP. Flow cytometry demonstrated that the mScarlet was produced, demonstrating that the same cells were transfected with the two viral vectors and that the inteins functioned to produce the mScarlet.

Other Embodiments

The recitation of a listing of elements in any definition of a variable herein includes definitions of that variable as any single element or combination (or subcombination) of listed elements. The recitation of an embodiment herein includes that embodiment as any single embodiment or in combination with any other embodiments or portions thereof.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

SEQUENCE LISTING

```
Sequence total quantity: 16
SEQ ID NO: 1           moltype = AA  length = 5
FEATURE                Location/Qualifiers
REGION                 1..5
                       note = Linker
REPEAT                 1..5
                       note = Repeat n times where n = an integer of at least 1 or
                        1-5
source                 1..5
                       mol_type = protein
                       organism = synthetic construct
SEQUENCE: 1
```

```
GSGGS                                                        5

SEQ ID NO: 2          moltype = AA  length = 4
FEATURE               Location/Qualifiers
REGION                1..4
                      note = Linker
REPEAT                1..4
                      note = Repeat n times where n = an integer of at least 1 or
                       1-5
source                1..4
                      mol_type = protein
                      organism = synthetic construct
SEQUENCE: 2
GGGS                                                         4

SEQ ID NO: 3          moltype = AA  length = 5
FEATURE               Location/Qualifiers
REGION                1..5
                      note = Linker
REPEAT                1..5
                      note = Repeat n times where n = an integer of at least 1 or
                       1-5
source                1..5
                      mol_type = protein
                      organism = synthetic construct
SEQUENCE: 3
GGGGS                                                        5

SEQ ID NO: 4          moltype = AA  length = 5
FEATURE               Location/Qualifiers
REGION                1..5
                      note = Linker
REPEAT                1..5
                      note = Repeat n times where n = an integer of at least 1 or
                       1-5
source                1..5
                      mol_type = protein
                      organism = synthetic construct
SEQUENCE: 4
GGSGG                                                        5

SEQ ID NO: 5          moltype = DNA  length = 4301
FEATURE               Location/Qualifiers
misc_feature          1..4301
                      note = xHIV gag-pol
source                1..4301
                      mol_type = other DNA
                      organism = synthetic construct
SEQUENCE: 5
atgggtgcga gagcgtcggt attaagcggg ggagaattag ataaatggga aaaaattcgg  60
ttaaggccag ggggaaagaa acaatataaa ctaaaacata tagtatgggc aagcagggag  120
ctagaacgat tcgcagttaa tcctggcctt ttagagacat cagaaggctg tagacaaata  180
ctgggacagc tacaaccatc ccttcagaca ggatcagaag aacttagatc attatataat  240
acaatagcag tcctctattg tgtgcatcaa aggatagatg taaaagacac taaggaagcc  300
ttagataaga tagaggaaga acaaaacaaa agtaagaaaa aggcacagca agcagcagct  360
gacacaggaa acaacagcca ggtcagccaa aattacccag tacaacaaat aggtggtaac  420
tatgtccacc tgccattaag cccgagaaca ttaaatgcct gggtaaaatt gatagaggaa  480
aagaaatttg gagcagaagt agtgccagga tttcaggcac tgtcagaagg ttgcaccccc  540
tatgacatta atcagatgtt aaattgtgtg ggagaccatc aagcggctat gcagattatc  600
agagatatta taaacgagga ggttgcagat tgggacttgc agcacccaca accagctcca  660
caacaaggac aacttaggga gccgtcagga tcagatattg caggaacaac tagttcagta  720
gatgaacaaa tccagtggat gtacagacaa cagaacccca taccagtagg caacatttac  780
aggagatgga tccaactggg gttgcaaaaa tgtgtcagaa tgtataaccc aacaaacatt  840
ctagatgtaa aacaagggcc aaaagagcca tttcagagct atgtagacag gttctacaaa  900
agtttaagag cagaacagac agatgcagca gtaaagaatt ggatgactca aacactgctg  960
attcaaaatg ctaacccaga ttgcaagcta gtgctgaagg ggttgggacc aggagcgaca  1020
ctagaagaaa tgatgacagc atgtcaggga gtggggggac ccggccataa agcaagagtt  1080
ttggctgaag caatgagcca agtaacaaat ccagctacca taatgataca gaaaggcaat  1140
tttaggaacc aaagaaagac tgttaagtgt ttcaattgtg gcaaagaagg gcacatagcc  1200
aaaaattgca gggcccctag gaaaaagggc tgttggaaat gtggaaagga aggacaccaa  1260
atgaaagatt gtactgagag acaggctaat tttttaggga agatctggcc ttcccacaag  1320
ggaaggccag ggaatttttct tcagagcaga ccagagccaa cagccccacc agaagagagc  1380
ttcaggtttg gggaagagac aacaactccc tctcagaagc aggagccgat agacaaggaa  1440
ctgtatcctt tagcttccct cagatcactc tttggcagcg acccctcgtc acaataaaga  1500
taggggggca attaaaggaa gctctattag atacaggagc agatgataca gtattagaag  1560
aaatgaattt gccaggaaga tggaaaccaa aaatgatagg gggaattgga ggttttatca  1620
aagtaagaca gtatgatcag atactcatag aaatctgcgg acataaagct ataggtacag  1680
tattagtagg acctacacct gtcaacataa ttggaagaaa tctgttgact cagattggct  1740
gcactttaaa ttttcccatt agtcctattg agactgtacc agtaaaatta aagccaggaa  1800
```

-continued

```
tggatggccc aaaagttaaa caatggccat tgacagaaga aaaaataaaa gcattagtag  1860
aaatttgtac agaaatggaa aaggaaggaa aaatttcaaa aattgggcct gaaaatccat  1920
acaatactcc agtatttgcc ataaagaaaa aagacagtac taaatggaga aaattagtag  1980
atttcagaga acttaataag agaactcaag atttctggga agttcaatta ggaataccac  2040
atcctgcagg gttaaaacag aaaaaatcag taacagtact ggatgtgggc gatgcatatt  2100
tttcagttcc cttagataaa gacttcagga agtatactgc atttaccata cctagtataa  2160
acaatgagac accagggatt agatatcagt acaatgtgct tccacaggga tggaaaggat  2220
caccagcaat attccagtgt agcatgacaa aaatcttaga gccttttaga aaacaaaatc  2280
cagacatagt catctatcaa tacatggatg atttgtatgt aggatctgac ttagaaatag  2340
ggcagcatag aacaaaaata gaggaactga gacaacatct gttgaggtgg ggatttacca  2400
caccagacaa aaaacatcag aaagaacctc cattcctttg gatgggttat gaactccatc  2460
ctgataaatg gacagtacag cctatagtgc tgccagaaaa ggacagctgg actgtcaatg  2520
acatacagaa attagtggga aaattgaatt gggcaagtca gatttatgca gggattaaag  2580
taaggcaatt atgtaaactt cttaggggaa ccaaagcact aacagaagta gtaccactaa  2640
cagaagaagc agagctagaa ctggcagaaa acagggagat tctaaaagaa ccggtacatg  2700
gagtgtatta tgacccatca aaagacttaa tagcagaaat acagaagcag gggcaaggcc  2760
aatggacata tcaaatttat caagagccat ttaaaaatct gaaaacagga aagtatgcaa  2820
gaatgaaggg tgcccacact aatgatgtga aacaattaac agaggcagta caaaaaatag  2880
ccacagaaag catagtaata tggggaaaga ctcctaaatt taaattaccc atacaaaagg  2940
aaacatggga agcatggtgg acagagtatt ggcaagccac ctggattcct gagtgggagt  3000
ttgtcaatac ccctccctta gtgaagttat ggtaccagtt agagaaagaa cccataatag  3060
gagcagaaac tttctatgta gatggggcag ccaataggga aactaaatta ggaaaagcag  3120
gatatgtaac tgacagagga agacaaaaag ttgtccccct aacggacaca acaaatcaga  3180
agactgagtt acaagcaatt catctagctt tgcaggattc gggattagaa gtaaacatag  3240
tgacagactc acaatatgca ttgggaatca ttcaagcaca accagataag agtgaatcag  3300
agttagtcag tcaaataata gagcagttaa taaaaaagga aaaagtctac ctggcatggg  3360
taccagcaca caaaggaatt ggaggaaatg aacaagtaga taaattggtc agtgctggaa  3420
tcaggaaagt actattttta gatggaatag ataaggccca agaagaacat gagaaatatc  3480
acagtaattg gagagcaatg gctagtgatt ttaacctacc acctgtagta gcaaaagaaa  3540
tagtagccag ctgtgataaa tgtcagctaa aaggggaagc catgcatgga caagtagact  3600
gtagcccagg aatatggcag ctagattgta cacatttaga aggaaaagtt atcttggtag  3660
cagttcatgt agccagtgga tatatagaag cagaagtaat tccagcagag acagggcaag  3720
aaacagcata cttcctctta aaattagcag gaagatggcc agtaaaaaca gtacatacag  3780
acaatggcag caatttcacc agtactacag ttaaggccgc ctgttggtgg gcggggatca  3840
agcaggaatt tggcattccc tacaatcccc aaagtcaagg agtaatagaa tctatgaata  3900
aagaattaaa gaaaattata ggacaggtaa gagatcaggc tgaacatctt aagacagcag  3960
tacaaatggc agtattcatc cacaatttta aaagaaaagg ggggattggg gggtacagtg  4020
caggggaaag aatagtagac ataatagcaa cagacataca aactaaagaa ttacaaaaac  4080
aaattacaaa aattcaaaat tttcgggttt attacaggga cagcagagat ccagtttgga  4140
aaggaccagc aaagctcctc tggaaaggtg aaggggcagt agtaatacaa gataatagtg  4200
acataaaagt agtgccaaga agaaaagcaa agatcatcag ggattatgga aaacagatgg  4260
caggtgatga ttgtgtggca agtagacagg atgaggatta a                       4301

SEQ ID NO: 6           moltype = DNA  length = 1497
FEATURE                Location/Qualifiers
misc_feature           1..1497
                       note = 5'-3' xHIV gag protein nt
source                 1..1497
                       mol_type = other DNA
                       organism = synthetic construct
SEQUENCE: 6
atgggtgcga gagcgtcggt attaagcggg ggagaattag ataaatggga aaaaattcgg  60
ttaaggccag gggggaaagaa acaatataaa ctaaaacata tagtatgggc aagcagggag  120
ctagaacgat tcgcagttaa tcctggcctt ttagagacat cagaaggctg tagacaaata  180
ctgggacagc tacaaccatc ccttcagaca ggatcagaag aacttagatc attatataat  240
acaatagcag tcctctattg tgtgcatcaa aggatagatg taaaagacac taaggaagcc  300
ttagataaga tagaggaaga acaaaacaaa agtaagaaaa aggcacagca agcagcagct  360
gacacaggaa acaacagcca ggtcagccaa aattacccag tacaacaaat aggtggtaac  420
tatgtccacc tgccattaag cccgagaaca ttaaatgcct gggtaaaatt gatagaggaa  480
aagaaatttg gagcagaagt agtgccagga tttcaggcac tgtcagaagg ttgcaccccc  540
tatgacatta atcagatgtt aaattgtgtg ggagaccatc aagcggctat gcagattatc  600
agagatatta taaacgagga ggttgcagat tgggacttgc agcacccaca accagctcca  660
caacaaggac aacttaggga gccgtcagga tcagatattg caggaacaac tagttcagta  720
gatgaacaaa tccagtggat gtacagacaa cagaacccca taccagtagg caacatttac  780
aggagatgga tccaactggg gttgcaaaaa tgtgtcagaa tgtataaccc aacaaacatt  840
ctagatgtaa aacaagggcc aaaagagcca tttcagagct atgtagacag gttctacaaa  900
agtttaagag cagaacagac agatgcagca gtaaagaatt ggatgactca aacactgctg  960
attcaaaatg ctaacccaga ttgcaagcta gtgctgaagg ggttgggacc aggagcgaca  1020
ctagaagaaa tgatgacagc atgtcaggga gtgggggac ccggccataa agcaagagtt  1080
ttggctgaag caatgagcca agtaacaaat ccagctacca taatgataca gaaaggcaat  1140
tttaggaacc aaagaaagac tgttaagtgt ttcaattgtg gcaaagaagg gcacatagcc  1200
aaaaattgca gggcccctag gaaaaagggc tgttggaaat gtggaaagga aggacaccaa  1260
atgaaagatt gtactgagag acaggctaat tttttaggga agatctggcc ttcccacaag  1320
ggaaggccag ggaattttct tcagagcaga ccagagccaa cagccccacc agaagagagc  1380
ttcaggtttg ggaagagac aacaactccc tctcagaagc aggagccgat agacaaggaa  1440
ctgtatcctt tagcttccct cagatcactc tttggcagcg acccctcgtc acaataa     1497

SEQ ID NO: 7           moltype = DNA  length = 619
FEATURE                Location/Qualifiers
```

```
misc_feature           1..619
                       note = 5'-3' xHIV SIV element nt
source                 1..619
                       mol_type = other DNA
                       organism = synthetic construct
SEQUENCE: 7
aaaattaccc agtacaacaa ataggtggta actatgtcca cctgccatta agcccgagaa  60
cattaaatgc ctgggtaaaa ttgatagagg aaaagaaatt tggagcagaa gtagtgccag  120
gatttcaggc actgtcagaa ggttgcaccc cctatgacat taatcagatg ttaaattgtg  180
tgggagacca tcaagcggct atgcagatta tcagagatat tataaacgag gaggttgcag  240
attgggactt gcagcaccca caaccagctc cacaacaagg acaacttagg gagccgtcag  300
gatcagatat tgcaggaaca actagttcag tagatgaaca aatccagtgg atgtacagac  360
aacagaaccc cataccagta ggcaacattt acaggagatg gatccaactg ggttgcaaa   420
aatgtgtcag aatgtataac ccaacaaaca ttctagatgt aaaacaaggg ccaaaagagc  480
catttcagag ctatgtagac aggttctaca aaagtttaag agcagaacag acagatgcag  540
cagtaaagaa ttggatgact caaacactgc tgattcaaaa tgctaaccca gattgcaagc  600
tagtgctgaa ggggttggg                                               619

SEQ ID NO: 8           moltype = DNA  length = 3011
FEATURE                Location/Qualifiers
misc_feature           1..3011
                       note = 5'-3' xHIV Pol protein nt
source                 1..3011
                       mol_type = other DNA
                       organism = synthetic construct
SEQUENCE: 8
tttttaggga agatctggcc ttcccacaag ggaaggccag ggaattttct tcagagcaga  60
ccagagccaa cagccccacc agaagagagc ttcaggtttg gggaagagac aacaactccc  120
tctcagaagc aggagccgat agacaaggaa ctgtatcctt tagcttccct cagatcactc  180
tttggcagcg accccctcgtc acaataaaga tagggggca attaaaggaa gctctattag  240
atacaggagc agatgataca gtattagaag aaatgaattt gccaggaaga tggaaaccaa  300
aaatgatagg gggaattgga ggttttatca aagtaagaca gtatgatcag atactcatag  360
aaatctgcgg acataaagct ataggtacag tattagtagg acctacacct gtcaacataa  420
ttggaagaaa tctgttgact cagattggct gcactttaaa ttttcccatt agtcctattg  480
agactgtacc agtaaaatta aagccaggaa tggatggccc aaaagttaaa caatggccat  540
tgacagaaga aaaaataaaa gcattagtag aaatttgtac agaaatggaa aaggaaggaa  600
aaatttcaaa aattgggcct gaaaatccat acaatactcc agtatttgcc ataaagaaaa  660
aagacagtac taaatggaga aaattagtag atttcagaga acttaataag agaactcaag  720
atttctggga agttcaatta ggaataccac atcctgcagg gttaaaacag aaaaaatcag  780
taacagtact ggatgtgggc gatgcatatt tttcagttcc cttagataaa gacttcagga  840
agtatactgc atttaccata cctagtataa acaatgagac accagggatt agatatcagt  900
acaatgtgct tccacaggga tggaaaggat caccagcaat attccagtgt agcatgacaa  960
aaatcttaga gccttttaga aaacaaaatc cagacatagt catctatcaa tacatggatg  1020
atttgtatgt aggatctgac ttagaaatag ggcagcatag aacaaaaata gaggaactga  1080
gacaacatct gttgaggtgg ggatttacca caccagacaa aaaacatcag aaagaacctc  1140
cattcctttg gatgggttat gaactccatc ctgataaatg gacagtacag cctatagtgc  1200
tgccagaaaa ggacagctgg actgtcaatg acatacagaa attagtggga aaattgaatt  1260
gggcaagtca gatttatgca gggattaaag taaggcaatt atgtaaactt cttaggggaa  1320
ccaaagcact aacagaagta gtaccactaa cagaagaagc agagctagaa ctggcagaaa  1380
acagggagat tctaaaagaa ccggtacatg gagtgtatta tgacccatca aaagacttaa  1440
tagcagaaat acagaagcag gggcaaggcc aatggacata tcaaatttat caagagccat  1500
ttaaaaatct gaaaacagga aagtatgcaa gaatgaaggg tgcccacact aatgatgtga  1560
aacaattaac agaggcagta caaaaaatag ccacagaaag catagtaata tggggaaaga  1620
ctcctaaatt taaattaccc atacaaaagg aaacatggga agcatggtgg acagagtatt  1680
ggcaagccac ctggattcct gagtgggagt ttgtcaatac ccctcccta gtgaagttat   1740
ggtaccagtt agagaaagaa cccataatag gagcagaaac tttctatgta gatggggcag  1800
ccaataggga aactaaatta ggaaaagcag gatatgtaac tgacagagga agacaaaaag  1860
ttgtcccct aacggacaca acaaatcaga agactgagtt acaagcaatt catctagctt   1920
tgcaggattc gggattagaa gtaaacatag tgacagactc acaatatgca ttgggaatca  1980
ttcaagcaca accagataag agtgaatcag agttagtcag tcaaataata gagcagttaa  2040
taaaaaagga aaaagtctac ctggcatggg taccagcaca caaaggaatt ggaggaaatg  2100
aacaagtaga taaattggtc agtgctggaa tcaggaaagt actattttta gatggaatag  2160
ataaggccca agaagaacat gagaaatatc acagtaattg gagagcaatg gctagtgatt  2220
ttaacctacc acctgtagta gcaaaagaaa tagtagccag ctgtgataaa tgtcagctaa  2280
aaggggaagc catgcatgga caagtagact gtagcccagg aatatggcag ctagattgta  2340
cacatttaga aggaaaagtt atcttggtag cagttcatgt agccagtgga tatatagaag  2400
cagaagtaat tccagcagag acagggcaag aaacagcata cttcctctta aaattagcag  2460
gaagatggcc agtaaaaaca gtacatacag acaatggcag caatttcacc agtactacag  2520
ttaaggccgc ctgttggtgg gcggggatca agcaggaatt tggcattccc tacaatcccc  2580
aaagtcaagg agtaatagaa tctatgaata aagaattaaa gaaaattata ggacaggtaa  2640
gagatcaggc tgaacatctt aagacagcag tacaaatggc agtattcatc cacaatttta  2700
aaagaaaagg ggggattggg gggtacagtg caggggaaag aatagtagac ataatagcaa  2760
cagacataca aactaaagaa ttacaaaaac aaattacaaa aattcaaaat tttcgggttt  2820
attacaggga cagcagagat ccagtttgga aaggaccagc aaagctcctc tggaaaggtg  2880
aaggggcagt agtaatacaa gataatagtg acataaaagt agtgccaaga agaaaagcaa  2940
agatcatcag ggattatgga aaacagatgg caggtgatga ttgtgtggca agtagacagg  3000
atgaggatta a                                                       3011

SEQ ID NO: 9           moltype = AA  length = 498
```

-continued

```
FEATURE                Location/Qualifiers
REGION                 1..498
                       note = gag protein
source                 1..498
                       mol_type = protein
                       organism = synthetic construct
SEQUENCE: 9
MGARASVLSG GELDKWEKIR LRPGGKKQYK LKHIVWASRE LERFAVNPGL LETSEGCRQI  60
LGQLQPSLQT GSEELRSLYN TIAVLYCVHQ RIDVKDTKEA LDKIEEEQNK SKKKAQQAAA  120
DTGNNSQVSQ NYPVQQIGGN YVHLPLSPRT LNAWVKLIEE KKFGAEVVPG FQALSEGCTP  180
YDINQMLNCV GDHQAAMQII RDIINEEVAD WDLQHPQPAP QQGQLREPSG SDIAGTTSSV  240
DEQIQWMYRQ QNPIPVGNIY RRWIQLGLQK CVRMYNPTNI LDVKQGPKEP FQSYVDRFYK  300
SLRAEQTDAA VKNWMTQTLL IQNANPDCKL VLKGLGPGAT LEEMMTACQG VGGPGHKARV  360
LAEAMSQVTN PATIMIQKGN FRNQRKTVKC FNCGKEGHIA KNCRAPRKKG CWKCGKEGHQ  420
MKDCTERQAN FLGKIWPSHK GRPGNFLQSR PEPTAPPEES FRFGEETTTP SQKQEPIDKE  480
LYPLASLRSL FGSDPSSQ                                              498

SEQ ID NO: 10          moltype = AA  length = 912
FEATURE                Location/Qualifiers
REGION                 1..912
                       note = Pol protein
source                 1..912
                       mol_type = protein
                       organism = synthetic construct
SEQUENCE: 10
MNLPGRWKPK MIGGIGGFIK VRQYDQILIE ICGHKAIGTV LVGPTPVNII GRNLLTQIGC  60
TLNFPISPIE TVPVKLKPGM DGPKVKQWPL TEEKIKALVE ICTEMEKEGK ISKIGPENPY  120
NTPVFAIKKK DSTKWRKLVD FRELNKRTQD FWEVQLGIPH PAGLKQKKSV TVLDVGDAYF  180
SVPLDKDFRK YTAFTIPSIN NETPGIRYQY NVLPQGWKGS PAIFQCSMTK ILEPFRKQNP  240
DIVIYQYMDD LYVGSDLEIG QHRTKIEELR QHLLRWGFTT PDKKHQKEPP FLWMGYELHP  300
DKWTVQPIVL PEKDSWTVND IQKLVGKLNW ASQIYAGIKV RQLCKLLRGT KALTEVVPLT  360
EEAELELAEN REILKEPVHG VYYDPSKDLI AEIQKQGQGQ WTYQIYQEPF KNLKTGKYAR  420
MKGAHTNDVK QLTEAVQKIA TESIVIWGKT PKFKLPIQKE TWEAWWTEYW QATWIPEWEF  480
VNTPPLVKLW YQLEKEPIIG AETFYVDGAA NRETKLGKAG YVTDRGRQKV VPLTDTTNQK  540
TELQAIHLAL QDSGLEVNIV TDSQYALGII QAQPDKSESE LVSQIIEQLI KKEKVYLAWV  600
PAHKGIGGNE QVDKLVSAGI RKVLFLDGID KAQEEHEKYH SNWRAMASDF NLPPVVAKEI  660
VASCDKCQLK GEAMHGQVDC SPGIWQLDCT HLEGKVILVA VHVASGYIEA EVIPAETGQE  720
TAYFLLKLAG RWPVKTVHTD NGSNFTSTTV KAACWWAGIK QEFGIPYNPQ SQGVIESMNK  780
ELKKIIGQVR DQAEHLKTAV QMAVFIHNFK RKGGIGGYSA GERIVDIIAT DIQTKELQKQ  840
ITKIQNFRVY YRDSRDPVWK GPAKLLWKGE GAVVIQDNSD IKVVPRRKAK IIRDYGKQMA  900
GDDCVASRQD ED                                                    912

SEQ ID NO: 11          moltype = AA  length = 520
FEATURE                Location/Qualifiers
REGION                 1..520
                       note = Measles d30
source                 1..520
                       mol_type = protein
                       organism = synthetic construct
SEQUENCE: 11
MGLKVNVSAI FMAVLLTLQT PTGQIHWGNL SKIGVVGIGS ASYKVMTRSS HQSLVIKLMP  60
NITLLNNCTR VEIAEYRRLL RTVLEPIRDA LNAMTQNIRP VQSVASSRRH KRFAGVVLAG  120
AALGVATAAQ ITAGIALHQS MLNSQAIDNL RASLETTNQA IEAIRQAGQE MILAVQGVQD  180
YINNELIPSM NQLSCDLIGQ KLGLKLLRYY TEILSLFGPS LRDPISAEIS IQALSYALGG  240
DINKVLEKLG YSGGDLLGIL ESRGIKARIT HVDTESYLIV LSIAYPTLSE IKGVIVHRLE  300
GVSYNIGSQE WYTTVPKYVA TQGYLISNFD ESSCTFMPEG TVCSQNALYP MSPLLQECLR  360
GSTKSCARTL VSGSFGNRFI LSQGNLIANC ASILCKCYTT GTIINQDPDK ILTYIAADHC  420
PVVEVNGVTI QVGSRRYPDA VYLHRIDLGP PILLERLDVG TNLGNAIAKL EDAKELLESS  480
DQILRSMKGL SSTCIVYILI AVCLGGLIGI PALICCCRGR                      520

SEQ ID NO: 12          moltype = AA  length = 601
FEATURE                Location/Qualifiers
REGION                 1..601
                       note = Measles d18+4A
source                 1..601
                       mol_type = protein
                       organism = synthetic construct
SEQUENCE: 12
MGSRIVINRE HLMIDRPYVL LAVLFVMFLS LIGLLAIAGI RLHRAAIYTA EIHKSLSTNL  60
DVTNSIEHQV KDVLTPLFKI IGDEVGLRTP QRFTDLVKFI SDKIKFLNPD REYDFRDLTW  120
CINPPERIKL DYDQYCADVA AEELMNALVN STLLETRTTN QFLAVSKGNC SGPTTIRGQF  180
SNMSLSLLDL YLGRGYNVSS IVTMTSQGMY GGTYLVEKPN LSSKRSELSQ LSMYRVFEVG  240
VIRNPGLGAP VFHMTNYLEQ PVSNDLSNCM VALGELKLAA LCHGEDSITI PYQGSGKGVS  300
FQLVKLGVWK SPTDMQSWVP LSTDDPVIDR LYLSSHRGVI ADNQAKWAVP TTRTDDKLRM  360
ETCFQQACKG KIQALCENPE WAPLKDNRIP SYGVLSVDLS LTVELKIKIA SGFGPLITHG  420
SGMDLYKSNH NNVYWLTIPP MKNLALGVIN TLEWIPRFKV SPALFNVPIK EAGEDCHAPT  480
YLPAEVDGDV KLSSNLVILP GQDLQYVLAT YDTSAVEHAV VYYVYSPSRL SSYFYPFRLP  540
IKGVPIELQV ECFTWDQKLW CRHFCVLADS ESGGHITHSG MVGMGVSCTV TREDGTNRRG  600
G                                                                601
```

```
SEQ ID NO: 13          moltype = AA  length = 524
FEATURE                Location/Qualifiers
REGION                 1..524
                       note = Nipah d30
source                 1..524
                       mol_type = protein
                       organism = synthetic construct
SEQUENCE: 13
MVVILDKRCY CNLLILILMI SECSVGILHY EKLSKIGLVK GVTRKYKIKS NPLTKDIVIK  60
MIPNVSNMSQ CTGSVMENYK TRLNGILTPI KGALEIYKNN THDLVGDVRL AGVIMAGVAI  120
GIATAAQITA GVALYEAMKN ADNINKLKSS IESTNEAVVK LQETAEKTVY VLTALQDYIN  180
TNLVPTIDKI SCKQTELSLD LALSKYLSDL LFVFGPNLQD PVSNSMTIQA ISQAFGGNYE  240
TLLRTLGYAT EDFDDLLESD SITGQIIYVD LSSYYIIVRV YFPILTEIQQ AYIQELLPVS  300
FNNDNSEWIS IVPNFILVRN TLISNIEIGF CLITKRSVIC NQDYATPMTN NMRECLTGST  360
EKCPRELVVS SHVPRFALSN GVLFANCISV TCQCQTTGRA ISQSGEQTLL MIDNTTCPTA  420
VLGNVIISLG KYLGSVNYNS EGIAIGPPVF TDKVDISSQI SSMNQSLQQS KDYIKEAQRL  480
LDTVNPSLIS MLSMIILYVL SIASLCIGLI TFISFIIVEK KRNT                  524

SEQ ID NO: 14          moltype = AA  length = 569
FEATURE                Location/Qualifiers
REGION                 1..569
                       note = Nipah d18+4A
source                 1..569
                       mol_type = protein
                       organism = synthetic construct
SEQUENCE: 14
MKKINEGLLD SKILSAFNTV IALLGSIVII VMNIMIIQNY TRSTDNQAVI KDALQGIQQQ  60
IKGLADKIGT EIGPKVSLID TSSTITIPAN IGLLGSKISQ STASINENVN EKCKFTLPPL  120
KIHECNISCP NPLPFREYRP QTEGVSNLVG LPNNICLQKT SNQILKPKLI SYTLPVVGQS  180
GTCITDPLLA MDEGYFAYSH LERIGSCSRG VSKQRIIGVG EVLDRGDEVP SLFMTNVWTP  240
PNPNTVYHCS AVYNNEFYYV LCAVSTVGDP ILNSTYWSGS LMMTRLAVKP KSNGGGYNQH  300
QLALRSIEKG RYDKVMPYGP SGIKQGDTLY FPAVGFLVRT EFKYNDSNCP ITKCQYSKPE  360
NCRLSMGIRP NSHYILRSGL LKYNLSDGEN PKVVFIEISD QRLSIGSPSK IYDSLGQPVF  420
YQASFSWDTM IKFGDVLTVN PLVVNWRNNT VISRPGQSQC PRFNTCPAIC AEGVYNDAFL  480
IDRINWISAG VFLDSNATAA NPVFTVFKDN EILYRAQLAS EDTNAQKTIT NCFLLKNKIW  540
CISLVEIYDT GDNVIRPKLF AVKIPEQCT                                   569

SEQ ID NO: 15          moltype = AA  length = 868
FEATURE                Location/Qualifiers
REGION                 1..868
                       note = US_10415057_2
source                 1..868
                       mol_type = protein
                       organism = synthetic construct
SEQUENCE: 15
MGSRIVINRE HLMIDRPYVL LAVLFVMFLS LIGLLAIAGI RLHRAAIYTA EIHKSLSTNL  60
DVTNSIEHQV KDVLTPLFKI IGDEVGLRTP QRFTDLVKFI SDKIKFLNPD REYDFRDLTW  120
CINPPERIKL DYDQYCADVA AEELMNALVN STLLETRTTN QFLAVSKGNC SGPTTIRGQF  180
SNMSLSLLDL YLGRGYNVSS IVTMTSQGMY GGTYLVEKPN LSSKRSELSQ LSMYRVFEVG  240
VIRNPGLGAP VFHMTNYLEQ PVSNDLSNCM VALGELKLAA LCHGEDSITI PYQGSGKGVS  300
FQLVKLGVWK SPTDMQSWVP LSTDDPVIDR LYLSSHRGVI ADNQAKWAVP TTRTDDKLRM  360
ETCFQQACKG KIQALCENPE WAPLKDNRIP SYGVLSVDLS LTVELKIKIA SGFGPLITHG  420
SGMDLYKSNH NNVYWLTIPP MKNLALGVIN TLEWIPRFKV SPALFTVPIK EAGGDCHAPT  480
YLPAEVDGDV KLSSNLVILP GQDLQYVLAT YDTSAVEHAV VYYVYSPSRL SSYFYPFRLP  540
IKGVPIELQV ECFTWDQKLW CRHFCVLADS ESGGHITHSG MVGMGVSCTV TREDGTNAAQ  600
PAIEGRMAQV QLVQSGAELV KPGASVKMSC KASGYTFTSY NMHWVKQTPG QGLEWIGAIY  660
PGNGDTSYNQ KFKGKATLTA DKSSSTAYMQ LSSLTSEDSA VYYCARAQLR PNYWYFDVWG  720
AGTTVTVSKI SGGGGSGGGG SGGGGSGGSS DIVLSQSPAI LSASPGEKVT MTCRASSSVS  780
YMHWYQQKPG SSPKPWIYAT SNLASGVPAR FSGSGSGTSY SLTISRVEAE DAATYYCQQW  840
ISNPPTFGAG TKLELKAAAR GSHHHHHH                                    868

SEQ ID NO: 16          moltype = AA  length = 669
FEATURE                Location/Qualifiers
REGION                 1..669
                       note = US_10415057_4
source                 1..669
                       mol_type = protein
                       organism = synthetic construct
SEQUENCE: 16
MGSRIVINRE HLMIDRPYVL LAVLFVMFLS LIGLLAIAGI RLHRAAIYTA EIHKSLSTNL  60
DVTNSIEHQV KDVLTPLFKI IGDEVGLRTP QRFTDLVKFI SDKIKFLNPD REYDFRDLTW  120
CINPPERIKL DYDQYCADVA AEELMNALVN STLLETRTTN QFLAVSKGNC SGPTTIRGQF  180
SNMSLSLLDL YLGRGYNVSS IVTMTSQGMY GGTYLVEKPN LSSKRSELSQ LSMYRVFEVG  240
VIRNPGLGAP VFHMTNYLEQ PVSNDLSNCM VALGELKLAA LCHGEDSITI PYQGSGKGVS  300
FQLVKLGVWK SPTDMQSWVP LSTDDPVIDR LYLSSHRGVI ADNQAKWAVP TTRTDDKLRM  360
ETCFQQACKG KIQALCENPE WAPLKDNRIP SYGVLSVDLS LTVELKIKIA SGFGPLITHG  420
SGMDLYKSNH NNVYWLTIPP MKNLALGVIN TLEWIPRFKV SPALFTVPIK EAGGDCHAPT  480
YLPAEVDGDV KLSSNLVILP GQDLQYVLAT YDTSAVEHAV VYYVYSPSRL SSYFYPFRLP  540
```

-continued

```
IKGVPIELQV ECFTWDQKLW CRHFCVLADS ESGGHITHSG MVGMGVSCTV TREDGTNAAQ  600
PAMANSDSEC PLSHDGYCLH DGVCMYIEAL DKYACNCVVG YIGERCQYRD LKWWELRAAA  660
RGSHHHHHH                                                          669
```

What is claimed:

1. A viral vector system comprising a first viral particle and a second viral particle, wherein the first viral particle comprises a chimeric gag protein, a first targeting moiety that binds to a first target on a cell and a first nucleic acid molecule that encodes a first portion of a protein or a polypeptide of interest;

wherein the second viral particle comprises a chimeric gag protein, a second targeting moiety that binds to a second target on the cell and a second nucleic acid molecule that encodes a second portion of the protein or the polypeptide of interest; and wherein the first and second portions of the protein or polypeptide of interest are capable of forming a complete protein or polypeptide of interest inside the cell.

2. The viral vector system of claim 1, wherein the chimeric gag protein is xHIV gag protein.

3. The viral vector system of claim 1, wherein the chimeric gag protein comprises the amino acid sequence of SEQ ID NO: 9.

4. The viral vector system of claim 1, wherein the first targeting moiety is fused to a mutated fusion protein present on the surface of the first viral particle.

5. The viral vector system of claim 1, wherein the second targeting moiety is fused to a mutated fusion protein present on the surface of the second viral particle.

6. The viral vector system of claim 1, wherein the first viral particle, the second viral particle, or both the first and second viral particles are a lentivirus pseudotyped with:

a measles virus hemagglutinin (MV-HA) protein and/or a MV fusion (F) protein (MV-F), wherein the MV-HA protein or the MV-F protein comprises a mutation or a mutated binding domain compared to its naturally occurring protein; or a Nipah virus F protein and/or a Nipah virus G protein, wherein the Nipah virus F protein and/or the Nipah virus G protein comprises a mutation or a mutated binding domain compared to its naturally occurring protein.

7. The viral vector system of claim 6, wherein the first targeting moiety, the second targeting moiety, or both the first and second targeting moieties are independently fused to the MV-HA protein, the MV-F protein, the Nipah virus F protein, or the Nipah virus G protein.

8. The viral vector system of claim 1, wherein the first targeting moiety and the second targeting moiety are each, individually, a scFv, an antigen binding domain, a DARPIN, a VHH, or a FN3 domain.

9. The viral vector system of claim 1, wherein the first targeting moiety and the second targeting moiety each, individually, bind to a protein selected from the group consisting of Stem Cell Factor protein (SCF, KIT-ligand, KL, or steel factor) or a moiety that binds to ckit (CD117), CD4, CD8, CD3, CD3D, CD3E, CD3G, CD3Z, CD5, CD6, CD7, CD2, TCR alpha, TCR beta, TCR gamma, TCR delta, CD10, CD34, CD110, CD33, CD14, CD68, CCR7, CD62L, CD25, CCR2, CCR3, CCR4, CCR5, CCR6, CCR7, and CXCR3.

10. The viral vector system of claim 1, wherein the protein or polypeptide of interest is a chimeric antigen receptor (CAR).

11. The viral vector system of claim 10, wherein the CAR comprises an antigen binding domain, and wherein the antigen binding domain binds to CD20, CD22, CD123, CD38, CD19, BCMA, CD33, or CD79b.

12. A method of in vivo gene delivery comprising administering to a subject in need thereof a first viral particle and a second viral particle, wherein the first viral particle comprises a chimeric gag protein, a first targeting moiety that binds to a first target on a cell and a first nucleic acid molecule that encodes a first portion of a protein or a polypeptide of interest;

wherein the second viral particle comprises a chimeric gag protein, a second targeting moiety that binds to a second target on the cell and a second nucleic acid molecule that encodes a second portion of the protein or the polypeptide of interest; and wherein the first and second portions of the protein or polypeptide of interest are capable of forming a complete protein or polypeptide of interest inside the cell.

13. The method of claim 12, wherein the chimeric gag protein is xHIV gag.

14. The method of claim 12, wherein the chimeric gag protein comprises the amino acid sequence of SEQ ID NO: 9.

15. The method of claim 12, wherein the method further comprises administering a dimerizing agent to form the protein or polypeptide of interest in the subject.

16. A method of treating a disease in a subject in need thereof, the method comprising administering to the subject a first viral particle and a second viral particle, wherein the first viral particle comprises a chimeric gag protein, a first targeting moiety that binds to a first target on a cell and a first nucleic acid molecule that encodes a first portion of a protein or a polypeptide of interest;

wherein the second viral particle comprises a chimeric gag protein, a second targeting moiety that binds to a second target on the cell and a second nucleic acid molecule that encodes a second portion of the protein or the polypeptide of interest; and wherein the first and second portions of the protein or polypeptide of interest are capable of forming a complete protein or polypeptide of interest inside the cell, wherein expression of the complete protein of polypeptide of interest inside the cell is useful for the treatment of the disease.

17. The method of claim 16, wherein the chimeric gag protein is xHIV gag.

18. The method of claim 16, wherein the chimeric gag protein comprises the amino acid sequence of SEQ ID NO: 9.

19. The method of claim 16, wherein the method further comprises administering a dimerizing agent to form the protein or polypeptide of interest in the subject.

* * * * *